United States Patent
Tohata

(10) Patent No.: US 12,319,943 B2
(45) Date of Patent: Jun. 3, 2025

(54) MUTANT PROTEASE

(71) Applicant: Kao Corporation, Tokyo (JP)

(72) Inventor: Masatoshi Tohata, Utsunomiya (JP)

(73) Assignee: Kao Corporation, Tokyo (JP)

( * ) Notice: Subject to any disclaimer, the term of this patent is extended or adjusted under 35 U.S.C. 154(b) by 776 days.

(21) Appl. No.: 17/435,853

(22) PCT Filed: Mar. 6, 2020

(86) PCT No.: PCT/JP2020/009570
§ 371 (c)(1),
(2) Date: Sep. 2, 2021

(87) PCT Pub. No.: WO2020/184410
PCT Pub. Date: Sep. 17, 2020

(65) Prior Publication Data
US 2022/0154109 A1    May 19, 2022

(30) Foreign Application Priority Data
Mar. 11, 2019   (JP) ................................ 2019-044267

(51) Int. Cl.
*C12N 9/56* (2006.01)
*C11D 3/386* (2006.01)
*C12N 9/54* (2006.01)
*C12N 15/75* (2006.01)
*C12P 21/02* (2006.01)

(52) U.S. Cl.
CPC ............ *C12N 9/54* (2013.01); *C11D 3/38618* (2013.01); *C12N 15/75* (2013.01); *C12P 21/02* (2013.01)

(58) Field of Classification Search
CPC ...................................................... C12N 9/54
See application file for complete search history.

(56) References Cited

U.S. PATENT DOCUMENTS

| | | | |
|---|---|---|---|
| 6,376,227 | B1 | 4/2002 | Takaiwa et al. |
| 10,717,949 | B2 * | 7/2020 | Yamada .................. C12N 15/09 |
| 2003/0022351 | A1 | 1/2003 | Hatada et al. |
| 2003/0049827 | A1 | 3/2003 | Ness et al. |
| 2004/0002432 | A1 | 1/2004 | Okuda et al. |
| 2005/0026804 | A1 | 2/2005 | Sato et al. |
| 2005/0214922 | A1 | 9/2005 | Okuda et al. |
| 2006/0078978 | A1 | 4/2006 | Okuda et al. |
| 2007/0015240 | A1 | 1/2007 | Svendsen et al. |
| 2012/0058928 | A1 | 3/2012 | Tohata et al. |
| 2015/0056681 | A1 | 2/2015 | Tohata et al. |
| 2015/0104856 | A1 * | 4/2015 | Astrid ................ C11D 3/38618 510/393 |
| 2019/0161708 | A1 | 5/2019 | Yamada et al. |

FOREIGN PATENT DOCUMENTS

| | | |
|---|---|---|
| JP | 2002-218989 A | 8/2002 |
| JP | 2004-122 A | 1/2004 |
| JP | 2004-508011 A | 3/2004 |
| JP | 2004-305175 A | 11/2004 |
| JP | 2004-305176 A | 11/2004 |
| JP | 2010-273672 A | 12/2010 |
| JP | 2010-273673 A | 12/2010 |
| JP | 2011-200249 A | 10/2011 |
| JP | 2013-233141 A | 11/2013 |
| JP | 2017-008303 A | 1/2017 |
| JP | 2017-221188 A | 12/2017 |
| WO | WO 99/18218 A1 | 4/1999 |
| WO | WO 2001-075087 A2 | 10/2001 |
| WO | WO 2010/056653 A2 | 5/2010 |

OTHER PUBLICATIONS

Q12XJ3_METBU. UnitProtKB/TrEMBL Database. Oct. 10, 2018.*
WP_060666408.1 (hypothetical protein [Bacillus sp, CHD6a]. NCBI Database. Jan. 27, 2016.*
WP_060666408.1 (S8 family peptidase [Bacillus sp. CHD6a]. NCBI database. Jan. 6, 2024.*
Nonaka. The crystal structure of an oxidatively stable subtilisin-like alkaline serine protease, KP-43, with a C-terminal beta-barrel domain. J Biol Chem. Nov. 5, 2004;279(45):47344-51. Epub Sep. 1, 2004.*
Saeki. Detergent alkaline proteases: enzymatic properties, genes, and crystal structures. Journal of Bioscience and Bioengineering, vol. 103, Issue 6, 2007, pp. 501-508.*
The extended European search report including the supplementary European search report and the European search opinion, dated Jul. 4, 2023, for EP Application No. 20771003.9, the European Patent Office, Munich, Germany.
International Search Report for PCT/JP2020/009570; I.A. fd Mar. 6, 2020, mailed Jun. 2, 2020, the Japan Patent Office, Tokyo, Japan.
International Preliminary Report on Patentability (IPRP), Chapter I of the Patent Cooperation Treaty, including the Written Opinion, for PCT/JP2020/009570; I.A. fd Mar. 6, 2020, issued Aug. 25, 2021, by the International Bureau of WIPO, Geneva, Switzerland.

* cited by examiner

*Primary Examiner* — Yong D Pak
(74) *Attorney, Agent, or Firm* — Sterne, Kessler, Goldstein & Fox P.L.L.C.

(57) ABSTRACT

Provided is a mutant protease with improved stability under acidic condition. A mutant protease that consists of the amino acid sequence as shown in SEQ ID NO:2 or an amino acid sequence having an identity of at least 90% thereto, in which the amino acid residue at a position corresponding to position 303 in the amino acid sequence as shown in SEQ ID NO:2 is substituted with another amino acid residue.

22 Claims, No Drawings
Specification includes a Sequence Listing.

SEQUENCE LISTING

```
<160> NUMBER OF SEQ ID NOS: 42

<210> SEQ ID NO 1
<211> LENGTH: 1302
<212> TYPE: DNA
<213> ORGANISM: Bacillus sp. KSM-KP43
<220> FEATURE:
<223> OTHER INFORMATION: Wild-type

<400> SEQUENCE: 1
aatgatgttg cgcgtggaat tgtcaaagcg gatgtggctc agagcagcta cgggttgtat      60
ggacaaggac agatcgtagc ggttgccgat acagggcttg atacaggtcg caatgacagt     120
tcgatgcatg aagccttccg cgggaaaatt actgcattat atgcattggg acggacgaat     180
aatgccaatg atacgaatgg tcatggtacg catgtggctg gctccgtatt aggaaacggc     240
tccactaata aaggaatggc gcctcaggcg aatctagtct tccaatctat catggatagc     300
ggtgggggac ttggaggact accttcgaat ctgcaaacct tattcagcca agcatacagt     360
gctggtgcca gaattcatac aaactcctgg ggagcagcag tgaatggggc ttacacaaca     420
gattccagaa atgtggatga ctatgtgcgc aaaaatgata tgacgatcct tttcgctgcc     480
gggaatgaag gaccgaacgg cggaaccatc agtgcaccag gcacagctaa aaatgcaata     540
acagtcggag ctacggaaaa cctccgccca agctttgggt cttatgcgga caatatcaac     600
catgtggcac agttctcttc acgtggaccg acaaaggatg gacggatcaa accggatgtc     660
atggcaccgg gaacgttcat actatcagca agatcttctc ttgcaccgga ttcctccttc     720
tgggcgaacc atgacagtaa atatgcatac atgggtggaa cgtccatggc tacaccgatc     780
gttgctggaa acgtggcaca gcttcgtgag cattttgtga aaacagagg catcacacca     840 aagccttctc tattaaaagc ggcactgatt gccggtgcag ctgacatcgg ccttggctac     900
ccgaacggta accaaggatg gggacgagtg acattggata aatccctgaa cgttgcctat     960
gtgaacgagt ccagttctct atccaccagc caaaaagcga cgtactcgtt tactgctact    1020
```

```
gccggcaagc ctttgaaaat ctccctggta tggtctgatg cccctgcgag cacaactgct    1080
tccgtaacgc ttgtcaatga tctggacctt gtcattaccg ctccaaatgg cacacagtat    1140
gtaggaaatg actttacttc gccatacaat gataactggg atggccgcaa taacgtagaa    1200
aatgtattta ttaatgcacc acaaagcggg acgtatacaa ttgaggtaca ggcttataac    1260
gtaccggttg gaccacagac cttctcgttg gcaattgtga at                       1302
```

<210> SEQ ID NO 2
<211> LENGTH: 434
<212> TYPE: PRT
<213> ORGANISM: Bacillus sp. KSM-KP43
<220> FEATURE:
<223> OTHER INFORMATION: Wild-type

<400> SEQUENCE: 2

```
Asn Asp Val Ala Arg Gly Ile Val Lys Ala Asp Val Ala Gln Ser Ser
1               5                   10                  15

Tyr Gly Leu Tyr Gly Gln Gly Gln Ile Val Ala Val Ala Asp Thr Gly
                20                  25                  30

Leu Asp Thr Gly Arg Asn Asp Ser Ser Met His Glu Ala Phe Arg Gly
            35                  40                  45

Lys Ile Thr Ala Leu Tyr Ala Leu Gly Arg Thr Asn Asn Ala Asn Asp
        50                  55                  60

Thr Asn Gly His Gly Thr His Val Ala Gly Ser Val Leu Gly Asn Gly
65                  70                  75                  80

Ser Thr Asn Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
                100                 105                 110

Thr Leu Phe Ser Gln Ala Tyr Ser Ala Gly Ala Arg Ile His Thr Asn
            115                 120                 125

Ser Trp Gly Ala Ala Val Asn Gly Ala Tyr Thr Thr Asp Ser Arg Asn
        130                 135                 140

Val Asp Asp Tyr Val Arg Lys Asn Asp Met Thr Ile Leu Phe Ala Ala
145                 150                 155                 160

Gly Asn Glu Gly Pro Asn Gly Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Tyr Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Val Lys Asn Arg Gly Ile Thr Pro Lys Pro Ser Leu Leu Lys Ala Ala
        275                 280                 285

Leu Ile Ala Gly Ala Ala Asp Ile Gly Leu Gly Tyr Pro Asn Gly Asn
    290                 295                 300

Gln Gly Trp Gly Arg Val Thr Leu Asp Lys Ser Leu Asn Val Ala Tyr
```

```
                  305                 310                 315                 320
Val Asn Glu Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
                340                 345                 350

Asp Ala Pro Ala Ser Thr Thr Ala Ser Val Thr Leu Val Asn Asp Leu
                355                 360                 365

Asp Leu Val Ile Thr Ala Pro Asn Gly Thr Gln Tyr Val Gly Asn Asp
        370                 375                 380

Phe Thr Ser Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
                420                 425                 430

Val Asn

<210> SEQ ID NO 3
<211> LENGTH: 434
<212> TYPE: PRT
<213> ORGANISM: Bacillus sp. KSM-KP43
<220> FEATURE:
<223> OTHER INFORMATION: Valiant

<400> SEQUENCE: 3

Asn Asp Val Ala Arg Gly Ile Val Lys Ala Asp Val Ala Gln Ser Val
1               5                   10                  15

Tyr Gly Leu Tyr Gly Gln Gly Gln Ile Val Ala Val Ala Asp Thr Gly
                20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
50                  55                  60

Pro Asn Gly His Gly Thr His Val Ala Gly Ser Val Leu Gly Asn Gly
65                  70                  75                  80

Ser Thr Ala Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
                100                 105                 110

Thr Leu Phe Ser Gln Ala Tyr Ser Ala Gly Ala Arg Ile His Thr Asn
        115                 120                 125

Ser Trp Gly Thr Ala Val Asn Gly Ala Tyr Thr Thr Asp Ser Arg Asn
130                 135                 140

Val Asp Asp Tyr Val Arg Lys Asn Asp Met Thr Ile Leu Phe Ala Ala
145                 150                 155                 160

Gly Asn Glu Gly Pro Gly Val Gly Thr Ile Ser Ala Pro Gly Thr Ala
                165                 170                 175

Lys Asn Ala Ile Thr Val Gly Ala Thr Glu Asn Leu Arg Pro Ser Phe
                180                 185                 190

Gly Ser Gln Ala Asp Asn Ile Asn His Val Ala Gln Phe Ser Ser Arg
        195                 200                 205

Gly Pro Thr Lys Asp Gly Arg Ile Lys Pro Asp Val Met Ala Pro Gly
        210                 215                 220

Thr Phe Ile Leu Ser Ala Arg Ser Ser Leu Ala Pro Asp Ser Ser Phe
225                 230                 235                 240
```

```
Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Ile Lys Asn Arg Gly Ile Thr Pro Lys Pro Ser Leu Leu Lys Ala Ala
        275                 280                 285

Leu Ile Ala Gly Ala Thr Asp Ile Gly Leu Gly Tyr Pro Asn Gly Asn
    290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Ser Ala Ser Val Thr Leu Val Asn Asp Leu
        355                 360                 365

Asn Leu Val Ile Thr Ala Pro Asn Gly Thr Gln Tyr Val Gly Asn Asp
    370                 375                 380

Phe Thr Ala Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
            420                 425                 430

Val Asn

<210> SEQ ID NO 4
<211> LENGTH: 434
<212> TYPE: PRT
<213> ORGANISM: Bacillus sp. KSM-KP43
<220> FEATURE:
<223> OTHER INFORMATION: Valiant

<400> SEQUENCE: 4

Asn Asp Val Ala Arg Gly Ile Val Lys Ala Asp Val Ala Gln Ser Val
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Pro Asn Gly His Gly Thr His Val Ala Gly Ser Val Leu Gly Asn Gly
65                  70                  75                  80

Ser Glu Ala Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
        115                 120                 125

Ser Trp Gly Thr Ala Val Asn Gly Ala Tyr Thr Thr Asp Ser Arg Asn
    130                 135                 140

Val Asp Asp Tyr Val Arg Lys Asn Asp Met Thr Ile Leu Phe Ala Ala
145                 150                 155                 160
```

```
Gly Asn Glu Gly Pro Gly Val Gly Thr Ile Ser Ala Pro Gly Thr Ala
                165                 170                 175

Lys Asn Ala Ile Thr Val Gly Thr Glu Asn Leu Arg Pro Ser Phe
            180                 185                 190

Gly Ser Cys Ala Asp Asn Ile Asn His Val Ala Cys Phe Ser Ser Arg
            195                 200                 205

Gly Pro Thr Lys Asp Gly Arg Ile Lys Pro Asp Val Met Ala Pro Gly
        210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
                260                 265                 270

Ile Lys Asn Arg Gly Ile Thr Pro Lys Pro Ser Leu Leu Lys Ala Ala
            275                 280                 285

Leu Ile Ala Gly Ala Thr Asp Ile Gly Leu Gly Tyr Pro Asn Gly Asn
            290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
                340                 345                 350

Asp Ala Pro Ala Ser Thr Ser Ala Ser Val Thr Leu Val Asn Asp Leu
            355                 360                 365

Asn Leu Val Ile Thr Ala Pro Asn Gly Thr Gln Tyr Val Gly Asn Asp
        370                 375                 380

Phe Thr Ala Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
                420                 425                 430

Val Asn

<210> SEQ ID NO 5
<211> LENGTH: 434
<212> TYPE: PRT
<213> ORGANISM: Bacillus sp. KSM-KP43
<220> FEATURE:
<223> OTHER INFORMATION: Valiant

<400> SEQUENCE: 5

Asn Asp Val Ala Arg Gly Ile Val Lys Ala Asp Val Ala Gln Ser Val
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
        50                  55                  60

Pro Asn Gly His Gly Thr His Val Ala Gly Ser Val Leu Gly Asn Gly
65                  70                  75                  80

Ser Glu Ala Lys Gly Met Ala Pro Gln Ala Asn Leu Val Phe Gln Ser
```

```
                    85                  90                  95
Ile Met Asp Ser Gly Gly Gly Leu Gly Gly Leu Pro Ser Asn Leu Gln
                100                 105                 110

Thr Leu Phe Ser Gln Ala Tyr Ser Ala Gly Ala Arg Ile His Thr Asn
            115                 120                 125

Ser Trp Gly Thr Ala Val Asn Gly Ala Tyr Thr Thr Asp Ser Arg Asn
        130                 135                 140

Val Asp Asp Tyr Val Arg Lys Asn Asp Met Thr Ile Leu Phe Ala Ala
145                 150                 155                 160

Gly Asn Glu Gly Pro Gly Val Gly Thr Ile Ser Ala Pro Gly Thr Ala
                165                 170                 175

Lys Asn Ala Ile Thr Val Gly Ala Thr Glu Asn Leu Arg Pro Ser Phe
                180                 185                 190

Gly Ser Cys Ala Asp Asn Ile Asn Asp Val Ala Cys Phe Ser Ser Arg
            195                 200                 205

Gly Pro Thr Lys Asp Gly Arg Ile Lys Pro Asp Val Met Ala Pro Gly
        210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
                260                 265                 270

Ile Lys Asn Arg Gly Ile Thr Pro Lys Pro Ser Leu Leu Lys Ala Ala
            275                 280                 285

Leu Ile Ala Gly Ala Thr Asp Ile Gly Leu Gly Tyr Pro Asn Glu Ala
        290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
                340                 345                 350

Asp Ala Pro Ala Ser Thr Ser Ala Ser Val Thr Leu Val Asn Asp Leu
            355                 360                 365

Asn Leu Val Ile Thr Ala Pro Asn Gly Thr Gln Tyr Val Gly Asn Asp
        370                 375                 380

Phe Thr Ala Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
                420                 425                 430

Val Asn

<210> SEQ ID NO 6
<211> LENGTH: 434
<212> TYPE: PRT
<213> ORGANISM: Bacillus sp. KSM-KP43
<220> FEATURE:
<223> OTHER INFORMATION: Valiant

<400> SEQUENCE: 6

Asn Asp Val Ala Arg Gly Ile Val Lys Ala Asp Val Ala Gln Asp Val
1               5                   10                  15
```

-continued

```
Tyr Gly Leu Tyr Gly Gln Gly Gln Ile Val Ala Val Ala Asp Thr Gly
         20                  25                  30

Leu Asp Thr Gly Arg Asn Asp Ser Ser Met His Glu Ala Phe Arg Gly
         35                  40                  45

Lys Ile Thr Ala Leu Tyr Ala Leu Gly Arg Thr Asn Asn Ala Asn Asp
         50                  55                  60

Pro Asn Gly His Gly Thr His Val Ala Gly Ser Val Leu Gly Asn Gly
 65                  70                  75                  80

Ser Glu Ala Lys Gly Met Ala Pro Gln Ala Asn Leu Val Phe Gln Ser
                 85                  90                  95

Ile Met Asp Ser Gly Gly Gly Leu Gly Gly Leu Pro Ser Asn Leu Gln
                100                 105                 110

Thr Leu Phe Ser Gln Ala Tyr Ser Ala Gly Ala Arg Ile His Thr Asn
            115                 120                 125

Ser Trp Gly Thr Ala Val Asn Gly Ala Tyr Thr Thr Asp Ser Arg Asn
130                 135                 140

Val Asp Asp Tyr Val Arg Lys Asn Asp Met Thr Ile Leu Phe Ala Ala
145                 150                 155                 160

Gly Asn Glu Gly Pro Gly Val Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Cys Ala Asp Asn Ile Asn Asp Val Ala Cys Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Ile Lys Asn Arg Gly Ile Thr Pro Lys Pro Ser Leu Leu Lys Ala Ala
        275                 280                 285

Leu Ile Ala Gly Ala Thr Asp Ile Gly Leu Gly Tyr Pro Asn Glu Ala
    290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Ser Ala Ser Val Thr Leu Val Asn Asp Leu
        355                 360                 365

Asn Leu Val Ile Thr Ala Pro Asn Gly Thr Gln Tyr Val Gly Asn Asp
    370                 375                 380

Phe Thr Ala Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
            420                 425                 430
```

Val Asn

<210> SEQ ID NO 7
<211> LENGTH: 434
<212> TYPE: PRT
<213> ORGANISM: Bacillus sp. KSM-KP43
<220> FEATURE:
<223> OTHER INFORMATION: Valiant

<400> SEQUENCE: 7

```
Asn Asp Val Ala Arg Gly Ile Val Lys Ala Asp Val Ala Gln Glu Val
1               5                   10                  15

Tyr Gly Leu Tyr Gly Gln Gly Gln Ile Val Ala Val Ala Asp Thr Gly
            20                  25                  30

Leu Asp Thr Gly Arg Asn Asp Ser Ser Met His Glu Ala Phe Arg Gly
        35                  40                  45

Lys Ile Thr Ala Leu Tyr Ala Leu Gly Arg Thr Asn Asn Ala Asn Asp
    50                  55                  60

Pro Asn Gly His Gly Thr His Val Ala Gly Ser Val Leu Gly Asn Gly
65                  70                  75                  80

Ser Glu Ala Lys Gly Met Ala Pro Gln Ala Asn Leu Val Phe Gln Ser
                85                  90                  95

Ile Met Asp Ser Gly Gly Gly Leu Gly Gly Leu Pro Ser Asn Leu Gln
            100                 105                 110

Thr Leu Phe Ser Gln Ala Tyr Ser Ala Gly Ala Arg Ile His Thr Asn
        115                 120                 125

Ser Trp Gly Thr Ala Val Asn Gly Ala Tyr Thr Thr Asp Ser Arg Asn
    130                 135                 140

Val Asp Asp Tyr Val Arg Lys Asn Asp Met Thr Ile Leu Phe Ala Ala
145                 150                 155                 160

Gly Asn Glu Gly Pro Gly Val Gly Thr Ile Ser Ala Pro Gly Thr Ala
                165                 170                 175

Lys Asn Ala Ile Thr Val Gly Ala Thr Glu Asn Leu Arg Pro Ser Phe
            180                 185                 190

Gly Ser Cys Ala Asp Asn Ile Asn Asp Val Ala Cys Phe Ser Ser Arg
        195                 200                 205

Gly Pro Thr Lys Asp Gly Arg Ile Lys Pro Asp Val Met Ala Pro Gly
    210                 215                 220

Thr Phe Ile Leu Ser Ala Arg Ser Ser Leu Ala Pro Asp Ser Ser Phe
225                 230                 235                 240

Trp Ala Asn His Asp Ser Lys Tyr Ala Tyr Met Gly Gly Thr Ser Met
                245                 250                 255

Ala Thr Pro Ile Val Ala Gly Asn Val Ala Gln Leu Arg Glu His Phe
            260                 265                 270

Ile Lys Asn Arg Gly Ile Thr Pro Lys Pro Ser Leu Leu Lys Ala Ala
        275                 280                 285

Leu Ile Ala Gly Ala Thr Asp Ile Gly Leu Gly Tyr Pro Asn Glu Ala
    290                 295                 300

Gln Gly Trp Gly Arg Val Thr Leu Asp Lys Ser Leu Asn Val Ala Tyr
305                 310                 315                 320

Val Asn Glu Ser Ser Ser Leu Ser Thr Ser Gln Lys Ala Thr Tyr Ser
                325                 330                 335

Phe Thr Ala Thr Ala Gly Lys Pro Leu Lys Ile Ser Leu Val Trp Ser
            340                 345                 350

Asp Ala Pro Ala Ser Thr Ser Ala Ser Val Thr Leu Val Asn Asp Leu
```

```
                     355                 360                 365
Asn Leu Val Ile Thr Ala Pro Asn Gly Thr Gln Tyr Val Gly Asn Asp
    370                 375                 380

Phe Thr Ala Pro Tyr Asn Asp Asn Trp Asp Gly Arg Asn Asn Val Glu
385                 390                 395                 400

Asn Val Phe Ile Asn Ala Pro Gln Ser Gly Thr Tyr Thr Ile Glu Val
                405                 410                 415

Gln Ala Tyr Asn Val Pro Val Gly Pro Gln Thr Phe Ser Leu Ala Ile
        420                 425                 430

Val Asn

<210> SEQ ID NO 8
<211> LENGTH: 24
<212> TYPE: DNA
<213> ORGANISM: Artificial
<220> FEATURE:
<223> OTHER INFORMATION: Primer 303_R

<400> SEQUENCE: 8
gttcgggtag ccaaggccga tgtc                                          24

<210> SEQ ID NO 9
<211> LENGTH: 35
<212> TYPE: DNA
<213> ORGANISM: Artificial
<220> FEATURE:
<223> OTHER INFORMATION: Primer 303A_F

<400> SEQUENCE: 9
cttggctacc cgaacgcaaa ccaaggatgg ggacg                              35

<210> SEQ ID NO 10
<211> LENGTH: 35
<212> TYPE: DNA
<213> ORGANISM: Artificial
<220> FEATURE:
<223> OTHER INFORMATION: Primer 303C_F

<400> SEQUENCE: 10
cttggctacc cgaactgcaa ccaaggatgg ggacg                              35

<210> SEQ ID NO 11
<211> LENGTH: 35
<212> TYPE: DNA
<213> ORGANISM: Artificial
<220> FEATURE:
<223> OTHER INFORMATION: Primer 303D_F

<400> SEQUENCE: 11
cttggctacc cgaacgataa ccaaggatgg ggacg                              35

<210> SEQ ID NO 12
<211> LENGTH: 35
<212> TYPE: DNA
<213> ORGANISM: Artificial
<220> FEATURE:
<223> OTHER INFORMATION: Primer 303E_F

<400> SEQUENCE: 12
cttggctacc cgaacgaaaa ccaaggatgg ggacg                              35

<210> SEQ ID NO 13
<211> LENGTH: 35
```

```
<212> TYPE: DNA
<213> ORGANISM: Artificial
<220> FEATURE:
<223> OTHER INFORMATION: Primer 303F_F

<400> SEQUENCE: 13
cttggctacc cgaacttcaa ccaaggatgg ggacg                          35

<210> SEQ ID NO 14
<211> LENGTH: 35
<212> TYPE: DNA
<213> ORGANISM: Artificial
<220> FEATURE:
<223> OTHER INFORMATION: Primer 303H_F

<400> SEQUENCE: 14
cttggctacc cgaaccataa ccaaggatgg ggacg                          35

<210> SEQ ID NO 15
<211> LENGTH: 35
<212> TYPE: DNA
<213> ORGANISM: Artificial
<220> FEATURE:
<223> OTHER INFORMATION: Primer 303I_F

<400> SEQUENCE: 15
cttggctacc cgaacattaa ccaaggatgg ggacg                          35

<210> SEQ ID NO 16
<211> LENGTH: 35
<212> TYPE: DNA
<213> ORGANISM: Artificial
<220> FEATURE:
<223> OTHER INFORMATION: Primer 303K_F

<400> SEQUENCE: 16
cttggctacc cgaacaaaaa ccaaggatgg ggacg                          35

<210> SEQ ID NO 17
<211> LENGTH: 35
<212> TYPE: DNA
<213> ORGANISM: Artificial
<220> FEATURE:
<223> OTHER INFORMATION: Primer 303L_F

<400> SEQUENCE: 17
cttggctacc cgaaccttaa ccaaggatgg ggacg                          35

<210> SEQ ID NO 18
<211> LENGTH: 35
<212> TYPE: DNA
<213> ORGANISM: Artificial
<220> FEATURE:
<223> OTHER INFORMATION: Primer 303M_F

<400> SEQUENCE: 18
cttggctacc cgaacatgaa ccaaggatgg ggacg                          35

<210> SEQ ID NO 19
<211> LENGTH: 35
<212> TYPE: DNA
<213> ORGANISM: Artificial
<220> FEATURE:
<223> OTHER INFORMATION: Primer 303N_F

<400> SEQUENCE: 19
```

-continued

```
cttggctacc cgaacaataa ccaaggatgg ggacg                          35

<210> SEQ ID NO 20
<211> LENGTH: 35
<212> TYPE: DNA
<213> ORGANISM: Artificial
<220> FEATURE:
<223> OTHER INFORMATION: Primer 303P_F

<400> SEQUENCE: 20
cttggctacc cgaacccaaa ccaaggatgg ggacg                          35

<210> SEQ ID NO 21
<211> LENGTH: 35
<212> TYPE: DNA
<213> ORGANISM: Artificial
<220> FEATURE:
<223> OTHER INFORMATION: Primer 303Q_F

<400> SEQUENCE: 21
cttggctacc cgaaccagaa ccaaggatgg ggacg                          35

<210> SEQ ID NO 22
<211> LENGTH: 35
<212> TYPE: DNA
<213> ORGANISM: Artificial
<220> FEATURE:
<223> OTHER INFORMATION: Primer 303R_F

<400> SEQUENCE: 22
cttggctacc cgaacagaaa ccaaggatgg ggacg                          35

<210> SEQ ID NO 23
<211> LENGTH: 35
<212> TYPE: DNA
<213> ORGANISM: Artificial
<220> FEATURE:
<223> OTHER INFORMATION: Primer 303S_F

<400> SEQUENCE: 23
cttggctacc cgaactccaa ccaaggatgg ggacg                          35

<210> SEQ ID NO 24
<211> LENGTH: 35
<212> TYPE: DNA
<213> ORGANISM: Artificial
<220> FEATURE:
<223> OTHER INFORMATION: Primer 303T_F

<400> SEQUENCE: 24
cttggctacc cgaacacaaa ccaaggatgg ggacg                          35

<210> SEQ ID NO 25
<211> LENGTH: 35
<212> TYPE: DNA
<213> ORGANISM: Artificial
<220> FEATURE:
<223> OTHER INFORMATION: Primer 303V_F

<400> SEQUENCE: 25
cttggctacc cgaacgtgaa ccaaggatgg ggacg                          35

<210> SEQ ID NO 26
<211> LENGTH: 35
<212> TYPE: DNA
<213> ORGANISM: Artificial
```

```
<220> FEATURE:
<223> OTHER INFORMATION: Primer 303W_F

<400> SEQUENCE: 26
cttggctacc cgaactggaa ccaaggatgg ggacg                              35

<210> SEQ ID NO 27
<211> LENGTH: 35
<212> TYPE: DNA
<213> ORGANISM: Artificial
<220> FEATURE:
<223> OTHER INFORMATION: Primer 303Y_F

<400> SEQUENCE: 27
cttggctacc cgaactataa ccaaggatgg ggacg                              35

<210> SEQ ID NO 28
<211> LENGTH: 35
<212> TYPE: DNA
<213> ORGANISM: Artificial
<220> FEATURE:
<223> OTHER INFORMATION: Primer 303E/304A_F

<400> SEQUENCE: 28
cttggctacc cgaacgaagc acaaggatgg ggacg                              35

<210> SEQ ID NO 29
<211> LENGTH: 24
<212> TYPE: DNA
<213> ORGANISM: Artificial
<220> FEATURE:
<223> OTHER INFORMATION: Primer 15_R

<400> SEQUENCE: 29
ctgagccaca tccgctttga caat                                         24

<210> SEQ ID NO 30
<211> LENGTH: 35
<212> TYPE: DNA
<213> ORGANISM: Artificial
<220> FEATURE:
<223> OTHER INFORMATION: Primer 15D_F

<400> SEQUENCE: 30
gcggatgtgg ctcaggatgt gtacgggttg tatgg                             35

<210> SEQ ID NO 31
<211> LENGTH: 35
<212> TYPE: DNA
<213> ORGANISM: Artificial
<220> FEATURE:
<223> OTHER INFORMATION: Primer 15E_F

<400> SEQUENCE: 31
gcggatgtgg ctcaggaagt gtacgggttg tatgg                             35

<210> SEQ ID NO 32
<211> LENGTH: 24
<212> TYPE: DNA
<213> ORGANISM: Artificial
<220> FEATURE:
<223> OTHER INFORMATION: Primer 201_R

<400> SEQUENCE: 32
gttgatattg tccgcgcaag accc                                         24
```

<210> SEQ ID NO 33
<211> LENGTH: 35
<212> TYPE: DNA
<213> ORGANISM: Artificial
<220> FEATURE:
<223> OTHER INFORMATION: Primer 201D_F

<400> SEQUENCE: 33
gcggacaata tcaacgatgt ggcatgcttc tcttc           35

<210> SEQ ID NO 34
<211> LENGTH: 24
<212> TYPE: DNA
<213> ORGANISM: Artificial
<220> FEATURE:
<223> OTHER INFORMATION: Primer 201D/202_R

<400> SEQUENCE: 34
atcgttgata ttgtccgcgc aaga           24

<210> SEQ ID NO 35
<211> LENGTH: 35
<212> TYPE: DNA
<213> ORGANISM: Artificial
<220> FEATURE:
<223> OTHER INFORMATION: Primer 201D/202E_F

<400> SEQUENCE: 35
gacaatatca acgatgaagc atgcttctct tcacg           35

<210> SEQ ID NO 36
<211> LENGTH: 24
<212> TYPE: DNA
<213> ORGANISM: Artificial
<220> FEATURE:
<223> OTHER INFORMATION: Primer 303N/304_R

<400> SEQUENCE: 36
ctggttcggg tagccaaggc cgat           24

<210> SEQ ID NO 37
<211> LENGTH: 35
<212> TYPE: DNA
<213> ORGANISM: Artificial
<220> FEATURE:
<223> OTHER INFORMATION: Primer 303N/304A_F

<400> SEQUENCE: 37
ggctacccga accaggcaca aggatgggga cgagt           35

<210> SEQ ID NO 38
<211> LENGTH: 24
<212> TYPE: DNA
<213> ORGANISM: Artificial
<220> FEATURE:
<223> OTHER INFORMATION: Primer 195_R

<400> SEQUENCE: 38
agacccaaag cttgggcgga ggtt           24

<210> SEQ ID NO 39
<211> LENGTH: 35
<212> TYPE: DNA
<213> ORGANISM: Artificial
<220> FEATURE:
<223> OTHER INFORMATION: Primer 201D/195Q_F

```
<400> SEQUENCE: 39
ccaagctttg ggtctcaggc ggacaatatc aacga                              35

<210> SEQ ID NO 40
<211> LENGTH: 35
<212> TYPE: DNA
<213> ORGANISM: Artificial
<220> FEATURE:
<223> OTHER INFORMATION: Primer 201D/195M_F

<400> SEQUENCE: 40
ccaagctttg ggtctatggc ggacaatatc aacga                              35

<210> SEQ ID NO 41
<211> LENGTH: 24
<212> TYPE: DNA
<213> ORGANISM: Artificial
<220> FEATURE:
<223> OTHER INFORMATION: Primer 201D/204_R

<400> SEQUENCE: 41
tgccacatcg ttgatattgt ccgc                                          24

<210> SEQ ID NO 42
<211> LENGTH: 35
<212> TYPE: DNA
<213> ORGANISM: Artificial
<220> FEATURE:
<223> OTHER INFORMATION: Primer 201D/204Q_F

<400> SEQUENCE: 42
atcaacgatg tggcacagtt ctcttcacgt gggcc                              35
```

MUTANT PROTEASE

FIELD OF THE INVENTION

The present invention relates to a mutant protease.

BACKGROUND OF THE INVENTION

Detergents can be classified into a powder detergent and a liquid detergent, based on the form thereof. A liquid detergent is excellent in terms of solubility, in comparison to a powder detergent. Also, a liquid detergent is advantageous in that an undiluted detergent can be directly applied to stains. On the other hand, in the case of such a liquid detergent, since an enzyme such as a protease must be preserved at ordinary temperature in the liquid, it has technical difficulty in terms of stable preservation of the enzyme, differing from a powder detergent. Further, since a liquid detergent contains a surfactant, a fatty acid, a solvent, a chelating agent, or the like, it imposes extremely strict conditions on the enzyme.

Since the pH of powder detergent is generally on the alkaline side, a protease having an optimum pH on the alkaline side has been developed as a detergent protease. For examples, Patent Literature 1 discloses a protease with a molecular weight of approximately 43,000, which has a washing performance on composite stains containing lipids as well as proteins. Further, Patent Literatures 2 to 7 disclose a mutant protease obtained by introducing a mutation into a protease so as to improve specific activity, stability, heat resistance, solubility in a liquid detergent, or the like.

Meanwhile, a liquid detergent in recent years tends to have a broader range of condition of composition or pH in order to impart various functions. For example, in some cases, a cationic surfactant is blended in a liquid detergent in order to impart antibacterial property to washed clothes. In that case, it is desirable to make the pH of the liquid detergent weakly acidic or strongly acidic in order to reduce the smell generated from the liquid detergent itself containing the cationic surfactant (see, Patent Literature 8). However, the above described detergent protease has an optimum pH on the alkaline side and is unstable in an acidic liquid detergent.

(Patent Literature 1) WO 99/18218
(Patent Literature 2) JP-A-2004-305175
(Patent Literature 3) JP-A-2010-273672
(Patent Literature 4) JP-A-2010-273673
(Patent Literature 5) JP-A-2011-200249
(Patent Literature 6) JP-A-2013-233141
(Patent Literature 7) JP-A-2017-221188
(Patent Literature 8) JP-A-2017-008303

SUMMARY OF THE INVENTION

In one aspect, the present invention provides a mutant protease that consists of an amino acid sequence having an identity of at least 90% with the amino acid sequence as shown in SEQ ID NO:2 and that has an amino acid residue selected from the group consisting of aspartic acid, glutamic acid, phenylalanine, histidine, isoleucine, methionine, asparagine, proline, glutamine, threonine, valine, tryptophan, and tyrosine at a position corresponding to position 303 of the amino acid sequence as shown in SEQ ID NO:2.

In another aspect, the present invention provides a polynucleotide encoding the above described mutant protease.

In another aspect, the present invention provides a vector comprising the above described polynucleotide.

In another aspect, the present invention provides a transformant comprising the above described polynucleotide or the above described vector.

In another aspect, the present invention provides a method for producing a mutant protease, using the above described transformant.

In a further aspect, the present invention provides a detergent composition comprising the above described mutant protease.

In a further aspect, the present invention provides a method for producing a mutant protease, comprising substituting the amino acid residue at a position corresponding to position 303 of the amino acid sequence as shown in SEQ ID NO:2 with an amino acid residue selected from the group consisting of aspartic acid, glutamic acid, phenylalanine, histidine, isoleucine, methionine, asparagine, proline, glutamine, threonine, valine, tryptophan, and tyrosine in the amino acid sequence as shown in SEQ ID NO:2 or an amino acid sequence having an identity of at least 90% therewith.

In a further aspect, the present invention provides a method for improving stability of protease under acidic condition, comprising substituting the amino acid residue at a position corresponding to position 303 of the amino acid sequence as shown in SEQ ID NO:2 with an amino acid residue selected from the group consisting of aspartic acid, glutamic acid, phenylalanine, histidine, isoleucine, methionine, asparagine, proline, glutamine, threonine, valine, tryptophan, and tyrosine in the amino acid sequence as shown in SEQ ID NO:2 or an amino acid sequence having an identity of at least 90% therewith.

DETAILED DESCRIPTION OF THE INVENTION

In the present description, the term "amino acid residue" refers to 20 types of amino acid residues constituting a protein, namely, alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

In the present description, "identity of at least 90%" with respect to an amino acid sequence or nucleotide sequence refers to identity of 90% or more, preferably 95% or more, more preferably 96% or more, further preferably 97% or more, further preferably 98% or more, further preferably 99% or more.

In the present description, an identity between nucleotide sequences or between amino acid sequences can be calculated according to a Lipman-Pearson method (Science, 1985, 227: 1435-41). Specifically, by employing the homology analysis (Search homology) program of the gene information processing software Genetyx-Win (Ver. 5.1.1; Software Development), such an identity can be calculated by performing an analysis, setting Unit size to compare (ktup) at 2.

In the present description, the "amino acid sequence in which one or more amino acids are deleted, inserted, substituted or added" may be an amino acid sequence in which 1 or more and 20 or less, preferably 1 or more and 10 or less, more preferably 1 or more and 5 or less, further preferably 1 or more and 3 or less amino acids are deleted, inserted, substituted or added. In addition, in the present description, the "nucleotide sequence in which one or more nucleotides are deleted, inserted, substituted or added" may be a nucleotide sequence in which 1 or more and 60 or less, preferably 1 or more and 30 or less, more preferably 1 or more and 15 or less, further preferably 1 or more and 10 or less nucleotides are deleted, inserted, substituted or added. Moreover, in the present description, "addition" of amino acids or nucleotides includes addition of one or more amino acids or nucleotides to one terminus or both termini of the sequence.

In the present description, the "corresponding position" on an amino acid sequence or a nucleotide sequence can be determined by aligning a target sequence and a reference sequence (e.g., the amino acid sequence as shown in SEQ ID NO: 2) such that they give the maximum homology. Alignment of an amino acid sequence or nucleotide sequence can be carried out using a known algorithm, and the procedures thereof are known to a person skilled in the art. For example, the alignment can be carried out using Clustal W Multiple Alignment Program (Thompson, J. D. et al, 1994, Nucleic Acids Res, 22: 4673-4680) with default setting. Otherwise, Clustal W2 or Clustal omega, which is a revision of Clustal W, can also be used. Such Clustal W, Clustal W2, and Clustal omega are available, for example, on the website of European Bioinformatics Institute (EBI [www.ebi.ac.uk]), or the website of DNA Data Bank of Japan (DDBJ [www.ddbj.nig.ac.jp]) handled by National Institute of Genetics. A position of a target sequence aligned to a certain position of a refence sequence by the above described alignment is considered as "corresponding position" to the certain position.

A person skilled in the art can further finely adjust the above obtained alignment of amino acid sequences, so that it can be optimized. Such optimal alignment is preferably determined, while taking into consideration the similarity of amino acid sequences, the frequency of inserted gaps, etc. In this context, the similarity of amino acid sequences means the ratio (%) of the number of the positions, at which identical or analogous amino acid residues are present in two amino acid sequences, relative to the number of full-length amino acid residues, when the two amino acid sequences are aligned to each other. Analogous amino acid residues mean amino acid residues, which have similar properties to each other in polarity and electric charge and cause, what is called, conservative substitution, among 20 types of amino acids constituting a protein. Groups consisting of such analogous amino acid residues are well known to a person skilled in the art, and examples of such groups include: arginine and lysine; glutamic acid and aspartic acid; serine and threonine; glutamine and asparagine; and leucine and isoleucine, but the examples are not limited thereto.

The position of the amino acid residue of a target amino acid sequence, which is aligned to a position corresponding to an arbitrary position of the reference sequence according to the above described alignment, is considered to be the "position corresponding to" the arbitrary position, and the amino acid residue is referred to as the "amino acid residue at a corresponding position."

In the present description, the "parent" polypeptide of a mutant polypeptide means a polypeptide, which is converted to the mutant polypeptide by introducing a certain mutation into the amino acid residue thereof. In other words, the "parent polypeptide" refers to a polypeptide before mutation of the polypeptide mutant. Similarly, the "parent" polynucleotide of a mutant polynucleotide means a polynucleotide which is converted to the mutant polynucleotide by introducing a certain mutation into the nucleotide thereof. In other words, the "parent" polynucleotide refers to a polynucleotide before mutation of the mutant polynucleotide.

In the present description, the "operable linking" of a regulatory region such as promoter to a gene means that the gene is linked to the regulatory region such that the gene can be expressed under the control of the regulatory region. The procedures for "operably linking" of the gene to the regulatory region are well known to a person skilled in the art.

In the present description, the terms "upstream" and "downstream" used regarding a gene mean the upstream and downstream of the gene in the transcription direction, unless otherwise specified. For example, a "gene located downstream of a promoter" means that the gene exists at the 3'side of the promoter in the DNA sense strand, and upstream of a gene refers to the region of the 5'side of the gene in the DNA sense strand.

In the present description, the term "instrinsic" with respect to a function, property or a trait of a cell means that the function, property or trait is present in the wild-type of the cell. In contrast, the term "exogenous" is used to represent that the function, property or trait has been introduced from outside, not originally present in the cell. For example, the "exogenous" gene or polynucleotide is a gene or polynucleotide introduced into the cell from the outside. The exogenous gene or polynucleotide may be derived from a homogenous biological species of the cell into which the gene or polynucleotide are introduced or may be derived from a different biological species (i.e., a heterologous gene or polynucleotide).

The present invention relates to provision of a mutant protease with improved stability under acidic condition.

The present inventors found that the stability of protease KP43 having a molecular weight of 43,000 under acidic condition is improved by substituting the amino acid residue at a specific position in the amino acid sequence thereof with another amino acid residue.

The mutant protease according to the present invention has high protease activity at alkaline pH and can stably retain enzyme activity even under acidic condition. Accordingly, the mutant protease according to the present invention can exert enzyme activity under a wide range of pH condition. The mutant protease according to the present invention can be used as an enzyme to be blended in various detergent compositions having alkaline to weakly acidic property. For example, when the mutant protease according to the present invention is blended in a weakly acidic detergent composition containing a cationic surfactant in order to impart antibacterial property, not only the detergent composition is weakly acidic to thereby hardly generate the smell of the detergent itself due to a cationic surfactant, but also the protease activity is retained stably to thereby have excellent washing performance.

The present invention provides a mutant protease. The mutant protease according to the present invention consists of the amino acid sequence as shown in SEQ ID NO:2 or an amino acid sequence having an identity of at least 90% thereto, in which the amino acid residue at a position corresponding to position 303 in the amino acid sequence as shown in SEQ ID NO:2 is substituted with an amino acid residue selected from the group consisting of aspartic acid, glutamic acid, phenylalanine, histidine, isoleucine, methionine, asparagine, proline, glutamine, threonine, valine, tryptophan, and tyrosine.

Examples of a parent protease of the mutant protease according to the present invention (hereinafter also referred to as the mutant protease according to the present invention) include a protease that consists of the amino acid sequence as shown in SEQ ID NO: 2, and a protease that consists of an amino acid sequence having an identity of at least 90%, with the amino acid sequence as shown in SEQ ID NO: 2. Examples of the protease that consists of the amino acid sequence as shown in SEQ ID NO: 2 include, for example, a protease derived from KP43 [*Bacillus* sp. KSM-KP43 (FERM BP-6532)] (see Patent Literature 1).

Preferred examples of the protease that consists of an amino acid sequence having an identity of at least 90% with the amino acid sequence as shown in SEQ ID NO: 2 include a protease having an identity of 95% or more, preferably 96% or more, more preferably 97% or more, further preferably 98% or more, still further preferably 99% or more, with the amino acid sequence as shown in SEQ ID NO: 2. Another examples of the protease that consists of an amino acid sequence having an identity of at least 90% with the amino acid sequence as shown in SEQ ID NO: 2 include a protease that consists of the amino acid sequence as shown in SEQ ID NO: 2 in which one or more amino acids are deleted, inserted, substituted or added.

Further examples of the protease that consists of an amino acid sequence having an identity of at least 90% with the amino acid sequence as shown in SEQ ID NO: 2 include protease KP9860 (derived from *Bacillus* sp. KSM-KP9860 (FERM BP-6534); WO99/18218; GenBank Accession No. AB046403] and protease 9865 [derived from *Bacillus* sp. KSM-9865 (FERM P-18566); GenBank Accession No. AB084155].

The protease that consists of an amino acid sequence having an identity of at least 90% with the amino acid sequence as shown in SEQ ID NO: 2, which is used as a parent protease in the present invention, may be a mutant protease derived from the protease that consists of the amino acid sequence as shown in SEQ ID NO: 2. Examples of the mutant protease include mutant protease obtained by introducing one or more of the mutations described in JP-A-2002-218989, JP-A-2002-306176, JP-A-2004-000122, JP-A-2004-305176, JP-A-2006-129865, JP-A-2007-061101, JP-A-2008-212084, JP-A-2009-034062, JP-A-2010-273672, JP-A-2010-273673, JP-A-2011-200249, JP-A-2012-228216, JP-A-2013-233141 and JP-A-2017-221188, into the above-described KP-43 strain-derived protease.

Preferred examples of the above described mutant protease used as a parent protease in the present invention include a mutant protease that consists of the amino acid sequence as shown in SEQ ID NO: 2 and has one or more mutations selected from the group consisting of the following (a) to (dv):

(a) substitution of G at position 6 or at a position corresponding thereto with S, T, C, Q, Y, R, K, H, A, V, L, I, M, W or F;
(b) substitution of K at position 9 or at a position corresponding thereto with Q;
(c) substitution of D at position 11 or at a position corresponding thereto with G, S or N;
(d) substitution of S at position 15 or at a position corresponding thereto with H, C, Q, D, E, R, A, V, M, W or F;
(e) substitution of S at position 16 or at a position corresponding thereto with 2, Q, V, C, Y, D, E, R, K, H, L, I, M, W or F;
(f) substitution of Y at position 20 or at a position corresponding thereto with F or A;
(g) substitution of Q at position 22 or at a position corresponding thereto with W;
(h) substitution of G at position 23 or at a position corresponding thereto with N;
(i) substitution of R at position 37 or at a position corresponding thereto with Z;
(j) substitution of S at position 40 or at a position corresponding thereto with V, L, I, W or F;
(k) substitution of S at position 41 or at a position corresponding thereto with I;
(l) substitution of F at position 46 or at a position corresponding thereto with S, T, C, N, Q, Y, E, K, H, A, V, L, I, M or W;
(m) substitution of K at position 49 or at a position corresponding thereto with Q;
(n) substitution of A at position 52 or at a position corresponding thereto with G or S;
(o) substitution of L at position 53 or at a position corresponding thereto with A, V or I;
(p) substitution of Y at position 54 or at a position corresponding thereto with G, S, T, C, N, Q, D, E, R, H, A, V, M, W, F or P;
(q) substitution of L at position 56 or at a position corresponding thereto with V;
(r) substitution of G at position 57 or at a position corresponding thereto with S, T, C, Q, D, E, R, K, H, A, V, L, I, M, W, F or P;
(s) substitution of T at position 59 or at a position corresponding thereto with V, L, I, M, W or F;
(t) substitution of N at position 60 or at a position corresponding thereto with V, L, I, W or F;
(u) substitution of N at position 63 or at a position corresponding thereto with S, D or L;
(v) substitution of T at position 65 or at a position corresponding thereto with W or P;
(w) substitution of N at position 66 or at a position corresponding thereto with G, S, T, C, Q, D, E, H, A, V, L, I, M or W;
(x) substitution of G at position 80 or at a position corresponding thereto with H or A;
(y) substitution of S at position 81 or at a position corresponding thereto with Q, Y, L, I, W or F;
(z) substitution of T at position 82 or at a position corresponding thereto with G, S, C, Q, D, E, R, K, H, A or M;
(aa) substitution of N at position 83 or at a position corresponding thereto with S, C or A;
(ab) substitution of K at position 84 or at a position corresponding thereto with R;
(ac) substitution of Q at position 89 or at a position corresponding thereto with 4;
(ad) substitution of N at position 91 or at a position corresponding thereto with C;
(ae) substitution of S at position 100 or at a position corresponding thereto with L, I, W or F;
(af) substitution of G at position 101 or at a position corresponding thereto with S, T, C, N, Q, Y, D, E, R, K, H, A, V, L, I, M, W, F or P;
(ag) substitution of G at position 102 or at a position corresponding thereto with 3, T, C, Q, Y, D, E, R, K, H, A, V, L, T, M, W, F or P;
(ah) substitution of G at position 103 or at a position corresponding thereto with S, T, C, Q, Y, D, E, R, K, H, A, V, L, I, M, W, F or P;
(ai) substitution of L at position 104 or at a position corresponding thereto with S, T, C, Q, Y, D, E, R, K, H, A, V, L, I, M, W, F or P;
(aj) substitution of G at position 105 or at a position corresponding thereto with S, T, C, Q, Y, D, E, R, K, H, A, V, L, I, M, W, F or P;

(ak) substitution of G at position 106 or at a position corresponding thereto with S, T, C, Q, Y, D, E, R, K, H, A, V, L, I, M, W, F or P;
(al) substitution of L at position 107 or at a position corresponding thereto with S, R, K or A;
(am) substitution of S at position 109 or at a position corresponding thereto with L, I or F;
(an) substitution of T at position 113 or at a position corresponding thereto with L or W;
(ao) substitution of Y at position 119 or at a position corresponding thereto with G, S, T, C, N, Q, D, E, R, K, H, A, V, M, W, F or P;
(ap) substitution of S at position 120 or at a position corresponding thereto with Y, R, I, W or F;
(aq) substitution of R at position 124 or at a position corresponding thereto with K or A;
(ar) substitution of A at position 132 or at a position corresponding thereto with S, T, N, Q, D, I or M;
(as) substitution of A at position 133 or at a position corresponding thereto with G, S, T, C, N, Q, D, E, R, K, H, V, L, I, M, W, F or P;
(at) substitution of V at position 134 or at a position corresponding thereto with G, S, T or A;
(au) insertion of G, S, T, N, Q, Y, R, K, H, A, L, I, M or W between the position 133 or a position corresponding thereto and the position 134 or a position corresponding thereto;
(av) substitution of N at position 135 or at a position corresponding thereto with R, A, L or M;
(aw) substitution of G at position 136 or at a position corresponding thereto with S, T, C, Q, Y, D, E, R, K, H, A, V, L, I, M, W, F or P;
(ax) substitution of Y at position 138 or at a position corresponding thereto with G, S, C, N, Q, D, E, R, K, H, A, V, M, W, F or P;
(ay) substitution of T at position 140 or at a position corresponding thereto with L, W or F;
(az) substitution of Y at position 148 or at a position corresponding thereto with G, S, T, C, N, Q, D, E, R, K, H, A, M, W, F or P;
(ba) substitution of K at position 151 or at a position corresponding thereto with F;
(bb) substitution of E at position 163 or at a position corresponding thereto with S, T, N, Q, D, K, H, V, L, I or F;
(bc) substitution of N at position 166 or at a position corresponding thereto with G, V, L, I, W or F;
(bd) substitution of G at position 167 or at a position corresponding thereto with V;
(be) substitution of I at position 170 or at a position corresponding thereto with V or L;
(bf) substitution of S at position 171 or at a position corresponding thereto with G, T, E or A;
(bg) substitution of N at position 187 or at a position corresponding thereto with S;
(bh) substitution of S at position 191 or at a position corresponding thereto with V, L, I, W or F;
(bi) substitution of G at position 193 or at a position corresponding thereto with S, T, C, Q, Y, D, E, R, K, H, A, V, L, I, M, W, F or P;
(bj) substitution of S at position 194 or at a position corresponding thereto with Y, R or K;
(bk) substitution of Y at position 195 or at a position corresponding thereto with G, S, T, C, N, Q, D, E, R, K, H, A, V, L, I, M, W, F or P;
(bl) substitution of N at position 200 or at a position corresponding thereto with W;
(bm) substation of H at position 201 or at a position corresponding thereto with D, E or Q;
(bn) substitution of V at position 202 or a position corresponding thereto with E;
(bo) substitution of Q at position 204 or at a position corresponding thereto with 3, T, C, N, D, E, R, K, H, V, L, I, M, W or P;
(bp) substitution of F at position 205 or at a position corresponding thereto with 3, T, C, N, Q, Y, E, K, H, A, V, L, I, M or W;
(bq) substitution of K at position 212 or at a position corresponding thereto with N, Q, R, V, L or W;
(br) substitution of F at position 226 or at a position corresponding thereto with Y;
(bs) substitution of S at position 233 or at a position corresponding thereto with L, I or W;
(bt) substitution of D at position 237 or at a position corresponding thereto with N;
(bu) substitution of S at position 238 or at a position corresponding thereto with L;
(bv) substitution of N at position 243 or at a position corresponding thereto with Y, L or I;
(bw) substitution of D at position 245 or at a position corresponding thereto with N;
(bx) substitution of S at position 246 or at a position corresponding thereto with Y, V, L, W or F;
(by) substitution of K at position 247 or at a position corresponding thereto with S, T, C, N, Q, E, H, A, V, L, I, M, W or F;
(bz) substitution of Y at position 248 or at a position corresponding thereto with F;
(ca) substitution of Y at position 250 or at a position corresponding thereto with F;
(cb) substitution of M at position 251 or at a position corresponding thereto with G, T, N, Q, D, A, V, L or I;
(cc) substitution of M at position 256 or at a position corresponding thereto with S, T, C, Q, Y, D, E, R, K, H, A, V, L, I, W, F or P;
(cd) substitution of A at position 257 or at a position corresponding thereto with V or I;
(ce) substitution of N at position 264 or at a position corresponding thereto with G, S, T, C, Q, D, E, A, V, L, I or M;
(cf) substitution of V at position 273 or at a position corresponding thereto with G, T or I;
(cg) substitution of N at position 275 or at a position corresponding thereto with L, W or F;
(ch) substitution of G at position 277 or at a position corresponding thereto with V, L, I or F;
(ci) substitution of K at position 281 or at a position corresponding thereto with R;
(cj) substitution of A at position 294 or a position corresponding thereto with T;
(ck) substitution of I at position 296 or at a position corresponding thereto with V;
(cl) substitution of G at position 297 or at a position corresponding thereto with L, W or F;
(cm) substitution of N at position 304 or at a position corresponding thereto with S or A;
(cn) substitution of D at position 313 or at a position corresponding thereto with N;
(co) substitution of A at position 319 or at a position corresponding thereto with S, T, C, N, Q, Y, D, E, R, K, H, V, L, I, M, W, F or P;
(cp) substitution of Y at position 320 or at a position corresponding thereto with G, T, V, L, I or F;

(cq) substitution of S at position 326 or at a position corresponding thereto with W;
(cr) substitution of S at position 330 or at a position corresponding thereto with M, W or F;
(cs) substitution of K at position 332 or at a position corresponding thereto with G, T or V;
(ct) substitution of T at position 334 or at a position corresponding thereto with L;
(cu) substitution of Y at position 335 or at a position corresponding thereto with F;
(cv) substitution of F at position 337 or at a position corresponding thereto with G, S, T, C, Q, R, K, H, A or V;
(cw) substitution of G at position 342 or at a position corresponding thereto with S, T, C, Q, Y, D, E, R, K, H, A, V, L, I, M, W, F or P;
(cx) substitution of K at position 343 or at a position corresponding thereto with T;
(cy) substitution of K at position 346 or at a position corresponding thereto with R;
(cz) substitution of S at position 357 or at a position corresponding thereto with L;
(da) substitution of T at position 359 or at a position corresponding thereto with G, S, Q, V, L, I or F;
(db) substitution of S at position 361 or at a position corresponding thereto with V, I or W;
(dc) substitution of D at position 369 or at a position corresponding thereto with N;
(dd) substitution of N at position 376 or at a position corresponding thereto with W;
(de) substitution of T at position 378 or at a position corresponding thereto with L or W;
(df) substitution of Q at position 379 or at a position corresponding thereto with D, E, R or K;
(dg) substitution of Y at position 380 or at a position corresponding thereto with F;
(dh) substitution of F at position 385 or at a position corresponding thereto with Y, M or P;
(di) substitution of T at position 386 or at a position corresponding thereto with A, L, I or M;
(dj) substitution of S at position 387 or at a position corresponding thereto with G, Q, E, R, K, H, A, V, L, I, M, W or F;
(dk) substitution of N at position 390 or at a position corresponding thereto with G, S, T, Y or F;
(dl) substitution of W at position 393 or at a position corresponding thereto with Q;
(dm) substitution of R at position 396 or at a position corresponding thereto with G;
(dn) substitution of F at position 403 or at a position corresponding thereto with T or K;
(do) substitution of N at position 405 or at a position corresponding thereto with D, V, L, I, W, F or P;
(dp) substitution of A at position 406 or at a position corresponding thereto with V, W or F;
(dq) substitution of P at position 407 or at a position corresponding thereto with G or C;
(dr) substitution of Q at position 408 or at a position corresponding thereto with N, Y, I or W;
(ds) substitution of a at position 409 or at a position corresponding thereto with Y or W;
(dt) substitution of T at position 411 or at a position corresponding thereto with A, V, L or P;
(du) substitution of T at position 427 or at a position corresponding thereto with R or V; and
(dv) substitution of V at position 433 or at a position corresponding thereto with L.

The above described mutations (a) to (dv) may be applied alone as a single use of any one, or may also be applied in combination of any two or more. Preferred examples include as follows:
the (ar);
the (bk);
the (bm);
the (cj);
the (cm);
the (dc);
a combination of the (e) and (aa);
a combination of the (bc) and (bd);
a combination of the (bm) and (bn);
a combination of the (bm) and (cm);
a combination of the (bm), (bn) and (cm);
a combination of the (d), (bm) and (cm);
a combination of the (d), (bm), (bn) and (cm);
a combination of the (v), (cf), (da) and (dj);
a combination of the (j), (s), (y), (bh) and (do);
a combination of the (as), (at) and (au);
a combination of the (e), (v), (aa), (bc), (bd), (bk), (cf), (da), (dc) and (dj);
a combination of the (e), (v), (aa), (ar), (bc), (bd), (bk), (cf), (da), (dc) and (dj);
a combination of the (j), (s), (v), (y), (as), (at), (au), (bc), (bd), (bh), (bk), (cf), (da), (dc), (dj) and (do);
a combination of the (v), (aa), (ar), (bc), (bd), (bk), (cf), (da), (dc) and (dj);
a combination of the (v), (as), (at), (au), (bc), (bd), (bk), (cf), (da), (dc) and (dj);
a combination of the (e), (v), (aa), (bc), (bd), (bk), (bo), (cf), (co), (da), (dc) and (dj);
a combination of the (v), (as), (at), (au), (bc), (bd), (bj), (bk), (bq), (cf), (da), (dc), (df) and (dj);
a combination of the (e), (v), (aa), (ar), (bc), (bd), (bk), (cf), (cj), (da), (dc) and (dj);
a combination of the (e), (v), (z), (aa), (ar), (bc), (bd), (bk), (bo), (cf), (cj), (da), (dc) and (dj);
a combination of the (e), (v), (z), (aa), (ar), (bc), (bd), (bk), (bm), (bn), (bo), (cf), (cj), (da), (dc) and (dj);
a combination of the (e), (v), (z), (aa), (ar), (bc), (bd), (bk), (bm), (bo), (cf), (cj), (cm), (da), (dc), and (dj);
a combination of the (e), (v), (z), (aa), (ar), (bc), (bd), (bk), (bm), (bn), (bo), (cf), (cj), (cm), (da), (dc) and (dj);
a combination of the (d), (e), (v), (z), (aa), (ar), (bc), (bd), (bk), (bm), (bo), (cf), (cj), (cm), (da), (dc) and (dj); and
a combination of the (d), (e), (v), (z), (aa), (ar), (bc), (bd), (bk), (bm), (bn), (bo), (cf), (cj), (cm), (da), (dc) and (dj).

In the amino acid sequence of the parent protease of the mutant according to the present invention, it is preferable that the amino acid residue at a position corresponding to position 30 of the amino acid sequence as shown in SEQ ID NO: 2 be aspartic acid, the amino acid residue at a position corresponding to position 68 thereof be histidine, and the amino acid residue at a position corresponding to position 255 thereof be serine. More preferably, the parent protease of the mutant according to the present invention has the amino acid residues shown in the following Table 1 (ii) at positions shown in the following Table 1 (i) in the amino acid sequence as shown in SEQ ID NO: 2. The amino acid residues shown in Table 1 are amino acid residues, which are highly conserved among the parent proteases as exemplified above (Saeki et al., Journal of bioscience and Bioengineering, 2007, 103: 501-508).

TABLE 1

| (i) Position | (ii) Amino acid residue |
|---|---|
| 10 | Alanine |
| 18 | Glycine |
| 21 | Glycine |
| 26 | Valine |
| 27 | Alanine |
| 28 | Valine |
| 30 | Aspartic acid |
| 32 | Glycine |
| 43 | Histidine |
| 52 | Alanine |
| 64 | Aspartic acid |
| 66 | Asparagine |
| 68 | Histidine |
| 69 | Glycine |
| 70 | Threonine |
| 71 | Histidine |
| 72 | Valine |
| 73 | Alanine |
| 74 | Glycine |
| 85 | Glycine |
| 87 | Alanine |
| 88 | Proline |
| 92 | Leucine |
| 106 | Glycine |
| 118 | Alanine |
| 129 | Serine |
| 131 | Glycine |
| 145 | Valine |
| 159 | Alanine |
| 161 | Glycine |
| 162 | Asparagine |
| 173 | Proline |
| 182 | Valine |
| 183 | Glycine |
| 184 | Alanine |
| 203 | Alanine |
| 205 | Phenylalanine |
| 206 | Serine |
| 209 | Glycine |
| 222 | Alanine |
| 223 | Proline |
| 224 | Glycine |
| 225 | Threonine |
| 229 | Serine |
| 253 | Glycine |
| 254 | Threonine |
| 255 | Serine |
| 256 | Methionine |
| 257 | Alanine |
| 259 | Proline |
| 261 | Valine |
| 262 | Alanine |
| 263 | Glycine |
| 266 | Alanine |
| 289 | Leucine |
| 297 | Glycine |

It is preferable that the amino acid residue at a position corresponding to position 303 of the SEQ ID NO:2 in the above described parent protease of the mutant according to the present invention be not aspartic acid, glutamic acid, phenylalanine, histidine, isoleucine, methionine, asparagine, proline, glutamine, threonine, valine, tryptophan or tyrosine. More preferably, the amino acid residue at a position corresponding to position 303 of SEQ ID NO:2 in the parent protease is glycine.

The above described parent protease of the mutant according to the present invention is a polypeptide having proteolytic activity on the alkaline side (preferably pH 8 or more). Preferably, the parent protease is a polypeptide having an optimum pH on the alkaline side (preferably pH 8 or more). More preferably, the parent protease has any of the following enzymatic properties possessed by the protease that consists of the amino acid sequence as shown in SEQ ID NO: 2 (Patent Literature 1): 1) The protease has resistance to oxidants, acts on the alkaline side (pH 8 or more), and is stable. Herein, the phrase "the protease has resistance to oxidants" means that, after the protease has been left in a 50 mM hydrogen peroxide (containing 5 mM calcium chloride) solution (20 mM Britton-Robinson buffer, pH 10) at 20° C. for 20 minutes, the residual activity (synthetic substrate method) is 50% or more. 2) When the protease has been treated at 50° C. at pH 10 for 10 minutes, the residual activity is 80; or more. 3) The protease is inhibited by diisopropyl fluorophosphate (DFP) and phenylmethanesulfonyl fluoride (PMSF). 4) The molecular weight is 43,000±2,000 according to SDS-PAGE. The parent protease more preferably has all of the above-described enzymatic properties 1) to 4).

Preferred examples of the parent protease of the mutant according to the present invention include a protease that consists of the amino acid sequence as shown in any of SEQ ID NOS: 2 to 4. The amino acid sequences as shown in SEQ ID NOS: 3 and 4 have an identity of 97.2% and 96.8%, respectively, with the amino acid sequence as shown in SEQ ID NO: 2

The mutant protease according to the present invention can be produced by substituting the amino acid residue at a position corresponding to position 303 of the amino acid sequence as shown in SEQ ID NO: 2 with another amino acid residue selected from the group consisting of aspartic acid, glutamic acid, phenylalanine, histidine, isoleucine, methionine, asparagine, proline, glutamine, threonine, valine tryptophan and tyrosine, in the amino acid sequence of the above described parent protease. Preferably the another amino acid residue is aspartic acid, glutamic acid, phenylalanine, isoleucine, methionine, asparagine, glutamine, valine, tryptophan or tyrosine. More preferably, the another amino acid residue is aspartic acid, glutamic acid, isoleucine, methionine, asparagine or valine.

Among the above described parent proteases, the amino acid residue at a position corresponding to position 303 of the amino acid sequence as shown in SEQ ID NO: 2 is considered to be present at a position equivalent to glycine at position 303 of the protease as shown in SEQ ID NO: 2 in the three-dimensional structure of these proteins. Accordingly, it is assumed that a mutation of the amino acid residue present at a position corresponding to position 303 in the parent protease would have effects similar to one another on their specific functions.

Besides, when one amino acid residue is inserted into the parent protease, as in the case of the above described (au), a position corresponding to the position after position 134 in SEQ ID NO: 2 in the parent protease is located downstream by one residue, in comparison to SEQ ID NO: 2. For example, in the present protease that consists of the amino acid sequence obtained by introducing the above described mutation (au) into SEQ ID NO:2, the "position corresponding to position 303" is position 304.

Accordingly, in the mutant protease according to the present invention, the amino acid residue at a position corresponding to position 303 of the amino acid sequence as shown in SEQ ID NO:2 may be an amino acid residue selected from the group consisting of aspartic acid, glutamic acid, phenylalanine, histidine, isoleucine, methionine, asparagine, proline, glutamine, threonine, valine, tryptophan and tyrosine, preferably aspartic acid, glutamic acid, phenylalanine, isoleucine, methionine, asparagine, glutamine, valine, tryptophan or tyrosine, more preferably aspartic acid, glutamic acid, isoleucine, methionine, asparagine or valine. Preferably, in the mutant protease according to the present invention, the amino acid residue at a position corresponding to position 30 of the amino acid sequence as shown in SEQ ID NO:2 is aspartic acid, the amino acid residue at a position corresponding to position 68 thereof is histidine, and the amino acid residue at a position corresponding to position 255 thereof is serine. Also, preferably, the mutant protease according to the present invention has an identity of at least 90% with the amino acid sequence as shown in SEQ ID NO:2.

The mutant protease according to the present invention has improved stability under acidic condition, preferably weakly acidic condition, in comparison to the parent protease thereof. Accordingly, the mutant protease according to the present invention is more stable in, for example, a weakly acidic undiluted liquid detergent or in a weakly acidic detergent solution in which the detergent is dissolved, and, as a result, can retain higher protease activity in such an acidic solution.

In addition to the above described mutation at a position corresponding to the position 303, the mutant protease according to the present invention may also have a mutation (e.g., a deletion, substitution, addition or insertion) at any other position in the parent protease, as long as such a mutation does not impair a stability-improving effect under acidic condition. This mutation may be either a naturally occurring mutation, or an artificially introduced mutation.

For example, the protease mutant according to the present invention may have one or more amino acid residues selected from the group consisting of the substituted or inserted amino acid residues described in the above (a) to (dv). For example, the alkaline protease mutant according to the present invention may have the following amino acid residue(s):

the substituted amino acid residue described in the (ar);
the substituted amino acid residue described in the (bk);
the substituted amino acid residue described in the (bm);
the substituted amino acid residue described in the (cj);
the substituted amino acid residue described in the (cm);
the substituted amino acid residue described in the (dc);
the substituted amino acid residue described in the (e) and (aa);
the substituted amino acid residue described in the (bc) and (bd);
the substituted amino acid residue described in the (bm) and (bn);
the substituted amino acid residue described in the (bm) and (cm);
the substituted amino acid residue described in the (bm), (bn) and (cm);
the substituted amino acid residue described in the (d), (bm) and (cm);
the substituted amino acid residue described in the (d), (bm), (bn) and (cm);
the substituted amino acid residue described in the (v), (cf), (da) and (dj);
the substituted amino acid residue described in the (j), (s), (y), (bh) and (do);
the substituted amino acid residues described in the (as), (at) and the inserted amino acid residue described in the (au);
the substituted amino acid residue described in the (e), (v), (aa), (bc), (bd), (bk), (cf), (da), (dc) and (dj);
the substituted amino acid residue described in the (e), (v), (aa), (ar), (bc), (bd), (bk), (cf), (da), (dc) and (dj);
the substituted amino acid residue described in the (j), (s), (v), (y), (as), (at), (bc), (bd), (bh), (bk), (cf), (da), (dc), (dj) and (do) and the inserted amino acid residue described in the (au);
the substituted amino acid residue described in the (v), (aa), (ar), (bc), (bd), (bk), (cf), (da), (dc) and (dj);
the substituted amino acid residue described in the (v), (as), (at), (bc), (bd), (bk), (cf), (da), (dc) and (dj) and the inserted amino acid residue described in the (au);
the substituted amino acid residue described in the (e), (v), (aa), (bc), (bd), (bk), (bo), (cf), (co), (da), (dc) and (dj);
the substituted amino acid residue described in the (v), (as), (at), (bc), (bd), (bj), (bk), (bq), (cf), (da), (dc), (df) and (dj) and the inserted amino acid residue described in the (au);
the substituted amino acid residue described in the (e), (v), (aa), (ar), (bc), (bd), (bk), (cf), (cj), (da), (dc) and (dj);
the substituted amino acid residue described in the (e), (v), (z), (aa), (ar), (bc), (bd), (bk), (bo), (cf), (cj), (da), (dc) and (dj);
the substituted amino acid residue described in the (e), (v), (z), (aa), (ar), (bc), (bd), (bk), (bm), (bn), (bo), (cf), (cj), (da), (dc) and (dj);
the substituted amino acid residue described in the (e), (v), (z), (aa), (ar), (bc), (bd), (bk), (bm), (bo), (cf), (cj), (cm), (da), (dc) and (dj);
the substituted amino acid residue described in the (e), (v), (z), (aa), (ar), (bc), (bd), (bk), (bm), (bn), (bo), (cf), (cj), (cm), (da), (dc) and (dj);
the substituted amino acid residue described in the (d), (e), (v), (z), (aa), (ar), (bc), (bd), (bk), (bm), (bo), (cf), (cj), (cm), (da), (dc) and (dj); or
the substituted amino acid residue described in the (d), (e), (v), (z), (aa), (ar), (bc), (bd), (bk), (bm), (bn), (bo), (cf), (cj), (cm), (da), (dc) and (dj).

Examples of procedures for preparing the mutant protease according to the present invention containing the substituted or inserted amino acid residue(s) described in the (a) to (dv) includes the following: in the parent protease having any one or more of the mutations described in the (a) to (dv), the amino acid residue at a position corresponding to position 303 of the amino acid sequence as shown in SEQ ID NO:2 is substituted with another amino acid residue; in the parent protease that consists of the amino acid sequence as shown in SEQ ID No:2, any one of more of the mutations described in the (a) to (dv) is introduced together with substitution at a position corresponding to position 303; or in the parent protease having any one or more of the mutations described in (a) t (dv), any one or more of the mutations described in the (a) to (dv) (however, different from the mutation possessed by the parent protease) is introduced together with substitution at position 303.

In one preferred embodiment, the mutant according to the present invention is produced by substitution of the above described amino acid residue at a position corresponding to position 303 and further substitution of at least one selected from the following $(d_1)$, $(bm_1)$, $(bn_1)$ and $(cm_1)$ in the present protease:

($d_1$) substitution of S at a position corresponding to position 15 of SEQ ID NO:2 with D or E;
($bm_1$) substitution of H at a position corresponding to position 201 of SEQ ID NO:2 with D or E, preferably with D;
($bn_1$) substitution of V at a position corresponding to position 202 of SEQ ID NO:2 with E; and (cm₁) substitution of N at a position corresponding to position 304 of SEQ ID NO:2 with A.

More preferably, the further substitution is the (cm₁); (bm₁) and (cm₁); (bm₁), (bn₁) and (cm₁); (d₁), (bm₁) and (cm₁); or (d₁), (bm₁), (bn₁) and (cm₁). Preferably, the substitution at a position corresponding to position 303 is substitution with E or N. Preferably, the parent protease is a protease that consists of the amino acid sequence as shown in any of SEQ ID Nos 2 to 4.

In more preferred embodiment, the mutant according to the present invention is produced by any of the following substitution 1) to 10) in a parent protease:

1) substitution of G at a position corresponding to position 303 of SEQ ID NO:2 with E, and
substitution of N at a position corresponding to position 304 of SEQ ID NO:2 with A;

2) substitution of G at a position corresponding to position 303 of SEQ ID NO:2 with E,
substitution of H at a position corresponding to position 201 of SEQ ID NO:2 with D, and
substitution of N at a position corresponding to position 304 with A;

3) substitution of G at a position corresponding to position 303 of SEQ ID NO:2 with E,
substitution of S at a position corresponding to position 15 of SEQ ID NO:2 with D or E,
substitution of H at a position corresponding to position 201 of SEQ ID NO:2 with D, and
substitution of N at a position corresponding to position 304 of SEQ ID NO:2 with A;

4) substitution of G at a position corresponding to position 303 of SEQ ID NO:2 with E,
substitution of H at a position corresponding to position 201 of SEQ ID NO:2 with D,
substitution of V at a position corresponding to position 202 of SEQ ID NO:2 with E, and
substitution of N at a position corresponding to position 304 of SEQ ID NO:2 with A, 5) substitution of G at a position corresponding to position 303 of SEQ ID NO:2 with E,
substitution of S at a position corresponding to position 15 of SEQ ID NO:2 with D or E,
substitution of H at a position corresponding to position 201 of SEQ ID NO:2 with D,
substitution of V at a position corresponding to position 202 of SEQ ID NO:2 with E, and
substitution of N at a position corresponding to position 304 of SEQ ID NO:2 with A;

6) substitution of G at a position corresponding to position 303 of SEQ ID NO:2 with N, and
substitution of N at a position corresponding to position 304 of SEQ ID NO:2 with A;

7) substitution of G at a position corresponding to position 303 of SEQ ID NO:2 with N,
substitution of H at a position corresponding to position 201 of SEQ ID NO:2 with D, and
substitution of N at a position corresponding to position 304 of SEQ ID NO:2 with A;

8) substitution of G at a position corresponding to position 303 of SEQ ID NO:2 with N,
substitution of S at a position corresponding to position 15 of SEQ ID NO:2 with D or E,
substitution of H at a position corresponding to position 201 of SEQ ID NO:2 with D, and
substitution of N at a position corresponding to position 304 of SEQ ID NO:2 with A;

9) substitution of G at a position corresponding to position 303 of SEQ ID NO:2 with N,
substitution of H at a position corresponding to position 201 of SEQ ID NO:2 with D,
substitution of V at a position corresponding to position 202 of SEQ ID NO:2 with E, and
substitution of N at a position corresponding to position 304 of SEQ ID NO:2 with A; and 10) substitution of G at a position corresponding to position 303 of SEQ ID NO:2 with N,
substitution of S at a position corresponding to position 15 of SEQ ID NO:2 with D or E,
substitution of H at a position corresponding to position 201 of SEQ ID NO:2 with D,
substitution of V at a position corresponding to position 202 of SEQ ID NO:2 with E, and
substitution of N at a position corresponding to position 304 of SEQ ID NO:2 with A.

Preferably, the parent protease is a protease that consists of the amino acid sequence as shown in any of SEQ ID Nos: 2 to 4. Examples of such mutant according to the present invention include a protease that consists of the amino acid sequence as shown in any of SEQ ID Nos: 5 to 7.

In the present invention, as a means for mutating the amino acid residue(s) in the parent protease, various types of mutation introduction techniques, which have been known in the present technical field, can be used. For instance, in a polynucleotide encoding the amino acid sequence of the alkaline protease (hereinafter also referred to as a "parent polynucleotide"), a nucleotide sequence encoding an amino acid residue to be mutated is mutated to a nucleotide sequence encoding the mutated amino acid residue, and a protein is then allowed to express from the mutant gene, so that an alkaline protease mutant of interest can be obtained.

Basically, introduction of a mutation of interest into a parent polynucleotide can be carried out, for example, by performing various site-directed mutagenesis methods, which are well known to a person skilled in the art, based on PCR amplification using the parent polynucleotide as template DNA or a replication reaction using various types of DNA polymerases. Such a site-directed mutagenesis method can be carried out, for example, by applying any method such as an inverse PCR method or an annealing method (edited by Muramatsu et al., "Revised 4th edition, "New Gene Engineering Handbook", Yodosha, pp. 82-88). It is also possible to use various types of commercially available kits for site-directed mutagenesis, such as Quick Change II Site-Directed Mutagenesis Kit or Quick Change Multi Site-Directed Mutagenesis Kit from Stratagene.

The site-directed mutagenesis into the parent polynucleotide can be carried out, most commonly, using mutation primers containing a nucleotide mutation to be introduced. The mutation primers may be designed, such that they anneal to a region containing a nucleotide sequence encoding an amino acid residue to be mutated in a parent polynucleotide, and contain a nucleotide sequence having a nucleotide sequence (codon) encoding the mutated amino acid residue, instead of a nucleotide sequence (codon) encoding the amino acid residue to be mutated. A person skilled in the art could appropriately recognize and select nucleotide sequences (codons) encoding the unmutated and mutated amino acid residues, based on a common textbook and the like. Alternatively, the site-directed mutagenesis can be carried out by a method of using separately two primers complementary to each other containing a nucleotide mutation to be introduced to amplify DNA fragments of an upstream side and a downstream side of a mutation site and ligating the DNA fragments into one fragment, according to SOE (splicing by overlap extension)—PCR (Horton et al, Gene, 1989, 77(1): pp. 61-68).

A template DNA containing a parent polynucleotide can be prepared from bacteria such as the aforementioned *Bacillus* sp. KSM-KP43 (FERM BP-6532), *Bacillus* sp. KSM-KP9860 (FERM BP-6534) or *Bacillus* sp. KSM-9865 (FERM P-18566), or mutant strains thereof by extracting genomic DNA therefrom according to a common method, or by extracting RNA therefrom and then synthesizing cDNA by reverse transcription. Alternatively, based on the amino acid sequence of the parent protease, the corresponding nucleotide sequence may be chemically synthesized, and may be then used as the template DNA.

Preparation of genomic DNA from such a strain of *Bacillus* sp. can be carried out, for example, by applying the method described in Pitcher et al, Lett Appl Microbiol, 1989, 8: 151-156 and the like. Template DNA containing a parent polynucleotide may be prepared in a form in which the prepared cDNA, or a DNA fragment containing a parent polynucleotide cleaved from genomic DNA is inserted into any vector.

Mutation primers can be produced according to a publicly known oligonucleotide synthetic method, such as a phosphoramidite method (Nucleic Acids Research, 1989, 17: 7059-7071). Such primer synthesis can also be carried out, for example, using a commercially available oligonucleotide synthesizing apparatus (manufactured by ABI, etc.). The site-directed mutagenesis as described above is carried out using a parent polynucleotide as a template DNA and using a primer set including the mutation primers, so that a mutant protease gene, into which a mutation of interest has been introduced, can be obtained.

Accordingly, the present invention also provides a mutant protease gene. The mutant protease gene according to the present invention is a polynucleotide encoding the mutant protease according to the present invention. The polynucleotide according to the present invention may include single-stranded or double-stranded DNA, cDNA, RNA, and other artificial nucleic acids. The DNA, cDNA and RNA may also be chemically synthesized. Further, the polynucleotide according to the present invention may contain a nucleotide sequence of an untranslated region (UTR), in addition to an open reading frame (ORF).

The present invention also provides a vector containing the polynucleotide encoding the mutant protease according to the present invention. The vector can be produced by inserting the polynucleotide according to the present invention into any vector, and thus ligating them according to a common method. The type of the vector is not particularly limited, and it may be any vector such as a plasmid, a phage, a phagemid, a cosmid, a virus, a YAC vector or a shuttle vector. Moreover, the vector is preferably a vector capable of amplifying in bacteria, particularly in bacteria of *Bacillus* sp., more preferably an expression vector capable of inducing expression of an introduced gene in bacteria of *Bacillus* sp., although the vector is not limited thereto. Among them, a shuttle vector, which is replicable in any of bacteria of *Bacillus* sp. and another organism, can be preferably used in recombination production of the mutant protease according to the present invention. Examples of a preferred vector include, but are not limited to: shuttle vectors such as pHA3040SP64, pHSP64R or pASP64 (JP-B-3492935), pHY300PLK (an expression vector capable of transforming both *Escherichia coli* and *Bacillus subtilis*; Ishikawa and Shibahara, Jpn J Genet, 1985, 60: 235-243), and pAC3 (Moriyama et al, Nucleic Acids Pes, 1988, 16: 8732); plasmids available for transformation of bacteria of *Bacillus* sp. such as pUB110 (Gryczan et al, J Bacteriol, 1978, 134: 318-329) or pTA10607 (Bron et al, Plasmid, 1987, 18: 8-15); and secretion vectors capable of giving secretion signals to recombinant proteins (Yamane et al., "Fusion Proteins Using *Bacillus subtilis* Secretion Vectors," Starch Science, 34. (1987), 163-170). Furthermore, *Escherichia coli*-derived plasmids (e.g., pET22b(+), pBR322, pBR325, pUC118, pUC119, pUC18, pUC19, pBluescript, etc.) can also be used.

When the mutant protease according to the present invention is produced by recombination, the vector is preferably an expression vector. The expression vector may contain, as necessary, useful sequences including various types of elements essential for expression in host organisms, such as a transcription promoter, a terminator, or a ribosome-binding site; cis-elements such as a polylinker or an enhancer; poly A addition signal; a ribosome binding sequence (SD sequence); and selective marker genes such as a drug (e.g., ampicillin, neomycin, kanamycin, tetracycline, chloramphenicol, etc.) resistant gene.

The present invention further provides a transformant containing a polynucleotide encoding the mutant protease according to the present invention or a vector containing such a polynucleotide. The transformant can be produced by introducing a polynucleotide encoding the mutant protease according to the present invention or a vector containing such a polynucleotide (preferably, a recombinant expression vector) into a host. Accordingly, the transformant contains a foreign polynucleotide encoding the mutant protease according to the present invention.

Examples of a host for the transformant include: bacteria such as *Escherichia coli* or *Bacillus subtilis*; microorganisms including yeast cells as typical examples; and any cells such as insect cells, animal cells (e.g., mammalian cells), or plant cells. The host is preferably a bacterium of *Bacillus* sp., more preferably *Bacillus subtilis* or a mutant strain thereof. Therefore, the transformant according to the present invention is preferably a recombinant bacterium of *Bacillus* sp., and more preferably a recombinant *Bacillus subtilis* or a mutant strain thereof.

For transformation of a host, publicly known transformation techniques, such as a calcium phosphate method, an electroporation method, a lipofection method, a particle gun method, or a PEG method, can be applied. Examples of a transformation method applicable to bacteria of *Bacillus* sp., include a competent cell transformation method (J Bacteriol, 1967, 93: 1925-1937), an electroporation method (FEMS Microbiol Lett, 1990, 55: 135-138), a protoplast transformation method (Mol Gen Genet, 1979, 168: 111-115), and a Tris-PEG method (J Bacteriol, 1983, 156: 1130-1134).

The mutant protease according to the present invention can be produced by culturing the transformant according to the present invention. Accordingly, the present invention also provides a method for producing a mutant protease including, using the transformant according to the present invention. The transformant for production of a mutant protease can be cultured according to a common method well known to a person skilled in the art. For instance, a medium used to culture a transformant based on a microorganism host such as *Escherichia coli* or yeast cells may be a medium which contains therein a carbon source, a nitrogen source, inorganic salts, etc. capable of being assimilated by the microorganism host, and in which the transformant can be efficiently cultured therein. The medium used herein may be either a natural medium or a synthetic medium. For instance, for the culture of a *Bacillus subtilis* transformant to produce a recombinant protein, an LB medium, a 2×YT medium, a 2×L-maltose medium, a CSL fermentation medium or the like can be used. To such a medium, a drug which corresponds to the type of a drug resistant gene (selective marker gene) introduced into the transformant, may be added. In addition, in the case of culturing microorganisms transformed with an expression vector using an inducible promoter, an inducer may be added to the medium, as necessary. For example, in the case of culturing microorganisms transformed with an expression vector using a Lac promoter, isopropyl-1-thio-β-D-galactoside (IPTG), etc. can be added to the medium. In the case of culturing microorganisms transformed with an expression vector using a trp promoter, indoleacetic acid (IAA), etc. can be added to the medium.

Alternatively, the mutant protease according to the present invention may be expressed from a polynucleotide encoding the mutant protease according to the present invention or a transcriptional product thereof, using a cell-free translation system. The "cell-free translation system" refers to an in vitro transcription translation system or an in vitro translation system, which is obtained by adding reagents necessary for translation of proteins, such as amino acids, to a suspension obtained by mechanically homogenizing cells serving as a host.

The mutant protease according to the present invention produced in the aforementioned transformant or cell-free translation system can be obtained from a culture solution, a cell-homogenized solution, a reaction solution of the cell-free translation system, etc., by applying common methods used in protein purification, such as centrifugation, ammonium sulfate precipitation, gel chromatography, ion exchange chromatography, and affinity chromatography alone or in appropriate combination. Alternatively, a solution separated or concentrated using centrifugation, an ultrafiltration filter and the like, such as a culture supernatant or a lysate supernatant, can be directly used as a crude enzyme solution. When the expressed mutant protease is not secreted from cells, the cells may be homogenized, and then, separation and purification of proteins may be carried out.

Experiments used in the present invention, such as preparation of mRNA, production of cDNA, PCR, RT-PCR, production of a library, ligation into a vector, transformation of cells, determination of DNA base sequence, chemical synthesis of nucleic acids, determination of amino acid sequence on the N-terminal side of a protein, mutagenesis, and extraction of a protein, can be carried out according to methods described in ordinary experimental manuals. Examples of such an experimental manual include Sambrook et al., Molecular Cloning, A laboratory manual, 2001, 3rd Ed., Sambrook, J. & Russell, D W., Cold Spring Harbor Laboratory Press. Moreover, in the case of an experiment regarding genetic recombination of *Bacillus subtilis*, common experimental manuals for genetic engineering of *Bacillus subtilis* such as Hirofumi Yoshikawa, "7.2 *Bacillus subtilis* system," "Continued Biochemical Experiment Seminar 1. Genetic Research Method II," 1986, Tokyo Kagaku Dojin Co., Ltd. (Tokyo), pp. 150-169, etc., can be referred to, for example.

The mutant protease obtained by the production method according to the present invention has improved stability under acidic condition, preferably weakly acidic condition, in comparison to the parent protease thereof, and thus, the present mutant protease can be more stably present in an acidic solution, for examples, in a weakly acidic undiluted liquid detergent or in a weakly acidic detergent solution in which the detergent is dissolved. Accordingly, another aspect of the present invention may be a method for improving the stability of protease under acidic condition, including substituting the amino acid residue at a position corresponding to position 303 of the amino acid sequence as shown in SEQ ID NO: 2 in the amino acid sequence of the above described parent protease with an amino acid residue selected from the group consisting of aspartic acid, glutamic acid, phenylalanine, histidine, isoleucine, methionine, asparagine, glutamine, threonine, valine, tryptophan and tyrosine.

Since the mutant protease according to the present invention has high stability under acidic condition, it not only has high protease activity at pH on the alkaline side but also can stably retain enzymatic activity even under acidic condition. Therefore, the mutant protease according to the present invention is useful as a detergent enzyme and more suitable to an enzyme for weakly acidic detergent. Accordingly, the present invention also provides a detergent composition containing the mutant protease according to the present invention. The detergent composition may be a solid detergent composition, but it is preferably a liquid detergent composition. Further, the detergent composition is preferably a weakly acidic detergent composition. The weakly acidic composition in the present description includes an undiluted liquid detergent having weakly acidic pH and a liquid or solid (for example, powdery) detergent exhibiting weak acidity when dissolved in water. Further, the weak acidity in the present description refers to preferably acidic condition of pH 5 or more, more preferably pH 5 or more and less than pH 7, still more preferably from pH 6 to pH 6.8.

The content of the mutant protease according to the present invention in the detergent composition according to the present invention is not particularly limited, as long as the protease exhibits its activity. The content of the mutant protease according to the present invention is preferably from 0.1 to 25000 U, more preferably from 0.1 to 5000 U, further preferably from 0.1 to 2500 U, based on 1 kg of the detergent composition. Besides, the activity (U) of the protease in the present description is measured by the following method. That is, 0.9 mL of $1/15$ M phosphate buffer (for example, pH 7.4, a solution prepared by dissolving one package of Wako Pure Chemical phosphate buffer powder (167-14491) (containing 7.6 g of $Na_2HPO_4$ (anhydrous) and 1.8 g of $KH_2PO_4$ (anhydrous) per 1 package) in IL of ion exchanged water) and 0.05 mL of 40 mM Glt-Ala-Ala-Pro-Leu-p-nitroanilide/dimethyl sulfoxide solution are added into a test tube, and are then kept warm at 30° C. for 5 minutes. To the obtained mixture, 0.05 mL of enzyme solution is added, followed by performing a reaction at 30° C. for 10 minutes. Thereafter, 2.0 mL of 5% (w/v) citric acid aqueous solution is added to the reaction solution to terminate the reaction, and the absorbance at 420 nm is then measured using a spectrophotometer. Herein, 1 unit (U) of enzyme is defined to be an amount of enzyme necessary for producing 1 μmol p-nitroaniline for 1 minute in the above described reaction.

The detergent composition according to the present invention contains a surfactant and water, in addition to the mutant protease according to the present invention. As such surfactants, any surfactants such as an anionic surfactant, a nonionic surfactant, an amphoteric surfactant, and a cationic surfactant can be used alone or in combination of two or more types. The content of the surfactant in the detergent composition according to the present invention is preferably from 10% to 80% by mass, more preferably from 30% to 70% by mass.

The nonionic surfactant may be a nonionic surfactant having a C8 to C22 hydrocarbon group and with several moles or more of C2 oxyalkylene groups added, which is generally mixed into a liquid detergent. Examples of such a nonionic surfactant include:

- $R_1O$-(AO)m-H (wherein $R_1$=C8 to C22 hydrocarbon, AO=C2 to C5 oxyalkylene group, and m=16 to 35) [JP-A-2010-275468];
- $R_1O$-(EO)l-(AO)m-(EO)n-H (wherein $R_1$=C8 to C18 hydrocarbon, EO=C2 oxyalkylene group, AO=C3 to C5 oxyalkylene group, l=3 to 30, m=1 to 5, and l+n=14 to 50) [JP-A-2010-265445, JP-A-2011-63784];
- $R_1O$-(EO)m/(AO)n-H (wherein $R_1$=C8 to C22 hydrocarbon, EO=C2 oxyalkylene group, AO=C3 to C5 oxyalkylene group, m=10 to 30, n=0 to 5, and EO and AO are random or block bonds) [JP-A-2010-189551];
- $R_1$(CO)lO-(EO)m/(AO)n-$R_2$ (wherein $R_1$=C8 to C22 hydrocarbon, EO=C2 oxyalkylene group, AO=C3 to C5 oxyalkylene group, l=0 to 1, m=14 to 50, n=1 to 5, $R_2$=hydrogen (l=0) or C1 to C3 alkyl group, and EO and AO are random or block bonds) [JP-A-2010-229385];
- $R_1O$-(EO)m-(AO)r-H (wherein $R_1$=C8 to C22 hydrocarbon, EO=C2 oxyalkylene group, AO=C3 to C5 oxyalkylene group, m=15 to 30, and n=1 to 5) [JP-A-2010-229387];
- $R_1O$-(AO) m/(Gly) n-H and/or $R_2$—COO-(AO) p/(Gly) q-H (wherein $R_1$=C8 to C22 hydrocarbon group, $R_2$=C7 to C21 hydrocarbon group, AO=C2 to C3 oxyalkylene group, Gly=glycerol group, m=0 to 5, n=2 to 10, p=0 to 5, q=2 to 10, and AO and Gly are random or block bonds) [JP-A-2010-254881];
- $R_1$—COO—(PO)m/(EO)n-$R_2$ (wherein $R_1$=C7 to C21 hydrocarbon group, COO=carbonyloxy group, $R_2$=C1 to C3 alkyl group, PO=oxypropylene group, EO=oxyethylene group, m=0.3 to 5, n=8 to 25, and PO and EO are random or block bonds) [JP-A-2010-265333];
- $R_1O$-(EO)l-(PO)m-(EO)n-H (wherein $R_1$=C8 to C20 hydrocarbon, EO=C2 oxyalkylene group, PO=oxypropylene group, l>=1, n>=1, 0<m<l+n, and EO and PO are random or block bonds) (WO98/248651);
- $R_1O$-(EO)m-(PO)n-H (wherein $R_1$=C10 to C16 alkyl group or alkenyl group, EO=ethyleneoxide group, PO=propyleneoxide group, m=5 to 15, and n=1 to 3) [JP-A-8-157867];
- $R_1$(CO)-(EO)m-$OR_2$ (wherein $R_1$=C11 to C13 linear or branched alkyl group or alkenyl group, $R_2$=C1 to C3 alkyl group, EO=ethyleneoxide group, and m=10 to 20) [JP-A-2008-7706, JP-A-2009-7451, JP-A-2009-155594, and JP-A-2009-155606];
- $R_1$(CO)-(AO)m-$OR_2$ (wherein $R_1$=C9 to C13 linear or branched alkyl group or alkenyl group, AO=C2 to C4 oxyalkylene group, $R_2$=C1 to C3 alkyl group, m=5 to 30)[JP-A-2009-144002, JP-A-2009-173858, and JP-A-2010-189612]; and
- fatty acid alkanolamide, fatty acid alkanol glucamide, and alkyl polyglucoside.

Examples of the anionic surfactant include a carboxylate-type anionic surfactant, a sulfonate-type or sulfate-type anionic surfactant, a nonsoap anionic surfactant, linear alkylbenzenesulfonic acid, benzenesulfonic acid or a salt thereof, polyoxybenzenesulfonic acid or a salt thereof, a polyoxyethylene alkyl sulfate salt, a polyoxyalkylene alkyl ether sulfate salt, α-olefin sulfonate, alkyl benzenesulfonate, α-sulfo fatty acid salt, fatty acid soap, a phosphate-based surfactant, acyl alaninate, acyl taurate, alkyl ether carboxylic acid, and alcohol sulfate.

Examples of the cationic surfactant include a quaternary ammonium salt having a long-chain alkyl group, a tertiary amine having one long-chain alkyl group, an alkyltrimethylammonium salt, a dialkyldimethylammonium salt, and an alkyl pyridinium salt. Preferred examples of the cationic surfactant include a quaternary ammonium-type surfactant having one long-chain alkyl group having 8 to 22 carbon atoms, and a tertiary amine having one long-chain alkyl group having 8 to 22 carbon atoms.

Examples of the amphoteric surfactant include alkylbetaine-type, alkylamidobetaine-type, imidazoline-type, alkylaminosulfone-type, alkylaminocarboxylic acid-type, alkylamidocarboxylic acid-type, and amidoamino acid-type or phosphoric acid-type amphoteric surfactants, such as alkylacetic acid betaine, alkanolamido propyl acetic acid betaine, alkyl imidazoline, and alkyl alanine. A preferred example of the amphoteric surfactant is sulfobetaine or carbobetaine having an alkyl group having 10 to 18 carbon atoms.

The detergent composition according to the present invention may further contain components commonly used in a detergent composition, such as, for example, a water-soluble polymer, a water-miscible organic solvent, an alkaline agent, organic acid or a salt thereof, a chelating agent, an enzyme other than the mutant protease according to the present invention, an enzyme stabilizer, a fluorescent agent, an anti-refouling agent, a dispersant, a color migration inhibitor, a finishing agent, a bleaching agent, an antioxidant, a solubilizer, a pH adjuster, a buffer, an antiseptic, a perfume, a salt, alcohol, and sugars.

Examples of the water-soluble polymer include: a polymer compound, having (i) a polyether chain moisty containing a polymerized unit derived from an epoxide having 2 to 5 carbon atoms, and (ii) a polymer chain moiety containing a polymerized unit derived from one or more unsaturated carboxylic acid monomers selected from the group consisting of acrylic acid, methacrylic acid and maleic acid, and having a graft structure in which either (i) or (ii) is a main chain, and the other is a branched chain (JP-A-2010-275468 and JP-A-10-060496); and a water-soluble polymer having an alkylene terephthalate unit and/or an alkylene isophthalate unit, and an oxyalkylene unit and/or a polyoxyalkylene unit (JP-A-2009-155606). The content of the water-soluble polymer in the detergent composition according to the present invention is preferably from 0.2% to 10% by mass, more preferably from 0.4% to 5% by mass.

Examples of the water-miscible organic solvent include alkanols such as alkylene glycols or glycerin, polyalkylene glycols, (poly)alkylene glycol (mono or di)alkyl ethers, alkyl glyceryl ethers, and aromatic ethers of (poly)alkylene glycol. Preferred examples of the water-miscible organic solvent include alkylene glycols having from 2 to 6 carbon atoms, such as ethylene glycol, propylene glycol, butylene glycol or hexylene glycol, glycerin, polyethylene glycol monophenyl ether, ethylene glycol monobenzyl ether, and diethylene glycol monobenzyl ether. The content of the water-miscible organic solvent in the detergent composition according to the present invention is preferably from 1% to 40% by mass, more preferably from 1% to 35% by mass.

Examples of the alkaline agent include alkanolamines having one to three C2 to C4 alkanols, such as monoethanolamine, diethanolamine, triethanolamine, polyoxyalkyleneamine, or dimethylaminopropylamine. Among these, monoethanolamine and triethanolamine are preferable. The content of the alkaline agent in the detergent composition according to the present invention is preferably from 0% to 20% by mass, more preferably from 0% to 10% by mass.

Examples of the organic acid or a salt thereof include: polyvalent carboxylic acids such as saturated fatty acid, succinic acid, maleic acid, and fumaric acid, or their salts; and hydroxycarboxylic acids such as citric acid, malic acid, glycolic acid, and p-hydroxybenzoic acid, or their salts. Among these, citric acid or salt thereof is preferable. The content of the organic acid or a salt thereof in the detergent composition according to the present invention is preferably from 0% to 5% by mass, more preferably from 01 to 3% by mass.

In the preset description, the "chelating agent" means a compound capable of coordinate-bonding with metal ions. A chelating agent added to a detergent composition has an action to block metal ions which negatively affect washing of, for example, calcium ions or magnesium ions existing in washing water or stain. Examples of such a chelating agent which can be contained in the detergent composition according to the present invention include: aminopolyacetic acids such as nitrilotriacetic acid, iminodiacetic acid, ethylenediamineacetic acid, diethylenetriaminepentaacetic acid, glycol ether diaminetetraacetic acid, hydroxyethyliminodiacetic acid, triethylenetetramine hexaacetic acid, and djenkolic acid, or the salts thereof; organic acids such as diglycolic acid, oxydisuccinic acid, carboxymethyloxysuccinic acid, citric acid, lactic acid, tartaric acid, oxalic acid, malic acid, oxydisuccinic acid, gluconic acid, carboxymethylsuccinic acid, and carboxymethyltartaric acid, or the salts thereof; aminotri(methylenephosphonic acid), 1-hydroxyethylidene-1,1-diphosphonic acid, ethylenediaminetetra(methylenephosphonic acid), diethylenetriaminepenta(methylenephosphonic acid); and their salts of alkali metals or lower amines. The content of the chelating agent in the detergent composition according to the present invention is preferably from 0.1% to 5% by mass, more preferably from 0.1% to 4% by mass.

Examples of the anti-refouling agent and the dispersant include anti-refouling agents and dispersers such as polyacrylic acid, polymaleic acid, carboxymethyl cellulose, polyethylene glycol having a weight average molecular weight of 5000 or more, a maleic anhydride-diisobutylene copolymer, a maleic anhydride-methyl vinyl ether copolymer, a maleic anhydride-vinyl acetate copolymer, a naphthalene sulfonate formalin condensate, and polymers recited in claims 1 to 21 of JP-A-59-62614 (page 1, column 3, line 5 to page 3, column 4, line 14).

The color migration inhibitor is, for example, polyvinyl pyrrolidone. The content of the color migration inhibitor in the detergent composition according to the present invention is preferably from 0.01% to 10% by mass.

A bleaching agent such as hydrogen peroxide, percarbonate or perborate is added in an amount of 1% to 10% by mass into the present detergent composition. In the case of using such a bleaching agent, tetraacetylethylenediamine (TAED) or a bleaching activator (activator) described in JP-A-6-316700, etc., can be added in an amount of from 0.01% to 10% by mass into the detergent composition.

Examples of the fluorescent agent include a biphenyl-type fluorescent agent (Tinopal CBS-X, etc.) and a stilbene-type fluorescent agent (DM-type fluorescent dye, etc.). The content of the fluorescent agent in the detergent composition according to the present invention is preferably from 0.001 to 2 by mass.

Examples of the enzyme other than the mutant protease according to the present invention include hydrolytic enzymes such as other proteases, cellulase, β-glucanase, hemicellulase, lipase, peroxidase, laccase, α-amylase, glucoamylase, cutinase, pectinase, reductase, oxidase, phenol oxidase, ligninase, pullulanase, pectate lyase, xyloglucanase, xylanase, pectin acetyl esterase, polygalacturonase, rhamnogalacturonase, pectin lyase, mannanase, pectin methyl esterase, cellobiohydrolase and transglutaminase, and a mixture of two or more of these enzymes.

Examples of the enzyme stabilizer include a boron compound, a calcium ion source (a calcium ion-supplying compound), a hydroxy compound, and formic acid. Examples of the antioxidant include butylhydroxytoluene, distyrenated cresol, sodium sulfite, and sodium hydrogen sulfite. Examples of the solubilizer include p-toluenesulfonic acid, cumenesulfonic acid, m-xylenesulfonic acid, and benzoate (which also has an effect as an antiseptic). Furthermore, the detergent composition according to the present invention may also contain: water-immiscible organic solvents including paraffins such as octane, decane, dodecane or tridecane, olefins such as decene or dodecene, halogenated alkyls such as methylene chloride or 1,1,1-trichloroethane, and terpenes such as D-limonene; pigments; perfumes; antibacterial-antiseptic agents; and antifoaming agents such as silicone.

Preferred examples of a detergent composition which can contain the mutant protease according to the present invention include the liquid detergent compositions described in JP-A-2017-008303 (Patent Literature 8) and the liquid detergent having pH 6.5 described in Example 2 of JP-A-2013-129729. The detergent composition according to the present invention can be prepared by mixing the mutant protease according to the present invention in these detergent compositions.

The detergent composition according to the present invention is not limited to, but preferred examples thereof include a detergent composition used for washing clothes or fabrics (sheets, curtains, carpets, wall clothes, etc.) and a detergent composition for face or body. Since the detergent composition according to the present invention can stably maintain the protease activity by containing the mutant protease according to the present invention, it can exhibit high detergency.

The present invention also includes, as illustrative embodiments, the following substances, production methods, intended uses, methods, etc. However, the present invention is not limited to these embodiments.

[1] A mutant protease that consists of an amino acid sequence having an identity of at least 90% with the amino acid sequence as shown in SEQ ID NO:2 and that has the following amino acid residue at a position corresponding to position 303 of the amino acid sequence as shown in SEQ ID NO:2, an amino acid residue selected from the group of consisting of aspartic acid, glutamic acid, phenylalanine, histidine, isoleucine, methionine, asparagine, proline, glutamine, threonine, valine, tryptophan, and tyrosine, preferably an amino acid residue selected from the group of consisting of aspartic acid, glutamic acid, phenylalanine, isoleucine, methionine, asparagine, glutamine, valine, tryptophan, and tyrosine, more preferably an amino acid residue selected from the group of consisting of aspartic acid, glutamic acid, isoleucine, methionine, asparagine, and valine.

[2] The mutant protease according to [1], which (i) preferably has one or more amino acid residues selected from the group consisting of the following (a') to (dv'):

(a') S, T, C, Q, Y, R, K, H, A, V, L, I, M, W or F at position 6 of the amino acid sequence as shown in SEQ ID NO: 2 or at a position corresponding thereto;
(b') Q at position 9 of the amino acid sequence as shown in SEQ ID NO: 2 or at a position corresponding thereto;
(c') G, S or N at position 11 of the amino acid sequence as shown in SEQ ID NO: 2 or at a position corresponding thereto;
(d') H, C, Q, D, E, R, A, V, M, W or F at position 15 of the amino acid sequence as shown in SEQ ID NO: 2 or at a position corresponding thereto;
(e') T, Q, V, C, Y, D, E, R, K, H, L, I, M, W or F at position 16 of the amino acid sequence as shown in SEQ ID NO: 2 or at a position corresponding thereto;
(f) F or A at position 20 of the amino acid sequence as shown in SEQ ID NO: 2 or at a position corresponding thereto;
(g') W at position 22 of the amino acid sequence as shown in SEQ ID NO: 2 or at a position corresponding thereto;
(h') N at position 23 of the amino acid sequence as shown in SEQ ID NO: 2 or at a position corresponding thereto;
(i') T at position 37 of the amino acid sequence as shown in SEQ ID NO: 2 or at a position corresponding thereto;
(j') V, L, I, W or F at position 40 of the amino acid sequence as shown in SEQ ID NO: 2 or at a position corresponding thereto;
(k') I at position 41 of the amino acid sequence as shown in SEQ ID NO: 2 or at a position corresponding thereto;
(l') S, T, C, N, Q, Y, E, K, H, A, V, L, I, M or W at position 46 of the amino acid sequence as shown in SEQ ID NO: 2 or at a position corresponding thereto;
(m') Q at position 49 of the amino acid sequence as shown in SEQ ID NO: 2 or at a position corresponding thereto;
(n') G or S at position 52 of the amino acid sequence as shown in SEQ ID NO: 2 or at a position corresponding thereto;
(o') A, V or I at position 53 of the amino acid sequence as shown in SEQ ID NO: 2 or at a position corresponding thereto;
(p') G, S, T, C, N, Q, D, E, R, H, A, V, M, W, F or P at position 54 of the amino acid sequence as shown in SEQ ID NO: 2 or at a position corresponding thereto;
(q') V at position 56 of the amino acid sequence as shown in SEQ ID NO: 2 or at a position corresponding thereto;
(r') S, T, C, Q, D, E, R, K, H, A, V, L, I, M, W, F or P at position 57 of the amino acid sequence as shown in SEQ ID NO: 2 or at a position corresponding thereto;
(s') V, L, I, M, W or F at position 59 of the amino acid sequence as shown in SEQ ID NO: 2 or at a position corresponding thereto;
(t') V, L, I, W or F at position 60 of the amino acid sequence as shown in SEQ ID NO: 2 or at a position corresponding thereto;
(u') S, D or L at position 63 of the amino acid sequence as shown in SEQ ID NO: 2 or at a position corresponding thereto;
(v') W or P at position 65 of the amino acid sequence as shown in SEQ ID NO: 2 or at a position corresponding thereto;
(w') G, S, T, C, Q, D, E, H, A, V, L, I, M or W at position 66 of the amino acid sequence as shown in SEQ ID NO: 2 or at a position corresponding thereto;
(x') H or A at position 80 of the amino acid sequence as shown in SEQ ID NO: 2 or at a position corresponding thereto;
(y') Q, Y, L, I, W or F at position 81 of the amino acid sequence as shown in SEQ ID NO: 2 or at a position corresponding thereto;
(z') G, S, C, Q, D, E, R, K, H, A or M at position 82 of the amino acid sequence as shown in SEQ ID NO: 2 or at a position corresponding thereto;
(aa') S, C or A at position 83 of the amino acid sequence as shown in SEQ ID NO: 2 or at a position corresponding thereto;
(ab') R at position 84 of the amino acid sequence as shown in SEQ ID NO: 2 or at a position corresponding thereto;
(ac') H at position 89 of the amino acid sequence as shown in SEQ ID NO: 2 or at a position corresponding thereto;
(ad') C at position 91 of the amino acid sequence as shown in SEQ ID NO: 2 or at a position corresponding thereto;
(ae') L, I, W or F at position 100 of the amino acid sequence as shown in SEQ ID NO: 2 or at a position corresponding thereto;
(af') S, T, C, N, Q, Y, D, E, R, K, H, A, V, L, I, M, W, F or P at position 101 of the amino acid sequence as shown in SEQ ID NO: 2 or at a position corresponding thereto;
(ag') S, T, C, Q, Y, D, E, R, K, H, A, V, L, I, M, W, F or P at position 102 of the amino acid sequence as shown in SEQ ID NO: 2 or at a position corresponding thereto;
(ah') S, T, C, Q, Y, D, E, R, K, H, A, V, L, I, M, W, F or P at position 103 of the amino acid sequence as shown in SEQ ID NO: 2 or at a position corresponding thereto;
(ai') S, T, C, Q, Y, D, E, R, K, H, A, V, L, I, M, W, F or P at position 104 of the amino acid sequence as shown in SEQ ID NO: 2 or at a position corresponding thereto;
(aj') S, T, C, Q, Y, D, E, R, K, H, A, V, L, I, M, W, F or P at position 105 of the amino acid sequence as shown in SEQ ID NO: 2 or at a position corresponding thereto;
(ak') S, T, C, Q, Y, D, E, R, K, H, A, V, L, I, M, W, F or P at position 106 of the amino acid sequence as shown in SEQ ID NO: 2 or at a position corresponding thereto;
(al') S, R, K or A at position 107 of the amino acid sequence as shown in SEQ ID NO: 2 or at a position corresponding thereto;
(am') L, I or F at position 109 of the amino acid sequence as shown in SEQ ID NO: 2 or at a position corresponding thereto;
(an') L or W at position 113 of the amino acid sequence as shown in SEQ ID NO: 2 or at a position corresponding thereto;
(ao') G, S, T, C, N, Q, D, E, R, K, H, A, V, M, W, F or P at position 119 of the amino acid sequence as shown in SEQ ID NO: 2 or at a position corresponding thereto;
(ap') Y, R, I, W or F at position 120 of the amino acid sequence as shown in SEQ ID NO: 2 or at a position corresponding thereto;
(aq') K or A at position 124 of the amino acid sequence as shown in SEQ ID NO: 2 or at a position corresponding thereto;
(ar') S, T, N, Q, D, I or M at position 132 of the amino acid sequence as shown in SEQ ID NO: 2 or at a position corresponding thereto;
(as') G, S, T, C, N, Q, D, E, R, K, H, V, L, I, M, W, F or P at position 133 of the amino acid sequence as shown in SEQ ID NO: 2 or at a position corresponding thereto;
(at') G, S, T or A at position 134 of the amino acid sequence as shown in SEQ ID NO: 2 or at a position corresponding thereto;
(au') G, S, T, N, Q, Y, R, K, H, A, L, I, M or W between position 133 of the amino acid sequence as shown in SEQ ID NO: 2 or a position corresponding thereto, and position 134 thereof or a position corresponding thereto;

(av') R, A, L or M at position 135 of the amino acid sequence as shown in SEQ ID NO: 2 or at a position corresponding thereto;

(aw') S, T, C, Q, Y, D, E, R, K, H, A, V, L, I, M, W, F or P at position 136 of the amino acid sequence as shown in SEQ ID NO: 2 or at a position corresponding thereto;

(ax') G, S, C, N, Q, D, E, R, K, H, A, V, M, W, F or P at position 138 of the amino acid sequence as shown in SEQ ID NO: 2 or at a position corresponding thereto;

(ay') L, W or F at position 140 of the amino acid sequence as shown in SEQ ID NO: 2 or at a position corresponding thereto;

(az') G, S, T, C, N, Q, D, E, R, K, H, A, M, W, F or P at position 148 of the amino acid sequence as shown in SEQ ID NO: 2 or at a position corresponding thereto;

(ba') F at position 151 of the amino acid sequence as shown in SEQ ID NO: 2 or at a position corresponding thereto;

(bb') S, T, N, Q, D, K, H, V, L, I or F at position 163 of the amino acid sequence as shown in SEQ ID NO: 2 or at a position corresponding thereto;

(bc') G, V, L, I, W or F at position 166 of the amino acid sequence as shown in SEQ ID NO: 2 or at a position corresponding thereto;

(bd') V at position 167 of the amino acid sequence as shown in SEQ ID NO: 2 or at a position corresponding thereto;

(be') V or L at position 170 of the amino acid sequence as shown in SEQ ID NO: 2 or at a position corresponding thereto;

(bf) G, T, E or A at position 171 of the amino acid sequence as shown in SEQ ID NO: 2 or at a position corresponding thereto;

(bg') S at position 187 of the amino acid sequence as shown in SEQ ID NO: 2 or at a position corresponding thereto;

(bh') V, L, I, W or F at position 191 of the amino acid sequence as shown in SEQ ID NO: 2 or at a position corresponding thereto;

(bi') S, T, C, Q, Y, D, E, R, K, H, A, V, L, I, M, W, F or P at position 193 of the amino acid sequence as shown in SEQ ID NO: 2 or at a position corresponding thereto;

(bj') Y, R or K at position 194 of the amino acid sequence as shown in SEQ ID NO: 2 or at a position corresponding thereto;

(bk') G, S, T, C, N, Q, D, E, R, K, H, A, V, L, I, M, W, F or P at position 195 of the amino acid sequence as shown in SEQ ID NO: 2 or at a position corresponding thereto;

(bl') W at position 200 of the amino acid sequence as shown in SEQ ID NO: 2 or at a position corresponding thereto;

(bm') D, E or Q at position 201 of the amino acid sequence as shown in SEQ ID NO: 2 or at a position corresponding thereto;

(bn') E at position 202 of the amino acid sequence as shown in SEQ ID NO: 2 or at a position corresponding thereto;

(bo') S, T, C, N, D, E, R, K, H, V, L, I, M, W or P at position 204 of the amino acid sequence as shown in SEQ ID NO: 2 or at a position corresponding thereto;

(bp') S, T, C, N, Q, Y, E, K, H, A, V, L, I, M or W at position 205 of the amino acid sequence as shown in SEQ ID NO: 2 or at a position corresponding thereto;

(bq') N, Q, R, V, L or W at position 212 of the amino acid sequence as shown in SEQ ID NO: 2 or at a position corresponding thereto;

(br') Y at position 226 of the amino acid sequence as shown in SEQ ID NO: 2 or at a position corresponding thereto;

(bs') L, I or W at position 233 of the amino acid sequence as shown in SEQ ID NO: 2 or at a position corresponding thereto;

(bt') N at position 237 of the amino acid sequence as shown in SEQ ID NO: 2 or at a position corresponding thereto;

(bu') L at position 238 of the amino acid sequence as shown in SEQ ID NO: 2 or at a position corresponding thereto;

(bv') Y, L or I at position 243 of the amino acid sequence as shown in SEQ ID NO: 2 or at a position corresponding thereto;

(bw') N at position 245 of the amino acid sequence as shown in SEQ ID NO: 2 or at a position corresponding thereto;

(bx') Y, V, L, W or F at position 246 of the amino acid sequence as shown in SEQ ID NO: 2 or at a position corresponding thereto;

(by') S, T, C, N, Q, E, H, A, V, L, I, M, W or F at position 247 of the amino acid sequence as shown in SEQ ID NO: 2 or at a position corresponding thereto;

(bz') F at position 248 of the amino acid sequence as shown in SEQ ID NO: 2 or at a position corresponding thereto;

(ca') F at position 250 of the amino acid sequence as shown in SEQ ID NO: 2 or at a position corresponding thereto;

(cb') G, T, N, Q, D, A, V, L or I at position 251 of the amino acid sequence as shown in SEQ ID NO: 2 or at a position corresponding thereto;

(cc') S, T, C, Q, Y, D, E, R, K, H, A, V, L, I, W, F or P at position 256 of the amino acid sequence as shown in SEQ ID NO: 2 or at a position corresponding thereto;

(cd') V or I at position 257 of the amino acid sequence as shown in SEQ ID NO: 2 or at a position corresponding thereto;

(ce') G, S, T, C, Q, D, E, A, V, L, I or M at position 264 of the amino acid sequence as shown in SEQ ID NO: 2 or at a position corresponding thereto;

(cf') G, T or I at position 273 of the amino acid sequence as shown in SEQ ID NO: 2 or at a position corresponding thereto;

(cg') L, W or F at position 275 of the amino acid sequence as shown in SEQ ID NO: 2 or at a position corresponding thereto;

(ch') V, L, I or F at position 277 of the amino acid sequence as shown in SEQ ID NO: 2 or at a position corresponding thereto;

(ci') R the amino acid residue at position 281 of the amino acid as shown in SEQ ID NO: 2 or at a position corresponding thereto;

(cj') T the amino acid residue at position 294 of the amino acid as shown in SEQ ID NO: 2 or at a position corresponding thereto;

(ck') V at position 296 of the amino acid sequence as shown in SEQ ID NO: 2 or at a position corresponding thereto;

(cl') L, W or F at position 297 of the amino acid sequence as shown in SEQ ID NO: 2 or at a position corresponding thereto;

(cm') S or A at position 304 of the amino acid sequence as shown in SEQ ID NO: 2 or at a position corresponding thereto;
(cn') N at position 313 of the amino acid sequence as shown in SEQ ID NO: 2 or at a position corresponding thereto;
(co') S, T, C, N, Q, Y, D, E, R, K, H, V, L, I, M, W, F or P at position 319 of the amino acid sequence as shown in SEQ ID NO: 2 or at a position corresponding thereto;
(cp') G, T, V, L, I or F at position 320 of the amino acid sequence as shown in SEQ ID NO: 2 or at a position corresponding thereto;
(cq') W at position 326 of the amino acid sequence as shown in SEQ ID NO: 2 or at a position corresponding thereto;
(cr') M, W or F at position 330 of the amino acid sequence as shown in SEQ ID NO: 2 or at a position corresponding thereto;
(cs') G, T or V at position 332 of the amino acid sequence as shown in SEQ ID NO: 2 or at a position corresponding thereto;
(ct') L at position 334 of the amino acid sequence as shown in SEQ ID NO: 2 or at a position corresponding thereto;
(cu') F at position 335 of the amino acid sequence as shown in SEQ ID NO: 2 or at a position corresponding thereto;
(cv') G, S, T, C, Q, R, K, H, A or V at position 337 of the amino acid sequence as shown in SEQ ID NO: 2 or at a position corresponding thereto;
(cw') S, T, C, Q, Y, D, E, R, K, H, A, V, L, I, M, W, F or P at position 342 of the amino acid sequence as shown in SEQ ID NO: 2 or at a position corresponding thereto;
(cx') T at position 343 of the amino acid sequence as shown in SEQ ID NO: 2 or at a position corresponding thereto;
(cy') R at position 346 of the amino acid sequence as shown in SEQ ID NO: 2 or at a position corresponding thereto;
(cz') L at position 357 of the amino acid sequence as shown in SEQ ID NO: 2 or at a position corresponding thereto;
(da') G, S, Q, V, L, I or F at position 359 of the amino acid sequence as shown in SEQ ID NO: 2 or at a position corresponding thereto;
(db') V, I or W at position 361 of the amino acid sequence as shown in SEQ ID NO: 2 or at a position corresponding thereto;
(dc') N at position 369 of the amino acid sequence as shown in SEQ ID NO: 2 or at a position corresponding thereto;
(dd') W at position 376 of the amino acid sequence as shown in SEQ ID NO: 2 or at a position corresponding thereto;
(de') L or W at position 378 of the amino acid sequence as shown in SEQ ID NO: 2 or at a position corresponding thereto;
(df') D, E, R or K at position 379 of the amino acid sequence as shown in SEQ ID NO: 2 or at a position corresponding thereto;
(dg') F at position 380 of the amino acid sequence as shown in SEQ ID NO: 2 or at a position corresponding thereto;
(dh') Y, M or P at position 385 of the amino acid sequence as shown in SEQ ID NO: 2 or at a position corresponding thereto;
(di') A, L, I or M at position 386 of the amino acid sequence as shown in SEQ ID NO: 2 or at a position corresponding thereto;
(dj') G, Q, E, R, K, H, A, V, L, I, M, W or F at position 387 of the amino acid sequence as shown in SEQ ID NO: 2 or at a position corresponding thereto;
(dk') G, S, T, Y or F at position 390 of the amino acid sequence as shown in SEQ ID NO: 2 or at a position corresponding thereto;
(dl') Q at position 393 of the amino acid sequence as shown in SEQ ID NO: 2 or at a position corresponding thereto;
(dm') G at position 396 of the amino acid sequence as shown in SEQ ID NO: 2 or at a position corresponding thereto;
(dn') T or K at position 403 of the amino acid sequence as shown in SEQ ID NO: 2 or at a position corresponding thereto;
(do') D, V, L, I, W, F or P at position 405 of the amino acid sequence as shown in SEQ ID NO: 2 or at a position corresponding thereto;
(dp') V, W or F at position 406 of the amino acid sequence as shown in SEQ ID NO: 2 or at a position corresponding thereto;
(dq') G or C at position 407 of the amino acid sequence as shown in SEQ ID NO: 2 or at a position corresponding thereto;
(dr') N, Y, I or W at position 408 of the amino acid sequence as shown in SEQ ID NO: 2 or at a position corresponding thereto;
(ds') Y or W at position 409 of the amino acid sequence as shown in SEQ ID NO: 2 or at a position corresponding thereto;
(dt') A, V, L or P at position 411 of the amino acid sequence as shown in SEQ ID NO: 2 or at a position corresponding thereto;
(du') R or V at position 427 of the amino acid sequence as shown in SEQ ID NO: 2 or at a position corresponding thereto; and
(dv') L at position 433 of the amino acid sequence as shown in SEQ ID NO: 2 or at a position corresponding thereto,
(ii) more preferably has any of the following amino acid residue or a combination thereof:
the (ar');
the (bk');
the (bm');
the (cj');
the (cm');
the (dc');
a combination of the (e') and (aa');
a combination of the (bc') and (bd');
a combination of the (bm') and (bn');
a combination of the (bm') and (cm');
a combination of the (bm'), (bn') and (cm');
a combination of the (d'), (bm') and (cm');
a combination of the (d'), (bm'), (bn') and (cm');
a combination of the (v'), (cf'), (da') and (dj');
a combination of the (j'), (s'), (y'), (bh') and (do');
a combination of the (as'), (at') and (au');
a combination of the (e'), (v'), (aa'), (bc'), (bd'), (bk'), (cf'), (da'), (dc') and (dj');
a combination of the (e'), (v'), (aa'), (ar'), (bc'), (bd'), (bk'), (cf'), (da'), (dc') and (dj');
a combination of the (j'), (s'), (v'), (y'), (as'), (at'), (au'), (bc'), (bd'), (bh'), (bk'), (cf'), (da'), (dc'), (dj') and (do');

a combination of the (v'), (aa'), (ar'), (bc'), (bd'), (bk'), (cf'), (da'), (dc') and (dj');
a combination of the (v'), (as'), (at'), (au'), (bc'), (bd'), (bk'), (cf'), (da'), (dc') and (dj');
a combination of the (e'), (v'), (aa'), (bc'), (bd'), (bk'), (bo'), (cf'), (co'), (da'), (dc') and (dj');
a combination of the (v'), (as'), (at'), (au'), (bc'), (bd'), (bj'), (bk'), (bq'), (cf'), (da'), (dc'), (df') and (dj');
a combination of the (e'), (v'), (aa'), (ar'), (bc'), (bd'), (bk'), (cf'), (cj'), (da'), (dc') and (dj');
a combination of the (e'), (v'), (z'), (aa'), (ar'), (bc'), (bd'), (bk'), (bo'), (cf'), (cj'), (da'), (dc') and (dj');
a combination of the (e'), (v'), (z'), (aa'), (ar'), (bc'), (bd'), (bk'), (bm'), (bn'), (bo'), (cf'), (cj'), (da'), (dc') and (dj');
a combination of the (e'), (v'), (z'), (aa'), (ar'), (bc'), (bd'), (bk'), (bm'), (bo'), (cf'), (cj'), (cm'), (da'), (dc'), and (dj');
a combination of the (e'), (v'), (z'), (aa'), (ar'), (bc'), (bd'), (bk'), (bm'), (bn'), (bo'), (cf'), (cj'), (cm'), (da'), (dc') and (dj');
a combination of the (d'), (e'), (v'), (z'), (aa'), (ar'), (bc'), (bd'), (bk'), (bm'), (bo'), (cf'), (cj'), (cm'), (da'), (dc') and (dj'); and
a combination of the (d'), (e'), (v'), (z'), (aa'), (ar'), (bc'), (bd'), (bk'), (bm'), (bn'), (bo'), (cf'), (cj'), (cm'), (da'), (dc') and (dj'), and (iii) more preferably has one or more amino acid residues selected from the following (dl'), (bm1'), (bn1') and (cm1'):

(d1') D or E at a position corresponding to position 15 of SEQ ID NO:2;
(bm1') D or E at a position corresponding to position 201 of SEQ ID NO:2;
(bn1') E at a position corresponding to position 202 of SEQ ID NO:2; and
(cm1') A at a position corresponding to position 304 of SEQ ID NO:2.

[3] The mutant protease according to [1], which preferably consists of an amino acid sequence having an identity of at least 90% with the amino acid sequence as shown in SEQ ID NO:2 and has any of the following amino acid residue 1) to 10):

1) E at a position corresponding to position 303 of SEQ ID NO:2, and A at a position corresponding to position 304 of SEQ ID NO:2;
2) E at a position corresponding to position 303 of SEQ ID NO:2, D at a position corresponding to position 201 of SEQ ID NO:2, and A at a position corresponding to position 304 of SEQ ID NO:2;
3) E at a position corresponding to position 303 of SEQ ID NO:2, D or E at a position corresponding to position 15 of SEQ ID NO:2, D at a position corresponding to position 201 of SEQ ID NO:2, and A at a position corresponding to position 304 of SEQ ID NO: 2;
4) E at a position corresponding to position 303 of SEQ ID NO:2, D at a position corresponding to position 201 of SEQ ID NO:2, E at a position corresponding to position 202 of SEQ ID NO:2, and A at a position corresponding to position 304 of SEQ ID NO: 2;
5) E at a position corresponding to position 303 of SEQ ID NO:2, D or E at a position corresponding to position 15 of SEQ ID NO:2, D at a position corresponding to position 201 of SEQ ID NO:2, E at a position corresponding to position 202 of SEQ ID NO:2, and A at a position corresponding to position 304 of SEQ ID NO:2;
6) N at a position corresponding to position 303 of SEQ ID NO:2, and A at a position corresponding to position 304 of SEQ ID NO:2;
7) N at a position corresponding to 303 of SEQ ID NO:2, D at a position corresponding to position 201 of SEQ ID NO:2, and A at a position corresponding to position 304 of SEQ ID NO:2;
8) N at a position corresponding to position 303 of SEQ ID NO:2, D or E at a position corresponding to position 15 of SEQ ID NO:2, D at a position corresponding to position 201 of SEQ ID NO:2, and A at a position corresponding to position 304 of SEQ ID NO: 2;
9) N at a position corresponding to position 303 of SEQ ID NO:2, D at a position corresponding to position 201 of SEQ ID NO:2, E at a position corresponding to position 202 of SEQ ID NO:2, and A at a position corresponding to position 304 of SEQ ID NO: 2; and
10) N at a position corresponding to position 303 of SEQ ID NO:2, D or E at a position corresponding to position 15 of SEQ ID NO:2, D at a position corresponding to position 201 of SEQ ID NO:2, E at a position corresponding to position 202 of SEQ ID NO:2, and A at a position corresponding to position 304 of SEQ ID NO:2.

[4] The mutant protease according to any one of [1] to [3], which preferably has aspartic acid at a position corresponding to position 30 of SEQ ID NO:2, histidine at a position corresponding to position 68 thereof, and serine at a position corresponding to position 255 thereof,
more preferably has the amino acid residues shown in the above described Table 1 (ii) at positions corresponding to the positions shown in the above described Table 1 (i) in the amino acid sequence as shown in SEQ ID NO: 2.

[5] The mutant protease according to any one of [1] to [4], which has improved stability under acidic condition in comparison to a parent protease.

[6] The mutant protease according to [5], wherein the parent protease is
preferably a protease that consists of the amino acid sequence as shown in SEQ ID NO: 2 or an amino acid sequence having an identity of at least 90% therewith,
more preferably a protease that consists of an amino acid sequence having an identity of at least 90% with the amino acid sequence as shown in SEQ ID No:2 and that has glycine at a position corresponding to position 303 of the amino acid sequence as shown in SEQ ID NO:2,
further more preferably a protease that consists of any of the amino acid sequences as shown in SEQ ID Nos: 2 to 4.

[7] The mutant protease according to [5] or [6], wherein the acidic condition is preferably weakly acidic condition, more preferably condition of pH 5 or more, further more preferably condition of pH 5 or more and less than pH 7, further more preferably condition of from pH 6 to pH 6.8.

[8] A polynucleotide encoding the mutant protease according to any one of [1] to [7].

[9] A vector comprising the polynucleotide according to [8].

[10] A transformant comprising the polynucleotide according to [8] or the vector according to [9].

[11] The vector according to [9] or the transformant according to [10], wherein the vector is preferably an expression vector capable of inducing expression of an introduced gene in a bacterium of *Bacillus* sp.

[12] The transformant according to the above [10] or [11], which is preferably a recombinant bacterium of *Bacillus* sp.

[13] A method for producing a mutant protease, comprising, using the transformant according to [10] to [12].

[14] A detergent composition comprising the mutant protease according to any one of [1] to [7].

[15] The detergent composition according to [14], which is preferably weakly acidic.

[16] The detergent composition according to [14] or [15], which is preferably a liquid detergent composition.

[17] The detergent composition according to [16], wherein the content of a surfactant is preferably from 10% to 80% by mass, more preferably from 30% to 70% by mass.

[18] A method for producing a mutant protease, comprising substituting the amino acid residue at a position corresponding to position 303 of the amino acid sequence as shown in SEQ ID NO:2 with another amino acid residue in the amino acid sequence as shown in SEQ ID No:2 or an amino acid sequence having an identity of at least 90% therewith, wherein the another amino acid residue is as follows:

an amino acid residue selected from the group of consisting of aspartic acid, glutamic acid, phenylalanine, histidine, isoleucine, methionine, asparagine, proline, glutamine, threonine, valine, tryptophan, and tyrosine, preferably an amino acid residue selected from the group of consisting of aspartic acid, glutamic acid, phenylalanine, isoleucine, methionine, asparagine, glutamine, valine, tryptophan, and tyrosine, more preferably an amino acid residue selected from the group of consisting of aspartic acid, glutamic acid, isoleucine, methionine, asparagine, and valine.

[19] A method for improving the stability of protease under acidic condition, comprising substituting the amino acid residue at a position corresponding to position 303 of the amino acid sequence as shown in SEQ ID NO:2 with another amino acid residue in the amino acid sequence as shown in SEQ ID No:2 or an amino acid sequence having an identity of at least 90% therewith, wherein the another amino acid residue is as follows:

an amino acid residue selected from the group of consisting of aspartic acid, glutamic acid, phenylalanine, histidine, isoleucine, methionine, asparagine, proline, glutamine, threonine, valine, tryptophan, and tyrosine, preferably an amino acid residue selected from the group of consisting of aspartic acid, glutamic acid, phenylalanine, isoleucine, methionine, asparagine, glutamine, valine, tryptophan, and tyrosine, more preferably an amino acid residue selected from the group of consisting of aspartic acid, glutamic acid, isoleucine, methionine, asparagine, and valine.

[20] The method according to [18] or [19], wherein the amino acid sequence as shown in SEQ ID NO:2 or the amino acid sequence having an identity of at least 90% therewith has glycine at a position corresponding to position 303 of the amino acid sequence as shown in SEQ ID NO:2.

[21] The method according to any one of [18] to [20], wherein the method preferably comprises, in addition to substitution of an amino acid residue at a position corresponding to position 303 of the amino acid sequence as shown in SEQ ID NO:2 in the amino acid sequence as shown in SEQ ID No:2, introducing a mutation other than the substitution at position 303, or the amino acid sequence having an identity of at least 90% with the amino acid sequence as shown in SEQ ID NO:2 has a mutation other than the substitution at position 303 with respect to the amino acid sequence as shown in SEQ ID NO:2, wherein the mutation other than the substitution at position 303 is as follows:

(i) preferably, one or more mutations selected from the group consisting of the following mutations (a) to (dv):

(a) substitution of G at position 6 of the amino acid sequence as shown in SEQ ID NO:2 or at a position corresponding thereto with S, T, C, Q, Y, R, K, H, A, V, L, I, M, W or F;

(b) substitution of K at position 9 of the amino acid sequence as shown in SEQ ID NO:2 or at a position corresponding thereto with Q;

(c) substitution of D at position 11 of the amino acid sequence as shown in SEQ ID NO:2 or at a position corresponding thereto with G, S or N;

(d) substitution of S at position 15 of the amino acid sequence as shown in SEQ ID NO:2 or at a position corresponding thereto with H, C, Q, D, E, R, A, V, M, W or F;

(e) substitution of S at position 16 of the amino acid sequence as shown in SEQ ID NO:2 or at a position corresponding thereto with T, Q, V, C, Y, D, E, R, K, H, L, I, M, W or F;

(f) substitution of Y at position 20 of the amino acid sequence as shown in SEQ ID NO:2 or at a position corresponding thereto with F or A;

(g) substitution of Q at position 22 of the amino acid sequence as shown in SEQ ID NO:2 or at a position corresponding thereto with W;

(h) substitution of G at position 23 of the amino acid sequence as shown in SEQ ID NO:2 or at a position corresponding thereto with N;

(i) substitution of R at position 37 of the amino acid sequence as shown in SEQ ID NO:2 or at a position corresponding thereto with T;

(j) substitution of S at position 40 of the amino acid sequence as shown in SEQ ID NO:2 or at a position corresponding thereto with V, L, I, W or F;

(k) substitution of S at position 41 of the amino acid sequence as shown in SEQ ID NO:2 or at a position corresponding thereto with I;

(l) substitution of F at position 46 of the amino acid sequence as shown in SEQ ID NO:2 or at a position corresponding thereto with S, T, C, N, Q, Y, E, K, H, A, V, L, I, M or W;

(m) substitution of K at position 49 of the amino acid sequence as shown in SEQ ID NO: 2 or at a position corresponding thereto with Q;

(n) substitution of A at position 52 of the amino acid sequence as shown in SEQ ID NO:2 or at a position corresponding thereto with G or S;

(o) substitution of L at position 53 of the amino acid sequence as shown in SEQ ID NO:2 or at a position corresponding thereto with A, V or I;

(p) substitution of Y at position 54 of the amino acid sequence as shown in SEQ ID NO:2 or at a position corresponding thereto with G, S, T, C, N, Q, D, E, R, H, A, V, M, W, F or P;

(q) substitution of L at position 56 of the amino acid sequence as shown in SEQ ID NO:2 or at a position corresponding thereto with V;
(r) substitution of G at position 57 of the amino acid sequence as shown in SEQ ID NO:2 or at a position corresponding thereto with S, T, C, Q, D, E, R, K, H, A, V, L, I, M, W, F or P;
(s) substitution of T at position 59 of the amino acid sequence as shown in SEQ ID NO:2 or at a position corresponding thereto with V, L, I, M, W or F;
(t) substitution of N at position 60 of the amino acid sequence as shown in SEQ ID NO:2 or at a position corresponding thereto with V, L, I, W or F;
(u) substitution of N at position 63 of the amino acid sequence as shown in SEQ ID NO:2 or at a position corresponding thereto with S, D or L;
(v) substitution of T at position 65 of the amino acid sequence as shown in SEQ ID NO:2 or at a position corresponding thereto with W or P;
(w) substitution of N at position 66 of the amino acid sequence as shown in SEQ ID NO: 2 or at a position corresponding thereto with G, S, T, C, Q, D, E, H, A, V, L, I, M or W;
(x) substitution of G at position 80 of the amino acid sequence as shown in SEQ ID NO:2 or at a position corresponding thereto with H or A;
(y) substitution of S at position 81 of the amino acid sequence as shown in SEQ ID NO:2 or at a position corresponding thereto with Q, Y, L, I, W or F;
(z) substitution of T at position 82 of the amino acid sequence as shown in SEQ ID NO:2 or at a position corresponding thereto with G, S, C, Q, D, E, R, K, H, A or M;
(aa) substitution of N at position 83 of the amino acid sequence as shown in SEQ ID NO: 2 or at a position corresponding thereto with S, C or A;
(ab) substitution of K at position 84 of the amino acid sequence as shown in SEQ ID NO: 2 or at a position corresponding thereto with R;
(ac) substitution of Q at position 89 of the amino acid sequence as shown in SEQ ID NO: 2 or at a position corresponding thereto with H;
(ad) substitution of N at position 91 of the amino acid sequence as shown in SEQ ID NO: 2 or at a position corresponding thereto with C;
(ae) substitution of S at position 100 of the amino acid sequence as shown in SEQ ID NO: 2 or at a position corresponding thereto with L, I, W or F;
(af) substitution of G at position 101 of the amino acid sequence as shown in SEQ ID NO: 2 or at a position corresponding thereto with S, T, C, N, Q, Y, D, E, R, K, H, A, V, L, I, M, W, F or P;
(ag) substitution of G at position 102 of the amino acid sequence as shown in SEQ ID NO: 2 or at a position corresponding thereto with S, T, C, Q, Y, D, E, R, K, H, A, V, L, I, M, W, F or P;
(ah) substitution of G at position 103 of the amino acid sequence as shown in SEQ ID NO: 2 or at a position corresponding thereto with S, T, C, Q, Y, D, E, R, K, H, A, V, L, I, M, W, F or P;
(ai) substitution of L at position 104 of the amino acid sequence as shown in SEQ ID NO: 2 or at a position corresponding thereto with S, T, C, Q, Y, D, E, R, K, H, A, V, L, I, M, W, F or P;

(aj) substitution of G at position 105 of the amino acid sequence as shown in SEQ ID NO: 2 or at a position corresponding thereto with S, T, C, Q, Y, D, E, R, K, H, A, V, L, I, M, W, F or P;
(ak) substitution of G at position 106 of the amino acid sequence as shown in SEQ ID NO: 2 or at a position corresponding thereto with S, T, C, Q, Y, D, E, R, K, H, A, V, L, I, M, W, F or P;
(al) substitution of L at position 107 of the amino acid sequence as shown in SEQ ID NO: 2 or at a position corresponding thereto with S, R, K or A;
(am) substitution of S at position 109 of the amino acid sequence as shown in SEQ ID NO: 2 or at a position corresponding thereto with L, I or F;
(an) substitution of T at position 113 of the amino acid sequence as shown in SEQ ID NO: 2 or at a position corresponding thereto with L or W;
(ao) substitution of Y at position 119 of the amino acid sequence as shown in SEQ ID NO: 2 or at a position corresponding thereto with G, S, T, C, N, Q, D, E, R, K, H, A, V, M, W, F or P;
(ap) substitution of S at position 120 of the amino acid sequence as shown in SEQ ID NO: 2 or at a position corresponding thereto with Y, R, I, W or F;
(aq) substitution of R at position 124 of the amino acid sequence as shown in SEQ ID NO: 2 or at a position corresponding thereto with K or A;
(ar) substitution of A at position 132 of the amino acid sequence as shown in SEQ ID NO: 2 or at a position corresponding thereto with S, T, N, Q, D, I or M;
(as) substitution of A at position 133 of the amino acid sequence as shown in SEQ ID NO: 2 or at a position corresponding thereto with G, S, T, C, N, Q, D, E, R, K, H, V, L, I, M, W, F or P;
(at) substitution of V at position 134 of the amino acid sequence as shown in SEQ ID NO: 2 or at a position corresponding thereto with G, S, T or A;
(au) insertion of G, S, T, N, Q, Y, R, K, H, A, L, I, M or W into a site between position 133 of the amino acid sequence as shown in SEQ ID NO:2 or a position corresponding thereto and position 134 thereof or a position corresponding thereto;
(av) substitution of N at position 135 of the amino acid sequence as shown in SEQ ID NO: 2 or at a position corresponding thereto with R, A, L or M;
(aw) substitution of G at position 136 of the amino acid sequence as shown in SEQ ID NO: 2 or at a position corresponding thereto with S, T, C, Q, Y, D, E, R, K, H, A, V, L, I, M, W, F or P;
(ax) substitution of Y at position 138 of the amino acid sequence as shown in SEQ ID NO: 2 or at a position corresponding thereto with G, S, C, N, Q, D, E, R, K, H, A, V, M, W, F or P;
(ay) substitution of T at position 140 of the amino acid sequence as shown in SEQ ID NO: 2 or at a position corresponding thereto with L, W or F;
(az) substitution of Y at position 148 of the amino acid sequence as shown in SEQ ID NO: 2 or at a position corresponding thereto with G, S, T, C, N, Q, D, E, R, K, H, A, M, W, F or P;
(ba) substitution of K at position 151 of the amino acid sequence as shown in SEQ ID NO: 2 or at a position corresponding thereto with F;
(bb) substitution of E at position 163 of the amino acid sequence as shown in SEQ ID NO: 2 or at a position corresponding thereto with S, T, N, Q, D, K, H, V, L, I or F;

(bc) substitution of N at position 166 of the amino acid sequence as shown in SEQ ID NO: 2 or at a position corresponding thereto with G, V, L, I, W or F;

(bd) substitution of G at position 167 of the amino acid sequence as shown in SEQ ID NO: 2 or at a position corresponding thereto with V;

(be) substitution of I at position 170 of the amino acid sequence as shown in SEQ ID NO: 2 or at a position corresponding thereto with V or L;

(bf) substitution of S at position 171 of the amino acid sequence as shown in SEQ ID NO: 2 or at a position corresponding thereto with G, T, E or A;

(bg) substitution of N at position 187 of the amino acid sequence as shown in SEQ ID NO: 2 or at a position corresponding thereto with S;

(bh) substitution of S at position 191 of the amino acid sequence as shown in SEQ ID NO: 2 or at a position corresponding thereto with V, L, I, W or F;

(bi) substitution of G at position 193 of the amino acid sequence as shown in SEQ ID NO: 2 or at a position corresponding thereto with S, T, C, Q, Y, D, E, R, K, H, A, V, L, I, M, W, F or P;

(bj) substitution of S at position 194 of the amino acid sequence as shown in SEQ ID NO: 2 or at a position corresponding thereto with Y, R or K;

(bk) substitution of Y at position 195 of the amino acid sequence as shown in SEQ ID NO: 2 or at a position corresponding thereto with G, S, T, C, N, Q, D, E, R, K, H, A, V, L, I, M, W, F or P;

(bl) substitution of N at position 200 of the amino acid sequence as shown in SEQ ID NO: 2 or at a position corresponding thereto with W;

(bm) substitution of H at position 201 of the amino acid sequence as shown in SEQ ID NO: 2 or at a position corresponding thereto with D, E or Q;

(bn) substitution of V at position 202 of the amino acid sequence as shown in SEQ ID NO: 2 or at a position corresponding thereto with E;

(bo) substitution of Q at position 204 of the amino acid sequence as shown in SEQ ID NO: 2 or at a position corresponding thereto with S, T, C, N, D, E, R, K, H, V, L, I, M, W or P;

(bp) substitution of F at position 205 of the amino acid sequence as shown in SEQ ID NO: 2 or at a position corresponding thereto with S, T, C, N, Q, Y, E, K, H, A, V, L, I, M or W;

(bq) substitution of K at position 212 of the amino acid sequence as shown in SEQ ID NO: 2 or at a position corresponding thereto with N, Q, R, V, L or W;

(br) substitution of F at position 226 of the amino acid sequence as shown in SEQ ID NO: 2 or at a position corresponding thereto with Y;

(bs) substitution of S at position 233 of the amino acid sequence as shown in SEQ ID NO: 2 or at a position corresponding thereto with L, I or W;

(bt) substitution of D at position 237 of the amino acid sequence as shown in SEQ ID NO: 2 or at a position corresponding thereto with N;

(bu) substitution of S at position 238 of the amino acid sequence as shown in SEQ ID NO: 2 or at a position corresponding thereto with L;

(bv) substitution of N at position 243 of the amino acid sequence as shown in SEQ ID NO: 2 or at a position corresponding thereto with Y, L or I;

(bw) substitution of D at position 245 of the amino acid sequence as shown in SEQ ID NO: 2 or at a position corresponding thereto with N;

(bx) substitution of S at position 246 of the amino acid sequence as shown in SEQ ID NO: 2 or at a position corresponding thereto with Y, V, L, W or F;

(by) substitution of K at position 247 of the amino acid sequence as shown in SEQ ID NO: 2 or at a position corresponding thereto with S, T, C, N, Q, E, H, A, V, L, I, M, W or F;

(bz) substitution of Y at position 248 of the amino acid sequence as shown in SEQ ID NO: 2 or at a position corresponding thereto with F;

(ca) substitution of Y at position 250 of the amino acid sequence as shown in SEQ ID NO: 2 or at a position corresponding thereto with F;

(cb) substitution of M at position 251 of the amino acid sequence as shown in SEQ ID NO: 2 or at a position corresponding thereto with G, T, N, Q, D, A, V, L or I;

(cc) substitution of M at position 256 of the amino acid sequence as shown in SEQ ID NO: 2 or at a position corresponding thereto with S, T, C, Q, Y, D, E, R, K, H, A, V, L, I, W, F or P;

(cd) substitution of A at position 257 of the amino acid sequence as shown in SEQ ID NO: 2 or at a position corresponding thereto with V or I;

(ce) substitution of N at position 264 of the amino acid sequence as shown in SEQ ID NO: 2 or at a position corresponding thereto with G, S, T, C, Q, D, E, A, V, L, I or M;

(cf) substitution of V at position 273 of the amino acid sequence as shown in SEQ ID NO: 2 or at a position corresponding thereto with G, T or I;

(cg) substitution of N at position 275 of the amino acid sequence as shown in SEQ ID NO: 2 or at a position corresponding thereto with L, W or F;

(ch) substitution of G at position 277 of the amino acid sequence as shown in SEQ ID NO: 2 or at a position corresponding thereto with V, L, I or F;

(ci) substitution of K at position 281 of the amino acid sequence as shown in SEQ ID NO: 2 or at a position corresponding thereto with R;

(cj) substitution of A at position 294 of the amino acid sequence as shown in SEQ ID NO: 2 or at a position corresponding thereto with T;

(ck) substitution of I at position 296 of the amino acid sequence as shown in SEQ ID NO: 2 or at a position corresponding thereto with V;

(cl) substitution of G at position 297 of the amino acid sequence as shown in SEQ ID NO: 2 or at a position corresponding thereto with L, W or F;

(cm) substitution of N at position 304 of the amino acid sequence as shown in SEQ ID NO: 2 or at a position corresponding thereto with S or A;

(cn) substitution of D at position 313 of the amino acid sequence as shown in SEQ ID NO: 2 or at a position corresponding thereto with N;

(co) substitution of A at position 319 of the amino acid sequence as shown in SEQ ID NO: 2 or at a position corresponding thereto with S, T, C, N, Q, Y, D, E, R, K, H, V, L, I, M, W, F or P;

(cp) substitution of Y at position 320 of the amino acid sequence as shown in SEQ ID NO: 2 or at a position corresponding thereto with G, T, V, L, I or F;

(cq) substitution of S at position 326 of the amino acid sequence as shown in SEQ ID NO: 2 or at a position corresponding thereto with W;

(cr) substitution of S at position 330 of the amino acid sequence as shown in SEQ ID NO: 2 or at a position corresponding thereto with M, W or F;
(cs) substitution of K at position 332 of the amino acid sequence as shown in SEQ ID NO: 2 or at a position corresponding thereto with G, T or V;
(ct) substitution of T at position 334 of the amino acid sequence as shown in SEQ ID NO: 2 or at a position corresponding thereto with L;
(cu) substitution of Y at position 335 of the amino acid sequence as shown in SEQ ID NO: 2 or at a position corresponding thereto with F;
(cv) substitution of F at position 337 of the amino acid sequence as shown in SEQ ID NO: 2 or at a position corresponding thereto with G, S, T, C, Q, R, K, H, A or V;
(cw) substitution of G at position 342 of the amino acid sequence as shown in SEQ ID NO: 2 or at a position corresponding thereto with S, T, C, Q, Y, D, E, R, K, H, A, V, L, I, M, W, F or P;
(cx) substitution of K at position 343 of the amino acid sequence as shown in SEQ ID NO: 2 or at a position corresponding thereto with T;
(cy) substitution of K at position 346 of the amino acid sequence as shown in SEQ ID NO: 2 or at a position corresponding thereto with R;
(cz) substitution of S at position 357 of the amino acid sequence as shown in SEQ ID NO: 2 or at a position corresponding thereto with L;
(da) substitution of T at position 359 of the amino acid sequence as shown in SEQ ID NO: 2 or at a position corresponding thereto with G, S, Q, V, L, I or F;
(db) substitution of S at position 361 of the amino acid sequence as shown in SEQ ID NO: 2 or at a position corresponding thereto with V, I or W;
(dc) substitution of D at position 369 of the amino acid sequence as shown in SEQ ID NO: 2 or at a position corresponding thereto with N;
(dd) substitution of N at position 376 of the amino acid sequence as shown in SEQ ID NO: 2 or at a position corresponding thereto with W;
(de) substitution of T at position 378 of the amino acid sequence as shown in SEQ ID NO: 2 or at a position corresponding thereto with L or W;
(df) substitution of Q at position 379 of the amino acid sequence as shown in SEQ ID NO: 2 or at a position corresponding thereto with D, E, R or K;
(dg) substitution of Y at position 380 of the amino acid sequence as shown in SEQ ID NO: 2 or at a position corresponding thereto with F;
(dh) substitution of F at position 385 of the amino acid sequence as shown in SEQ ID NO: 2 or at a position corresponding thereto with Y, M or P;
(di) substitution of T at position 386 of the amino acid sequence as shown in SEQ ID NO: 2 or at a position corresponding thereto with A, L, I or M;
(dj) substitution of S at position 387 of the amino acid sequence as shown in SEQ ID NO: 2 or at a position corresponding thereto with G, Q, E, R, K, H, A, V, L, I, M, W or F;
(dk) substitution of N at position 390 of the amino acid sequence as shown in SEQ ID NO: 2 or at a position corresponding thereto with G, S, T, Y or F;
(dl) substitution of W at position 393 of the amino acid sequence as shown in SEQ ID NO: 2 or at a position corresponding thereto with Q;
(dm) substitution of R at position 396 of the amino acid sequence as shown in SEQ ID NO: 2 or at a position corresponding thereto with G;
(dn) substitution of F at position 403 of the amino acid sequence as shown in SEQ ID NO: 2 or at a position corresponding thereto with T or K;
(do) substitution of N at position 405 of the amino acid sequence as shown in SEQ ID NO: 2 or at a position corresponding thereto with D, V, L, I, W, F or P;
(dp) substitution of A at position 406 of the amino acid sequence as shown in SEQ ID NO: 2 or at a position corresponding thereto with V, W or F;
(dq) substitution of P at position 407 of the amino acid sequence as shown in SEQ ID NO: 2 or at a position corresponding thereto with G or C;
(dr) substitution of Q at position 408 of the amino acid sequence as shown in SEQ ID NO: 2 or at a position corresponding thereto with N, Y, I or W;
(ds) substitution of S at position 409 of the amino acid sequence as shown in SEQ ID NO: 2 or at a position corresponding thereto with Y or W;
(dt) substitution of T at position 411 of the amino acid sequence as shown in SEQ ID NO: 2 or at a position corresponding thereto with A, V, L or P;
(du) substitution of T at position 427 of the amino acid sequence as shown in SEQ ID NO: 2 or at a position corresponding thereto with R or V; and
(dv) substitution of V at position 433 of the amino acid sequence as shown in SEQ ID NO: 2 or at a position corresponding thereto with L,
(ii) more preferably, any of the following:
the (ar);
the (bk);
the (bm);
the (cj);
the (cm);
the (dc);
a combination of the (e) and (aa);
a combination of the (bc) and (bd);
a combination of the (bm) and (bn);
a combination of the (bm) and (cm);
a combination of the (bm), (bn) and (cm);
a combination of the (d), (bm) and (cm);
a combination of the (d), (bm), (bn) and (cm);
a combination of the (v), (cf), (da) and (dj);
a combination of the (j), (s), (y), (bh) and (do);
a combination of the (as), (at) and (au);
a combination of the (e), (v), (aa), (bc), (bd), (bk), (cf), (da), (dc) and (dj);
a combination of the (e), (v), (aa), (ar), (bc), (bd), (bk), (cf), (da), (dc) and (dj);
a combination of the (j), (s), (v), (y), (as), (at), (au), (bc), (bd), (bh), (bk), (cf), (da), (dc), (dj) and (do);
a combination of the (v), (aa), (ar), (bc), (bd), (bk), (cf), (da), (dc) and (dj);
a combination of the (v), (as), (at), (au), (bc), (bd), (bk), (cf), (da), (dc) and (dj);
a combination of the (e), (v), (aa), (bc), (bd), (bk), (bo), (cf), (co), (da), (dc) and (dj);
a combination of the (v), (as), (at), (au), (bc), (bd), (bj), (bk), (bq), (cf), (da), (dc), (df) and (dj);
a combination of the (e), (v), (aa), (ar), (bc), (bd), (bk), (cf), (cj), (da), (dc) and (dj);
a combination of the (e), (v), (z), (aa), (ar), (bc), (bd), (bk), (bo), (cf), (cj), (da), (dc) and (dj);
a combination of the (e), (v), (z), (aa), (ar), (bc), (bd), (bk), (bm), (bn), (bo), (cf), (cj), (da), (dc) and (dj);

a combination of the (e), (v), (z), (aa), (ar), (bc), (bd), (bk), (bm), (bo), (cf), (cj), (cm), (da), (dc), and (dj);

a combination of the (e), (v), (z), (aa), (ar), (bc), (bd), (bk), (bm), (bn), (bo), (cf), (cj), (cm), (da), (dc) and (dj);

a combination of the (d), (e), (v), (z), (aa), (ar), (bc), (bd), (bk), (bm), (bo), (cf), (cj), (cm), (da), (dc) and (dj); and a combination of the (d), (e), (v), (z), (aa), (ar), (bc), (bd), (bk), (bm), (bn), (bo), (cf), (cj), (cm), (da), (dc) and (dj), (iii) further more preferably one or more selected from the group consisting of the following $(d_1)$, $(bm_1)$, $(bn_1)$ and $(cm_1)$:

$(d_1)$ substitution of S at a position corresponding to position 15 of SEQ ID NO:2 with D or E;

$(bm_1)$ substitution of H at a position corresponding to position 201 of SEQ ID NO:2 with D or E;

$(bn_1)$ substitution of V at a position corresponding to position 202 of SEQ ID NO:2 with E;

$(cm_1)$ substitution of N at a position corresponding to position 304 of SEQ ID NO:2 with A.

[22] The method according to [18] to [21], comprising carrying out any of the following 1) to 10) with respect to the amino acid sequence as shown SEQ ID NO:2 or an amino acid sequence having an identity of at least 90% therewith:

1) substitution of G at a position corresponding to position 303 of SEQ ID No:2 with E, and
substitution of N at a position corresponding to position 304 of SEQ ID No:2 with A;

2) substitution of G at a position corresponding to position 303 of SEQ ID No:2 with E,
substitution of H at a position corresponding to position 201 of SEQ ID No:2 with D, and
substitution of N at a position corresponding to position 304 of SEQ ID No:2 with A;

3) substitution of G at a position corresponding to position 303 of SEQ ID No:2 with E,
substitution of S at a position corresponding to position 15 of SEQ ID No:2 with D or E,
substitution of H at a position corresponding to position 201 of SEQ ID No:2 with D, and
substitution of N at a position corresponding to position 304 of SEQ ID No:2 with A;

4) substitution of G at a position corresponding to position 303 of SEQ ID No:2 with E,
substitution of H at a position corresponding to position 201 of SEQ ID No:2 with D,
substitution of V at a position corresponding to position 202 of SEQ ID No:2 with E, and
substitution of N at a position corresponding to position 304 of SEQ ID No:2 with A;

5) substitution of G at a position corresponding to position 303 of SEQ ID No:2 with E,
substitution of S at a position corresponding to position 15 of SEQ ID No:2 with D or E,
substitution of H at a position corresponding to position 201 of SEQ ID No:2 with D,
substitution of V at a position corresponding to position 202 of SEQ ID No:2 with E, and
substitution of N at a position corresponding to position 304 of SEQ ID No:2 with A;

6) substitution of G at a position corresponding to position 303 of SEQ ID No:2 with N, and
substitution of N at a position corresponding to position 304 of SEQ ID No:2 with A;

7) substitution of G at a position corresponding to position 303 of SEQ ID No:2 with N,
substitution of H at a position corresponding to position 201 of SEQ ID No:2 with D, and
substitution of N at a position corresponding to position 304 of SEQ ID No:2 with A;

8) substitution of G at a position corresponding to position 303 of SEQ ID No:2 with N,
substitution of S at a position corresponding to position 15 of SEQ ID No:2 with D or E,
substitution of H at a position corresponding to position 201 of SEQ ID No:2 with D, and
substitution of N at a position corresponding to position 304 of SEQ ID No:2 with A;

9) substitution of G at a position corresponding to position 303 of SEQ ID No:2 with N,
substitution of H at a position corresponding to position 201 of SEQ ID No:2 with D,
substitution of V at a position corresponding to position 202 of SEQ ID No:2 with E, and
substitution of N at a position corresponding to position 304 of SEQ ID No:2 with A;

10) substitution of G at a position corresponding to position 303 of SEQ ID No:2 with N,
substitution of S at a position corresponding to position 15 of SEQ ID No:2 with D or E,
substitution of H at a position corresponding to position 201 of SEQ ID No:2 with D,
substitution of V at a position corresponding to position 202 of SEQ ID No:2 with E, and
substitution of N at a position corresponding to position 304 of SEQ ID No:2 with A.

[23] The method according to any one of [18] to [22], wherein
the amino acid sequence having an identity of at least 90% with the amino acid sequence as shown in SEQ ID NO: 2 preferably has aspartic acid at a position corresponding to position 30 of the amino acid sequence as shown in SEQ ID NO: 2, histidine at a position corresponding to position 68 thereof, and serine at a position corresponding to position 255 thereof,
more preferably has the amino acid residues shown in the above described Table 1(ii) at positions corresponding to the positions shown in the above described Table 1(i) in the amino acid sequence as shown in SEQ ID NO: 2.

[24] The method according to any one of [18] to [22], wherein the amino acid sequence as shown in SEQ ID NO: 2 or the amino acid sequence having an identity of at least 90% therewith is preferably the amino acid sequence shown in any of SEQ ID NOS: 2 to 4.

[25] The method according to any one of [18] and [20] to [24], wherein the mutant protease has improved stability under acidic condition in comparison to a parent protease.

[26] The method according to any one of [19] to [25], wherein the acidic condition is preferably weakly acidic condition, more preferably condition of pH 5 or more, further more preferably condition of pH 5 or more and less than pH 7, further more preferably condition of from pH 6 to pH 6.8.

EXAMPLES

Hereinafter, the present invention will be more specifically described in the following examples. However, these examples are not intended to limit the technical scope of the present invention.

Primers used in the following examples are listed in Table 2.

TABLE 2

| Mutation primer R (Reverse) | | | Mutation Primer F (Forward) | | |
|---|---|---|---|---|---|
| Primer | Sequence | SEQ ID NO: | Primer | Sequence | SEQ ID NO: |
| 303_R | GTTCGGGTAGCCAAGGCCGATGTC | 8 | 303A_F | CTTGGCTACCCGAACGCAAACCAAGGATGGGGACG | 9 |
| | | | 303C_F | CTTGGCTACCCGAACTGCAACCAAGGATGGGGACG | 10 |
| | | | 303D_F | CTTGGCTACCCGAACGATAACCAAGGATGGGGACG | 11 |
| | | | 303E_F | CTTGGCTACCCGAACGAAAACCAAGGATGGGGACG | 12 |
| | | | 303F_F | CTTGGCTACCCGAACTTCAACCAAGGATGGGGACG | 13 |
| | | | 303H_F | CTTGGCTACCCGAACCATAACCAAGGATGGGGACG | 14 |
| | | | 303I_F | CTTGGCTACCCGAACATTAACCAAGGATGGGGACG | 15 |
| | | | 303K_F | CTTGGCTACCCGAACAAAAACCGAGGATGGGGACG | 16 |
| | | | 303L_F | CTTGGCTACCCGAACCTTAACCAAGGATGGGGACG | 17 |
| | | | 303M_F | CTTGGCTACCCGAACATGAACCAAGGATGGGGACG | 18 |
| | | | 303N_F | CTTGGCTACCCGAACAATAACCAAGGATGGGGACG | 19 |
| | | | 303P_F | CTTGGCTACCCGAACCCAAACCAAGGATGGGGACG | 20 |
| | | | 303Q_F | CTTGGCTACCCGAACCAGAACCAAGGATGGGGACG | 21 |
| | | | 303R_F | CTTGGCTACCCGAACAGAAACCAAGGATGGGGACG | 22 |
| | | | 303S_F | CTTGGCTACCCGAACTCCAACCAAGGATGGGGACG | 23 |
| | | | 303T_F | CTTGGCTACCCGAACACAAACCAAGGATGGGGACG | 24 |
| | | | 303V_F | CTTGGCTACCCGAACGTGAACCAAGGATGGGGACG | 25 |
| | | | 303W_F | CTTGGCTACCCGAACTGGAACCAAGGATGGGGACG | 26 |
| | | | 303Y_F | CTTGGCTACCCGAACTATAACCAAGGATGGGGACG | 27 |
| | | | 303E/304A_F | CTTGGCTACCCGAACGAAGCACAAGGATGGGGACG | 28 |
| 15_R | CTGAGCCACATCCGCTTTGACAAT | 29 | 15D_F | GCGGATGTGGCTCAGGATGTGTACGGGTTGTATGG | 30 |
| | | | 15E_F | GCGGATGTGGCTCAGGAAGTGTACGGGTTGTATGG | 31 |
| 201_R | GTTGATATTGTCCGCGCAAGACCC | 32 | 201D_F | GCGGACAATATCAACGATGTGGCATGCTTCTCTTC | 33 |
| 201D/202_R | ATCGTTGATATTGTCCGCGCAAGA | 34 | 201D/202E_F | GACAATATCAACGATGAAGCATGCTTCTCTTCACG | 35 |
| 303N/304_R | CTGGTTCGGGTAGCCAAGGCCGAT | 36 | 303N/304A_F | GGCTACCCGAACCAGGCACAAGGATGGGGACGAGT | 37 |
| 195_R | AGACCCAAAGCTTGGGCGGAGGTT | 38 | 201D/195Q_F | CCAAGCTTTGGGTCTCAGGCGGACAATATCAACGA | 39 |
| | | | 201D/195M_F | CCAAGCTTTGGGTCTATGGCGGACAATATCAACGA | 40 |
| 201D/204_R | TGCCACATCGTTGATATTGTCCGC | 41 | 201D/204Q_F | ATCAACGATGTGGCACAGTTCTCTTCACGTGGGCC | 42 |

Reference Example 1 Construction of Plasmid pHA64TSA

Plasmid pHA64 (Japanese Patent No. 349293, having a BamHI site and an XbaI site downstream of the expression vector) was simultaneously digested with restriction enzymes BamHI and XbaI (Roche) to obtain a gene insertion/expression vector. Meanwhile, DNA containing wild type KP43 protease gene (SEQ ID No: 1) (having a BamHI site in 5'-upstream of the gene, and an XbaI site 3'-downstream of the gene) was simultaneously digested with BamHI and XbaI, mixed with the gene insertion/expression vector previously obtained and subjected to a ligation reaction using Ligation High (manufactured by Toyobo Co., Ltd.). The ligation product was purified through ethanol precipitation, a host bacterium, Bacillus sp. KSM-9865 strain (FERM P-18566) was transformed with this in accordance with an electroporation method. The treated cells were smeared onto a skim milk-containing alkali LB agar medium [1% (w/v) skim milk (Difco), 1% Bacto tryptone (Difco), 0.5% yeast extract (Difco), 1% sodium chloride, 1.5% agar, 0.05% sodium carbonate and 15 ppm tetracycline]. Several days later, from colonies formed in the agar medium, a transformant having a protease gene introduced therein was screened based on the presence or absence of skim milk dissolution plaques. Plasmid DNA was extracted from the transformant and whether the desired protease gene (SEQ ID No: 1) was correctly inserted were checked to thereby obtain a desired plasmid pHA6TSA.

Reference Example 2 Preparation of Protease

A method for preparing a protease used for enzyme stability evaluation will be described below using wild type KP43 protease as an example. Specifically, the transformant of the KSM-9865 strain retaining pHA64TSA was inoculated in 5 mL of a seed stock medium [6.0% (w/v) polypeptone S, 0.05% yeast extract, 1.0% maltose, 0.02% magnesium sulfate-heptahydrate, 0.1% potassium dihydrogen phosphate, 0.25% sodium carbonate, 30 ppm tetracycline) and cultured while shaking at 30° C. for 16 hours. Subsequently, to 20 mL of a main medium [8% polypeptone S, 0.3% yeast extract, 10% maltose, 0.04% magnesium sulfate-heptahydrates, 0.2% potassium dihydrogen phosphate, 1.5% anhydrous sodium carbonate, 30 ppm tetracycline], the seed stock culture solution (1% (v/v)) was inoculated and cultured while shaking at 30° C. for 3 days. The culture solution obtained was centrifuged to acquire a culture supernatant containing a protease. The protein mass of the culture supernatant was measured using a Protein Assay Rapid kit Wako (Wako Pure Chemical Industries Ltd.).

Reference Example 3 Measurement of Protease Activity 40 mM of a Glt-Ala-Ala-Pro-Leu-pNA dissolved in dimethyl sulfoxide (AAPL; Peptide Institute, Inc.), 266 mM phosphate buffer (pH 7.4, Wako 167-14491), and ion exchange water were each mixed at a ratio of 3 volumes, 10 volumes, and 7 volumes to prepare a substrate solution. To each well of a 96-well plate, 50 µL of the substrate solution was dispensed, and a protease-containing solution diluted with ion exchange water was added thereto, to thereby start a reaction. Immediately after the start of the reaction, the assay plate was inserted into a chamber of a microplate reader VersaMax (Molecular Device) with a temperature set to 30° C. in advance, a change in absorbance at 420 nm was measured in kinetic mode for 10 minutes. A value of the absorbance-changing rate (mOD/min) output as a measurement result is considered as protease activity.

Reference Example 4 Evaluation of Protease Stability Under Weakly Acidic Condition in Presence of Surfactant To each of 60 wells of a 96-deep well plate excluding outer wells, 450 µL of a 10% LAS solution (200 g of NEOPELEX G-25 (Kao, active ingredient 25%), diluted with ion exchange water for use) and 50 µL of a 200 mM Britton-Robinson buffer (pH 8.5, 6.5 or 6.0) were added, and stirred with a mixer (Yamato Scientific Co., Ltd., CM-1000) at 2,500 rpm, to thereby prepare surfactant-containing compositions with each pH. To the composition, a protease solution adjusted to a protein mass of 10 mg/mL was added, and the resultant solution was stirred with the mixer at 2,500 rpm for one minute, to thereby obtain an enzyme solution. Immediately after the stirring, 20 µL of the enzyme solution was separated and added to each well of a 96-well plate containing 250 µL of ion exchange water in advance, and the resultant solution was sufficiently stirred, to thereby obtain a 13.5-fold diluted solution. To each well of a 96-well plate containing 50 µL of the substrate solution in advance, 50 µL of the diluted solution was added to prepare a reaction solution. The plate containing the reaction solution was inserted into a microplate reader VersaMAX to measure a change in absorbance, to thereby obtain protease initial activity. When measuring protease activity, it was confirmed that the reaction solution has pH 7.4 due to buffer capacity of the substrate solution. Further, about two minutes was required to start the measurement of activity after mixing a surfactant-containing composition and a protease solution.

The outer wells of the deep well plate containing the remained enzyme solution were added with 1 mL of water and sealed tightly with a PCR seal to keep warm at 40° C. After the predetermined time, 20 µL of the enzyme solution was separated again from the deep-well plate, and the value of protease activity was obtained according to the same procedures as those in the measurement of initial activity.

For each protease mutant, an activity value at initial stage (two minutes after mixing) and an activity value after a predetermined time under weakly acidic condition (pH 6.5 or 6.0) are divided by an activity value at initial stage under condition of pH 8.5 and multiplied by 100, and the obtained value is considered as a residual activity at initial stage and a residual activity after the predetermined time (%). The obtained residual activity at initial stage and residual activity after the predetermined time (%) are divided by the residual activity for the parent protease of the mutant at the same time point, and multiplied by 100. The obtained value is considered as relative residual activity (%%) at initial stage and after the predetermined time of the protease mutant with respect to its parent protease for protease activity under weakly acidic condition in the presence of surfactant.

Example 1 Production of Protease Mutant

The method for producing the protease mutant according to the present invention will be described below, using, as an example, the production of a mutant, in which the glycine at position 303 (G303) in the amino acid sequence (SEQ ID NO: 2) of a wild-type KP43 protease mature enzyme region has been substituted with aspartic acid, (G303D mutant).

Mutation primers 303D_F and 303_R (SEQ ID Nos: 11 and 8, Table 2) were designed, and synthesis of these was asked to Eurofirns Genomics. Using plasmid pHA64TSA containing protease gene (SEQ ID NO:1) obtained in Reference Example 1 as a template and these synthesized mutation primers, PCR was carried out in accordance with the protocols of PrimeSTAR Mutagenesis Basal Kit (Takara), and a PCR product of protease gene containing a mutation was obtained. The PCR product was purified with a PCR product purification kit (Roche), and a *Bacillus* sp. KSM9865 strain (FERM P-18566) used as a host bacterium was then transformed therewith by electroporation method. Transformant was screened and cultured according to the same procedures as those in Reference Example 1, to thereby obtain G303D mutant of wild type KP43 protease.

Example 2 Production of Protease Mutants (1) Production of Parent Protease

With reference to the descriptions of JP-A-2011-200249, JP-A-2002-218989, JP-A-2002-306176, JP-A-2004-000122, JP-A-2004-305176, JP-A-2010-273672, JP-A-2010-273673, and JP-A-2017-221188, a mutation was introduced into a wild-type KP43 protease (SEQ ID NO: 2) to produce a duodecuple mutant of KP43 protease (SEQ ID NO:3). This mutant had 97.2% identity of amino acid sequence with wild type KP43 protease (SEQ ID NO:2).

Duodecuple Mutant (SEQ ID NO: 3):

Alanine at position 132 was substituted with threonine (JP-A-2011-200249); tyrosine at position 195 was substituted with glutamine (JP-A-2002-218989);

aspartic acid at position 369 was substituted with asparagine (JP-A-2002-306176);

threonine at position 65 was substituted with proline, valine at position 273 was substituted with isoleucine, threonine at position 359 was substituted with serine, and serine at position 387 was substituted with alanine (JP-A-2004-000122);

serine at position 16 was substituted with valine, asparagine at position 166 was substituted with glycine, and glycine at position 167 was substituted with valine (JP-A-2004-305176, JP-A-2010-273673);

asparagine at position 83 was substituted with alanine (JP-A-2010-273672, JP-A-2010-273673); and alanine at position 294 was substituted with threonine (JP-A-2017-221188).

(2) Preparation of Protease Mutant

Using the duodecuple mutant obtained in the above (1) as a parent protease, a protease mutant of interest was produced. Into a polynucleotide encoding the duodecuple mutant, such a mutation was introduced that the amino acid residue at position 303 was substituted with another amino acid residue using mutations primers shown in Table 3 according to the same procedures as those of Example 1. Thereafter, a host was transformed with the obtained mutant polynucleotide. The obtained transformant was then cultured to obtain a culture supernatant containing a protease mutant of interest according to the same procedures as those of Reference Example 2. The protein mass thereof was then measured.

TABLE 3

Position 303 mutants and mutation primers

| | Mutation primer R | | Mutation primer F | |
|---|---|---|---|---|
| Mutant name | Primer name | SEQ ID NO: | Primer name | SEQ ID NO: |
| G303A | 303_R | 8 | 303A_F | 9 |
| G303C | | | 303C_F | 10 |
| G303D | | | 303D_F | 11 |
| G303E | | | 303E_F | 12 |
| G303F | | | 303F_F | 13 |
| G303H | | | 303H_F | 14 |
| G303I | | | 303I_F | 15 |
| G303K | | | 303K_F | 16 |
| G303L | | | 303L_F | 17 |
| G303M | | | 303M_F | 18 |
| G303N | | | 303N_F | 19 |
| G303P | | | 303P_F | 20 |
| G303Q | | | 303Q_F | 21 |
| G303R | | | 303R_F | 22 |
| G303S | | | 303S_F | 23 |
| G303T | | | 303T_F | 24 |
| G303V | | | 303V_F | 25 |
| G303W | | | 303W_F | 26 |
| G303Y | | | 303Y_F | 27 |

(3) Preparation of Double Mutant

Into the polynucleotide encoding the duodecuple mutant obtained in the above (1), such mutations were introduced that the amino acid residue at position 303 was substituted with glutamic acid and the amino acid residue at position 304 was substituted with alanine, using the mutation primers shown in Table 4 according to the same procedures as those of Example 1, to thereby obtain a mutant polynucleotide. Similarly, a mutant polynucleotide introduced therein only the substitution at position 304 was obtained. A host was transformed with the obtained mutant polynucleotide. The transformant was cultured to obtain a culture supernatant containing the protease mutant of interest according to the procedures of Reference Example 2. The protein mass thereof was measured.

TABLE 4

Position 303/304 mutant and mutation primer

| | Mutation primer R | | Mutation primer F | |
|---|---|---|---|---|
| Mutant | Primer Name | SEQ ID NO: | Primer Name | SEQ ID NO: |
| G303E/N304A | 303_R | 8 | 303E/304A_F | 28 |

Example 3 Evaluation of Stability of Protease Mutant

The mutant proteases prepared in Examples 1 and 2 were examined in terms of stability. According to the procedures of Reference Example 4, relative residual activity (%%) of each mutant was measured at initial stage (after 2 minutes), and after 1-hour, 2-hour, and 3-hour preservation in a surfactant-containing composition with pH 6.5. The results are shown in Table 5. It was indicated that the mutants having aspartic acid, glutamic acid, isoleucine, methionine, asparagine or valine at a position corresponding to position 303 (G303D, G303E, G303I, G303M, G303N and G303V) had very high relative residual activity (%%) in comparison to the parent protease, and had very high stability under weakly acidic condition. It was indicated that the mutants having phenylalanine, glutamine, tryptophan or tyrosine at a position corresponding to position 303 (G303F, G303Q, G303W and G303Y) had high relative residual activity (%%) in comparison to the parent protease, and had high stability under weakly acidic condition. It was indicated that the mutants having proline or threonine at a position corresponding to position 303 (G303P and G303T) had relatively high relative residual activity (%%) in comparison to the parent protease, and had relatively high stability under weakly acidic condition. The double mutant having mutations at positions 303 and 304 had significantly improved stability in comparison to the single mutant. Further, when the wild type enzyme (KP43 protease) was examined in terms of stability, the enzyme was deactivated immediately after mixing with a surfactant-containing composition with pH 6.5. These results indicate that the protease duodecuple mutant had significantly improved relative residual activity in comparison to the wild type, and therefore the protease mutant obtained in Example 2 had extremely high stability under weakly acidic condition in comparison to the wild type.

TABLE 5

Relative residual activity of position 303 mutants (%%)

| | Condition | | | | |
|---|---|---|---|---|---|
| Mutant | pH 8.5 Initial | pH 6.5 Initial | pH 6.5 1-hour | pH 6.5 2-hour | pH 6.5 3-hour |
| G303A | 100 | 92 | 96 | 97 | 100 |
| G303C | 100 | 69 | 52 | 48 | 47 |
| G303D | 100 | 216 | 259 | 255 | 248 |
| G303E | 100 | 238 | 277 | 264 | 254 |
| G303F | 100 | 109 | 132 | 137 | 142 |
| G303H | 100 | 94 | 101 | 103 | 107 |
| G303I | 100 | 166 | 223 | 231 | 238 |
| G303K | 100 | 67 | 74 | 76 | 75 |
| G303L | 100 | 102 | 94 | 92 | 93 |
| G303M | 100 | 129 | 155 | 160 | 167 |
| G303N | 100 | 121 | 148 | 154 | 157 |
| G303P | 100 | 105 | 114 | 115 | 116 |
| G303Q | 100 | 116 | 129 | 129 | 133 |
| G303R | 100 | 32 | 32 | 34 | 34 |
| G303S | 100 | 92 | 93 | 92 | 96 |
| G303T | 100 | 103 | 110 | 111 | 113 |
| G303V | 100 | 147 | 184 | 192 | 192 |
| G303W | 100 | 101 | 127 | 134 | 140 |
| G303Y | 100 | 110 | 130 | 135 | 139 |
| G303E/N304A | 100 | 332 | 504 | 595 | 616 |
| Parent (duodecuple Mutant) | 100 | 100 | 100 | 100 | 100 |

Example 4 Preparation of Protease Multiple Mutant and Stability Evaluation-1

(1) Preparation of Parent Protease

With reference to the descriptions of JP-A-2011-200249, JP-A-2002-218989, JP-A-2002-306176, JP-A-2004-000122, JP-A-2004-305176, JP-A-2010-273672, JP-A-2010-273673, and JP-A-2017-221188, the following mutation was introduced into a wild-type KP43 protease (SEQ ID NO: 2) to produce a KP43 protease quattuordecuple mutant (SEQ ID NO:4). This mutant had 96.8% identity of the amino acid sequence with the wild type KP43 protease (SEQ ID NO: 2). Quattuordecuple mutant (SEQ ID NO:4):

Alanine at position 132 was substituted with threonine (JP-A-2011-200249);

tyrosine at position 195 was substituted with cysteine (JP-A-2002-218989);

aspartic acid at position 369 was substituted with asparagine (JP-A-2002-306176);

threonine at position 65 was substituted with proline, valine at position 273 was substituted with isoleucine, threonine at position 359 was substituted with serine, and serine at position 387 was substituted with alanine (JP-A-2004-000122);

serine at position 16 was substituted with valine, asparagine at position 166 was substituted with glycine, and glycine at position 167 was substituted with valine (JP-A-2004-305176, JP-A-2010-273673);

threonine at position 82 was substituted with glutamic acid, asparagine at position 83 was substituted with alanine, and glutamine at position 204 was substituted with cysteine (JP-A-2010-273672 and JP-A-2010-273673); and alanine at position 294 was substituted with threonine (JP-A-2017-221188).

(2) Preparation of Protease Multiple Mutant

Using the quattuordecuple mutant obtained the above (1) as a parent protease, protease multiple mutants shown in Table 6(A) were prepared. For a polynucleotide encoding the quattuordecuple mutant, the multiple mutants shown in Table 6(A) and culture supernatants containing the mutants were prepared using mutation primers shown in Table 6(B) by repeating the procedures of Example 1.

TABLE 6

(A) Mutant and mutation primer set

| Mutant | Primer set |
|---|---|
| 201D/303E/304A | CE |
| 15D/201D/303E/304A | ACE |
| 15E/201D/303E/304A | BCE |
| 201D/303N/304A | CF |
| 15D/201D/303N/304A | ACF |
| 15E/201D/303N/304A | BCF |
| 201D/202E/303E/304A | CDE |
| 15D/201D/202E/303E/304A | ACDE |
| 15E/201D/202E/303E/304A | BCDE |

TABLE 6-continued

| 201D/202E/303N/304A | CDF |
| 15D/201D/202E/303N/304A | ACDF |
| 15E/201D/202E/303N/304A | BCDF |

(B) Mutation primer

| Primer set | Mutation primer R | | Mutation primer F | | Introduced mutation |
|---|---|---|---|---|---|
| | Primer name | SEQ ID NO: | Primer name | SEQ ID NO: | |
| A | 15_R | 29 | 15D_F | 30 | S15D |
| B | 15_R | 29 | 15E_F | 31 | S15E |
| C | 201_R | 32 | 201D_F | 33 | H201D |
| D | 201D/202_R | 34 | 201D/202E_F | 35 | H201D/V202E |
| E | 303_R | 8 | 303E/304A_F | 28 | G303E/N304A |
| F | 303N/304_R | 36 | 303N/304A_F | 37 | G303N/N304A |

(3) Evaluation of Stability of Protease

According to the procedures of Reference Example 4, relative residual activity (%%) of each protease multiple mutant prepared in the above (2) was measured at initial stage (after 2 minutes), and after 1-day, 2-day, 4-day and 8-day preservation in a surfactant-containing composition with pH 6.5. The results are shown in Table 7. It is indicated that the mutants having the mutation at position 15, 201, 202 or 304 in addition to the mutation at position 303 had high relative residual activity (%%) at pH 6.0. Further, the quattuordecuple mutant used as a parent protease in this Example had improved relative residual activity in a surfactant-containing composition with pH 6.0 in comparison to the duodecuple mutant used as a parent protease in Example 2.

According to the same procedures, relative residual activity (%%) of each mutant was measured at initial stage (after 2 minutes), and after 1-day in a surfactant-containing composition with pH 5.0. The results are shown in Table 7. Almost all mutant examined had high relative residual activity (%%) even at pH 5.0.

TABLE 7

Relative residual activity of multiple mutant (%%)

| | Condition | | | | | | Condition | | |
|---|---|---|---|---|---|---|---|---|---|
| Mutant | pH 8.5 2 min | pH 6.0 2 min | pH 6.0 1 day | pH 6.0 2 day | pH 6.0 4 day | pH 6.0 8 day | pH 8.5 2 min | pH 5.0 2 min | pH 5.0 1 day |
| 201D/303E/304A | 100 | 134 | 468 | 665 | 1176 | 2082 | 100 | 209 | 845 |
| 15D/201D/303E/304A | 100 | 132 | 500 | 769 | 1550 | 3310 | 100 | 218 | 8118 |
| 15E/201D/303E/304A | 100 | 132 | 503 | 782 | 1568 | 3374 | 100 | 221 | 7678 |
| 201D/303N/304A | 100 | 129 | 414 | 587 | 1007 | 1638 | 100 | 196 | 424 |
| 15D/201D/303N/304A | 100 | 132 | 482 | 732 | 1424 | 2931 | 100 | 213 | 6072 |
| 15E/201D/303N/304A | 100 | 133 | 498 | 755 | 1510 | 3138 | 100 | 220 | 5817 |
| 201D/202E/303E/304A | 100 | 133 | 377 | 558 | 1116 | 2403 | 100 | 222 | 6563 |
| 15D/201D/202E/303E/304A | 100 | 132 | 422 | 640 | 1323 | 3005 | 100 | 237 | 19610 |
| 15E/201D/202E/303E/304A | 100 | 135 | 432 | 660 | 1378 | 3139 | 100 | 232 | 19113 |
| 201D/202E/303N/304A | 100 | 132 | 401 | 614 | 1229 | 2555 | 100 | 243 | 5591 |
| 15D/201D/202E/303N/304A | 100 | 133 | 422 | 637 | 1278 | 2750 | 100 | 236 | 17236 |
| 15E/201D/202E/303N/304A | 100 | 135 | 437 | 650 | 1302 | 2818 | 100 | 229 | 16462 |
| Parent (quattuordecuple mutant) | 100 | 100 | 100 | 100 | 100 | 100 | 100 | 100 | 100 |

Example 5 Preparation of Protease Multiple Mutant and Evaluation of Stability-2

(1) Preparation of Protease Multiple Mutant

Using, as a parent protease, multiple mutants 201D/303E/304A (SEQ ID NO:5), 15D/201D/303E/304A (SEQ ID NO:6) and 15E/201D/303E/304A (SEQ ID NO:7) obtained in Example 4, protease multiple mutants shown in Table 8(A) were prepared. For a polynucleotide encoding the parent proteases of SEQ ID Nos:5 to 7, the multiple mutants shown in Table 8(A) and culture supernatants containing the mutants were prepared using mutation primers shown in Table 8(B) by repeating the procedures of Example 1.

TABLE 8

(A) Mutant and Mutation primer set

| Mutant | Parent | Primer set |
|---|---|---|
| 201D/303E/304A/195Q/204Q | 201D/303E/304A | GI |
| 15D/201D/303E/304A/195Q/204Q | 15D/201D/303E/304A | GI |
| 15E/201D/303E/304A/195Q/204Q | 15E/201D/303E/304A | GI |
| 201D/303E/304A/195M/204Q | 201D/303E/304A | HI |
| 15D/201D/303E/304A/195M/204Q | 15D/201D/303E/304A | HI |
| 15E/201D/303E/304A/195M/204Q | 15E/201D/303E/304A | HI |
| 201D/303E/304A/195Q/204Q | 201D/303E/304A | GI |
| 15D/201D/303E/304A/195Q/204Q | 15D/201D/303E/304A | GI |
| 15E/201D/303E/304A/195Q/204Q | 15E/201D/303E/304A | GI |
| 201D/303E/304A/195M/204Q | 201D/303E/304A | HI |
| 15D/201D/303E/304A/195M/204Q | 15D/201D/303E/304A | HI |
| 15E/201D/303E/304A/195M/204Q | 15E/201D/303E/304A | HI |
| 201D/303E/304A/195Q/204Q | 201D/303E/304A | GI |

(B) Mutation primer

| Primer set | Mutation primer R Primer name | SEQ ID NO: | Mutation primer F Primer name | SEQ ID NO: | Introduced mutation |
|---|---|---|---|---|---|
| G | 195_R | 38 | 201D/195Q_F | 39 | H201D/C195Q |
| H | 195_R | 38 | 201D/195M_F | 40 | H201D/C195M |
| I | 201D/204_R | 441 | 201D/204Q_F | 42 | H201D/C204Q |

(2) Evaluation of Stability of Protease

According to the procedures of Reference Example 4, relative residual activity (%%) of each protease multiple mutant prepared in the above (1) with respect to the quattuordecuple mutant prepared in Example 4 was measured. Specifically, relative residual activity of each multiple mutant with respect to the quattuordecuple mutant was measured at initial stage (after 2 minutes), and after 1-day, 2-day and 4-day preservation in a surfactant-containing composition with pH 6.0. The results are shown in Table 9. Each multiple mutant had high relative residual activity at pH 6.0. Specifically, the mutant having cysteine at position 204 and cysteine at position 195 substituted in the protease of SEQ ID Nos: 5 to 7 apparently had high relative residual activity at either time with respect to the quattuordecuple mutant.

TABLE 9

Relative residual activity of multiple mutant (%%)

| | Condition | | | | |
|---|---|---|---|---|---|
| Mutant | pH 8.5 2 min | pH 6.0 2 min | pH 6.0 1 day | pH 6.0 2 day | pH 6.0 4 day |
| 201D/303E/304A (SEQ ID NO: 5) | 100 | 134 | 468 | 665 | 1176 |
| 2010/303E/304A/195Q/204Q | 100 | 128 | 246 | 215 | 138 |

TABLE 9-continued

| | Relative residual activity of multiple mutant (%%) | | | | |
|---|---|---|---|---|---|
| | Condition | | | | |
| Mutant | pH 8.5 2 min | pH 6.0 2 min | pH 6.0 1 day | pH 6.0 2 day | pH 6.0 4 day |
| 201D/303E/304A/195M/204Q | 100 | 130 | 301 | 287 | 210 |
| Parent (quattuordecuple mutant) | 100 | 100 | 100 | 100 | 100 |
| 15D/201D/303E/304A (SEQ ID NO: 6) | 100 | 132 | 500 | 769 | 1550 |
| 15D/201D/303E/304A/195Q/204Q | 100 | 128 | 377 | 459 | 525 |
| 15D/201D/303E/304A/195M/204Q | 100 | 129 | 410 | 520 | 630 |
| Parent (quattuordecuple mutant) | 100 | 100 | 100 | 100 | 100 |
| 15E/201D/303E/304A (SEQ ID NO: 7) | 100 | 132 | 503 | 782 | 1568 |
| 15E/201D/303E/304A/195Q/204Q | 100 | 131 | 436 | 548 | 663 |
| 15E/201D/303E/304A/195M/204Q | 100 | 129 | 432 | 555 | 733 |
| Parent (quattuordecuple mutant) | 100 | 100 | 100 | 100 | 100 |

While the embodiments of the present invention have been described above, it should be understood that these are not intended to limit the present invention to the specific embodiments described. Various other changes and modifications that fall within the scope of the present invention are apparent to those skilled in the art.

The literatures and patent applications cited in the present description are incorporated by reference as if they were fully described in the present description.

What is claimed is:

1. A mutant protease that consists of an amino acid sequence having an identity of at least 90% with the amino acid sequence as shown in SEQ ID NO: 2 and that has an amino acid residue selected from the group of consisting of aspartic acid, glutamic acid, phenylalanine, histidine, isoleucine, methionine, proline, glutamine, threonine, valine, tryptophan, and tyrosine at a position corresponding to position 303 of the amino acid sequence as shown in SEQ ID NO:2.

2. The mutant protease according to claim 1, which has one or more amino acid residues selected from the group consisting of the following (a') to (dv'):
   (a') S, T, C, Q, Y, R, K, H, A, V, L, I, M, W or F at position 6 of the amino acid sequence as shown in SEQ ID NO: 2 or at a position corresponding thereto;
   (b') Q at position 9 of the amino acid sequence as shown in SEQ ID NO: 2 or at a position corresponding thereto;
   (c') G, S or N at position 11 of the amino acid sequence as shown in SEQ ID NO: 2 or at a position corresponding thereto;
   (d') H, C, Q, D, E, R, A, V, M, W or F at position 15 of the amino acid sequence as shown in SEQ ID NO: 2 or at a position corresponding thereto;
   (e') T, Q, V, C, Y, D, E, R, K, H, L, I, M, W or F at position 16 of the amino acid sequence as shown in SEQ ID NO: 2 or at a position corresponding thereto;
   (f') F or A at position 20 of the amino acid sequence as shown in SEQ ID NO: 2 or at a position corresponding thereto;
   (g') W at position 22 of the amino acid sequence as shown in SEQ ID NO: 2 or at a position corresponding thereto;
   (h') N at position 23 of the amino acid sequence as shown in SEQ ID NO: 2 or at a position corresponding thereto;
   (i') T at position 37 of the amino acid sequence as shown in SEQ ID NO: 2 or at a position corresponding thereto;
   (j') V, L, I, W or F at position 40 of the amino acid sequence as shown in SEQ ID NO: 2 or at a position corresponding thereto;
   (k') I at position 41 of the amino acid sequence as shown in SEQ ID NO: 2 or at a position corresponding thereto;
   (l') S, T, C, N, Q, Y, E, K, H, A, V, L, I, M or W at position 46 of the amino acid sequence as shown in SEQ ID NO: 2 or at a position corresponding thereto;
   (m') Q at position 49 of the amino acid sequence as shown in SEQ ID NO: 2 or at a position corresponding thereto;
   (n') G or S at position 52 of the amino acid sequence as shown in SEQ ID NO: 2 or at a position corresponding thereto;
   (o') A, V or I at position 53 of the amino acid sequence as shown in SEQ ID NO: 2 or at a position corresponding thereto;
   (p') G, S, T, C, N, Q, D, E, R, H, A, V, M, W, F or P at position 54 of the amino acid sequence as shown in SEQ ID NO: 2 or at a position corresponding thereto;
   (q') V at position 56 of the amino acid sequence as shown in SEQ ID NO: 2 or at a position corresponding thereto;
   (r') S, T, C, Q, D, E, R, K, H, A, V, L, I, M, W, F or P at position 57 of the amino acid sequence as shown in SEQ ID NO: 2 or at a position corresponding thereto;

(s') V, L, I, M, W or F at position 59 of the amino acid sequence as shown in SEQ ID NO: 2 or at a position corresponding thereto;

(t') V, L, I, W or F at position 60 of the amino acid sequence as shown in SEQ ID NO: 2 or at a position corresponding thereto;

(u') S, D or L at position 63 of the amino acid sequence as shown in SEQ ID NO: 2 or at a position corresponding thereto;

(v') W or P at position 65 of the amino acid sequence as shown in SEQ ID NO: 2 or at a position corresponding thereto;

(w') G, S, T, C, Q, D, E, H, A, V, L, I, M or W at position 66 of the amino acid sequence as shown in SEQ ID NO: 2 or at a position corresponding thereto;

(x') H or A at position 80 of the amino acid sequence as shown in SEQ ID NO: 2 or at a position corresponding thereto;

(y') Q, Y, L, I, W or F at position 81 of the amino acid sequence as shown in SEQ ID NO: 2 or at a position corresponding thereto;

(z') G, S, C, Q, D, E, R, K, H, A or M at position 82 of the amino acid sequence as shown in SEQ ID NO: 2 or at a position corresponding thereto;

(aa') S, C or A at position 83 of the amino acid sequence as shown in SEQ ID NO: 2 or at a position corresponding thereto;

(ab') R at position 84 of the amino acid sequence as shown in SEQ ID NO: 2 or at a position corresponding thereto;

(ac') H at position 89 of the amino acid sequence as shown in SEQ ID NO: 2 or at a position corresponding thereto;

(ad') C at position 91 of the amino acid sequence as shown in SEQ ID NO: 2 or at a position corresponding thereto;

(ae') L, I, W or F at position 100 of the amino acid sequence as shown in SEQ ID NO: 2 or at a position corresponding thereto;

(af') S, T, C, N, Q, Y, D, E, R, K, H, A, V, L, I, M, W, F or P at position 101 of the amino acid sequence as shown in SEQ ID NO: 2 or at a position corresponding thereto;

(ag') S, T, C, Q, Y, D, E, R, K, H, A, V, L, I, M, W, F or P at position 102 of the amino acid sequence as shown in SEQ ID NO: 2 or at a position corresponding thereto;

(ah') S, T, C, Q, Y, D, E, R, K, H, A, V, L, I, M, W, F or P at position 103 of the amino acid sequence as shown in SEQ ID NO: 2 or at a position corresponding thereto;

(ai') S, T, C, Q, Y, D, E, R, K, H, A, V, L, I, M, W, F or P at position 104 of the amino acid sequence as shown in SEQ ID NO: 2 or at a position corresponding thereto;

(aj') S, T, C, Q, Y, D, E, R, K, H, A, V, L, I, M, W, F or P at position 105 of the amino acid sequence as shown in SEQ ID NO: 2 or at a position corresponding thereto;

(ak') S, T, C, Q, Y, D, E, R, K, H, A, V, L, I, M, W, F or P at position 106 of the amino acid sequence as shown in SEQ ID NO: 2 or at a position corresponding thereto;

(al') S, R, K or A at position 107 of the amino acid sequence as shown in SEQ ID NO: 2 or at a position corresponding thereto;

(am') L, I or F at position 109 of the amino acid sequence as shown in SEQ ID NO: 2 or at a position corresponding thereto;

(an') L or W at position 113 of the amino acid sequence as shown in SEQ ID NO: 2 or at a position corresponding thereto;

(ao') G, S, T, C, N, Q, D, E, R, K, H, A, V, M, W, F or P at position 119 of the amino acid sequence as shown in SEQ ID NO: 2 or at a position corresponding thereto;

(ap') Y, R, I, W or F at position 120 of the amino acid sequence as shown in SEQ ID NO: 2 or at a position corresponding thereto;

(aq') K or A at position 124 of the amino acid sequence as shown in SEQ ID NO: 2 or at a position corresponding thereto;

(ar') S, T, N, Q, D, I or M at position 132 of the amino acid sequence as shown in SEQ ID NO: 2 or at a position corresponding thereto;

(as') G, S, T, C, N, Q, D, E, R, K, H, V, L, I, M, W, F or P at position 133 of the amino acid sequence as shown in SEQ ID NO: 2 or at a position corresponding thereto;

(at') G, S, T or A at position 134 of the amino acid sequence as shown in SEQ ID NO: 2 or at a position corresponding thereto;

(au') G, S, T, N, Q, Y, R, K, H, A, L, I, M or W between position 133 of the amino acid sequence as shown in SEQ ID NO: 2 or a position corresponding thereto, and position 134 thereof or a position corresponding thereto;

(av')R, A, L or M at position 135 of the amino acid sequence as shown in SEQ ID NO: 2 or at a position corresponding thereto;

(aw') S, T, C, Q, Y, D, E, R, K, H, A, V, L, I, M, W, F or P at position 136 of the amino acid sequence as shown in SEQ ID NO: 2 or at a position corresponding thereto;

(ax') G, S, C, N, Q, D, E, R, K, H, A, V, M, W, F or P at position 138 of the amino acid sequence as shown in SEQ ID NO: 2 or at a position corresponding thereto;

(ay') L, W or F at position 140 of the amino acid sequence as shown in SEQ ID NO: 2 or at a position corresponding thereto;

(az') G, S, T, C, N, Q, D, E, R, K, H, A, M, W, F or P at position 148 of the amino acid sequence as shown in SEQ ID NO: 2 or at a position corresponding thereto;

(ba') F at position 151 of the amino acid sequence as shown in SEQ ID NO: 2 or at a position corresponding thereto;

(bb') S, T, N, Q, D, K, H, V, L, I or F at position 163 of the amino acid sequence as shown in SEQ ID NO: 2 or at a position corresponding thereto;

(bc') G, V, L, I, W or F at position 166 of the amino acid sequence as shown in SEQ ID NO: 2 or at a position corresponding thereto;

(bd') V at position 167 of the amino acid sequence as shown in SEQ ID NO: 2 or at a position corresponding thereto;

(be') V or L at position 170 of the amino acid sequence as shown in SEQ ID NO: 2 or at a position corresponding thereto;

(bf') G, T, E or A at position 171 of the amino acid sequence as shown in SEQ ID NO: 2 or at a position corresponding thereto;

(bg') S at position 187 of the amino acid sequence as shown in SEQ ID NO: 2 or at a position corresponding thereto;

(bh') V, L, I, W or F at position 191 of the amino acid sequence as shown in SEQ ID NO: 2 or at a position corresponding thereto;

(bi') S, T, C, Q, Y, D, E, R, K, H, A, V, L, I, M, W, F or P at position 193 of the amino acid sequence as shown in SEQ ID NO: 2 or at a position corresponding thereto;

(bj') Y, R or K at position 194 of the amino acid sequence as shown in SEQ ID NO: 2 or at a position corresponding thereto;

(bk') G, S, T, C, N, Q, D, E, R, K, H, A, V, L, I, M, W, F or P at position 195 of the amino acid sequence as shown in SEQ ID NO: 2 or at a position corresponding thereto;
(bl') W at position 200 of the amino acid sequence as shown in SEQ ID NO: 2 or at a position corresponding thereto;
(bm') D, E or Q at position 201 of the amino acid sequence as shown in SEQ ID NO: 2 or at a position corresponding thereto;
(bn') E at position 202 of the amino acid sequence as shown in SEQ ID NO: 2 or at a position corresponding thereto;
(bo') S, T, C, N, D, E, R, K, H, V, L, I, M, W or P at position 204 of the amino acid sequence as shown in SEQ ID NO: 2 or at a position corresponding thereto;
(bp') S, T, C, N, Q, Y, E, K, H, A, V, L, I, M or W at position 205 of the amino acid sequence as shown in SEQ ID NO: 2 or at a position corresponding thereto;
(bq') N, Q, R, V, L or W at position 212 of the amino acid sequence as shown in SEQ ID NO: 2 or at a position corresponding thereto;
(br') Y at position 226 of the amino acid sequence as shown in SEQ ID NO: 2 or at a position corresponding thereto;
(bs') L, I or W at position 233 of the amino acid sequence as shown in SEQ ID NO: 2 or at a position corresponding thereto;
(bt') N at position 237 of the amino acid sequence as shown in SEQ ID NO: 2 or at a position corresponding thereto;
(bu') L at position 238 of the amino acid sequence as shown in SEQ ID NO: 2 or at a position corresponding thereto;
(bv') Y, L or I at position 243 of the amino acid sequence as shown in SEQ ID NO: 2 or at a position corresponding thereto;
(bw') N at position 245 of the amino acid sequence as shown in SEQ ID NO: 2 or at a position corresponding thereto;
(bx') Y, V, L, W or F at position 246 of the amino acid sequence as shown in SEQ ID NO: 2 or at a position corresponding thereto;
(by') S, T, C, N, Q, E, H, A, V, L, I, M, W or F at position 247 of the amino acid sequence as shown in SEQ ID NO: 2 or at a position corresponding thereto;
(bz') F at position 248 of the amino acid sequence as shown in SEQ ID NO: 2 or at a position corresponding thereto;
(ca') F at position 250 of the amino acid sequence as shown in SEQ ID NO: 2 or at a position corresponding thereto;
(cb') G, T, N, Q, D, A, V, L or I at position 251 of the amino acid sequence as shown in SEQ ID NO: 2 or at a position corresponding thereto;
(cc') S, T, C, Q, Y, D, E, R, K, H, A, V, L, I, W, F or P at position 256 of the amino acid sequence as shown in SEQ ID NO: 2 or at a position corresponding thereto;
(cd') V or I at position 257 of the amino acid sequence as shown in SEQ ID NO: 2 or at a position corresponding thereto;
(ce') G, S, T, C, Q, D, E, A, V, L, I or M at position 264 of the amino acid sequence as shown in SEQ ID NO: 2 or at a position corresponding thereto;
(cf') G, T or I at position 273 of the amino acid sequence as shown in SEQ ID NO: 2 or at a position corresponding thereto;

(cg') L, W or F at position 275 of the amino acid sequence as shown in SEQ ID NO: 2 or at a position corresponding thereto;
(ch') V, L, I or F at position 277 of the amino acid sequence as shown in SEQ ID NO: 2 or at a position corresponding thereto;
(ci') R at position 281 of the amino acid sequence as shown in SEQ ID NO: 2 or at a position corresponding thereto;
(cj') T at position 294 of the amino acid sequence as shown in SEQ ID NO: 2 or at a position corresponding thereto;
(ck') V at position 296 of the amino acid sequence as shown in SEQ ID NO: 2 or at a position corresponding thereto;
(cl') L, W or F at position 297 of the amino acid sequence as shown in SEQ ID NO: 2 or at a position corresponding thereto;
(cm') S or A at position 304 of the amino acid sequence as shown in SEQ ID NO: 2 or at a position corresponding thereto;
(cn') N at position 313 of the amino acid sequence as shown in SEQ ID NO: 2 or at a position corresponding thereto;
(co') S, T, C, N, Q, Y, D, E, R, K, H, V, L, I, M, W, F or P at position 319 of the amino acid sequence as shown in SEQ ID NO: 2 or at a position corresponding thereto;
(cp') G, T, V, L, I or F at position 320 of the amino acid sequence as shown in SEQ ID NO: 2 or at a position corresponding thereto;
(cq') W at position 326 of the amino acid sequence as shown in SEQ ID NO: 2 or at a position corresponding thereto;
(cr') M, W or F at position 330 of the amino acid sequence as shown in SEQ ID NO: 2 or at a position corresponding thereto;
(cs') G, T or V at position 332 of the amino acid sequence as shown in SEQ ID NO: 2 or at a position corresponding thereto;
(ct') L at position 334 of the amino acid sequence as shown in SEQ ID NO: 2 or at a position corresponding thereto;
(cu') F at position 335 of the amino acid sequence as shown in SEQ ID NO: 2 or at a position corresponding thereto;
(cv') G, S, T, C, Q, R, K, H, A or V at position 337 of the amino acid sequence as shown in SEQ ID NO: 2 or at a position corresponding thereto;
(cw') S, T, C, Q, Y, D, E, R, K, H, A, V, L, I, M, W, F or P at position 342 of the amino acid sequence as shown in SEQ ID NO: 2 or at a position corresponding thereto;
(cx') T at position 343 of the amino acid sequence as shown in SEQ ID NO: 2 or at a position corresponding thereto;
(cy') R at position 346 of the amino acid sequence as shown in SEQ ID NO: 2 or at a position corresponding thereto;
(cz') L at position 357 of the amino acid sequence as shown in SEQ ID NO: 2 or at a position corresponding thereto;
(da') G, S, Q, V, L, I or F at position 359 of the amino acid sequence as shown in SEQ ID NO: 2 or at a position corresponding thereto;
(db') V, I or W at position 361 of the amino acid sequence as shown in SEQ ID NO: 2 or at a position corresponding thereto;

(dc') N at position 369 of the amino acid sequence as shown in SEQ ID NO: 2 or at a position corresponding thereto;
(dd') W at position 376 of the amino acid sequence as shown in SEQ ID NO: 2 or at a position corresponding thereto;
(de') L or W at position 378 of the amino acid sequence as shown in SEQ ID NO: 2 or at a position corresponding thereto;
(df') D, E, R or K at position 379 of the amino acid sequence as shown in SEQ ID NO: 2 or at a position corresponding thereto;
(dg') F at position 380 of the amino acid sequence as shown in SEQ ID NO: 2 or at a position corresponding thereto;
(dh') Y, M or P at position 385 of the amino acid sequence as shown in SEQ ID NO: 2 or at a position corresponding thereto;
(di') A, L, I or M at position 386 of the amino acid sequence as shown in SEQ ID NO: 2 or at a position corresponding thereto;
(dj') G, Q, E, R, K, H, A, V, L, I, M, W or F at position 387 of the amino acid sequence as shown in SEQ ID NO: 2 or at a position corresponding thereto;
(dk') G, S, T, Y or F at position 390 of the amino acid sequence as shown in SEQ ID NO: 2 or at a position corresponding thereto;
(dl') Q at position 393 of the amino acid sequence as shown in SEQ ID NO: 2 or at a position corresponding thereto;
(dm') G at position 396 of the amino acid sequence as shown in SEQ ID NO: 2 or at a position corresponding thereto;
(dn') T or K at position 403 of the amino acid sequence as shown in SEQ ID NO: 2 or at a position corresponding thereto;
(do') D, V, L, I, W, F or P at position 405 of the amino acid sequence as shown in SEQ ID NO: 2 or at a position corresponding thereto;
(dp') V, W or F at position 406 of the amino acid sequence as shown in SEQ ID NO: 2 or at a position corresponding thereto;
(dq') G or C at position 407 of the amino acid sequence as shown in SEQ ID NO: 2 or at a position corresponding thereto;
(dr') N, Y, I or W at position 408 of the amino acid sequence as shown in SEQ ID NO: 2 or at a position corresponding thereto;
(ds') Y or W at position 409 of the amino acid sequence as shown in SEQ ID NO: 2 or at a position corresponding thereto;
(dt') A, V, L or P at position 411 of the amino acid sequence as shown in SEQ ID NO: 2 or at a position corresponding thereto;
(du') R or V at position 427 of the amino acid sequence as shown in SEQ ID NO: 2 or at a position corresponding thereto; and
(dv') L at position 433 of the amino acid sequence as shown in SEQ ID NO: 2 or at a position corresponding thereto.

3. The mutant protease according to claim 2, which has any of the following amino acid residues or a combination thereof:
the (ar');
the (bk');
the (bm');
the (cj');
the (cm');
the (dc');
a combination of the (e') and (aa');
a combination of the (bc') and (bd');
a combination of the (bm') and (bn');
a combination of the (bm') and (cm');
a combination of the (bm'), (bn') and (cm');
a combination of the (d'), (bm') and (cm');
a combination of the (d'), (bm'), (bn') and (cm');
a combination of the (v'), (cf'), (da') and (dj');
a combination of the (j'), (s'), (y'), (bh') and (do');
a combination of the (as'), (at') and (au');
a combination of the (e'), (v'), (aa'), (bc'), (bd'), (bk'), (cf'), (da'), (dc') and (dj');
a combination of the (e'), (v'), (aa'), (ar'), (bc'), (bd'), (bk'), (cf'), (da'), (dc') and (dj');
a combination of the (j'), (s'), (v'), (y'), (as'), (at'), (au'), (bc'), (bd'), (bh'), (bk'), (cf'), (da'), (dc'), (dj') and (do');
a combination of the (v'), (aa'), (ar'), (bc'), (bd'), (bk'), (cf'), (da'), (dc') and (dj');
a combination of the (v'), (as'), (at'), (au'), (bc'), (bd'), (bk'), (cf'), (da'), (dc') and (dj');
a combination of the (e'), (v'), (aa'), (bc'), (bd'), (bk'), (bo'), (cf'), (co'), (da'), (dc') and (dj');
a combination of the (v'), (as'), (at'), (au'), (bc'), (bd'), (bj'), (bk'), (bq'), (cf'), (da'), (dc'), (df') and (dj');
a combination of the (e'), (v'), (aa'), (ar'), (bc'), (bd'), (bk'), (cf'), (cj'), (da'), (dc') and (dj');
a combination of the (e'), (v'), (z'), (aa'), (ar'), (bc'), (bd'), (bk'), (bo'), (cf), (cj'), (da'), (dc') and (dj');
a combination of the (e'), (v'), (z'), (aa'), (ar'), (bc'), (bd'), (bk'), (bm'), (bn'), (bo'), (cf), (cj'), (da'), (dc') and (dj');
a combination of the (e'), (v'), (z'), (aa'), (ar'), (bc'), (bd'), (bk'), (bm'), (bo'), (cf'), (cj'), (cm'), (da'), (dc'), and (dj');
a combination of the (e'), (v'), (z'), (aa'), (ar'), (bc'), (bd'), (bk'), (bm'), (bn'), (bo'), (cf'), (cj'), (cm'), (da'), (dc') and (dj');
a combination of the (d'), (e'), (v'), (z'), (aa'), (ar'), (bc'), (bd'), (bk'), (bm'), (bo'), (cf), (cj'), (cm'), (da'), (dc') and (dj'); and
a combination of the (d'), (e'), (v'), (z'), (aa'), (ar'), (bc'), (bd'), (bk'), (bm'), (bn'), (bo'), (cf'), (cj'), (cm'), (da'), (dc') and (dj').

4. The mutant protease according to claim 2, which has one or more amino acid residues selected from the group consisting of the following
($d_1$'), ($bm_1$'), ($bn_1$') and ($cm_1$'):
($d_1$') D or E at a position corresponding to position 15 of SEQ ID NO:2;
($bm_1$') D or E at a position corresponding to position 201 of SEQ ID NO:2;
($bn_1$') E at a position corresponding to position 202 of SEQ ID NO:2; and
($cm_1$') A at a position corresponding to position 304 of SEQ ID NO:2.

5. The mutant protease according to claim 1, which consists of an amino acid sequence having an identity of at least 90% with the amino acid sequence as shown in SEQ ID NO:2 and has any of the following amino acid residues 1) to 10):
1) E at a position corresponding to position 303 of SEQ ID NO:2, and A at a position corresponding to position 304 of SEQ ID NO:2;
2) E at a position corresponding to position 303 of SEQ ID NO:2, D at a position corresponding to position 201 of SEQ ID NO:2, and A at a position corresponding to position 304 of SEQ ID NO:2;

3) E at a position corresponding to position 303 of SEQ ID NO:2, D or E at a position corresponding to position 15 of SEQ ID NO:2, D at a position corresponding to position 201 of SEQ ID NO:2, and A at a position corresponding to position 304 of SEQ ID NO:2;
4) E at a position corresponding to position 303 of SEQ ID NO:2, D at a position corresponding to position 201 of SEQ ID NO:2, E at a position corresponding to position 202 of SEQ ID NO:2, and A at a position corresponding to position 304 of SEQ ID NO:2;
5) E at a position corresponding to position 303 of SEQ ID NO:2, D or E at a position corresponding to position 15 of SEQ ID NO:2, D at a position corresponding to position 201 of SEQ ID NO:2, E at a position corresponding to position 202 of SEQ ID NO:2, and A at a position corresponding to position 304 of SEQ ID NO:2;
6) N at a position corresponding to position 303 of SEQ ID NO:2, and A at a position corresponding to position 304 of SEQ ID NO:2;
7) N at a position corresponding to position 303 of SEQ ID NO:2, D at a position corresponding to position 201 of SEQ ID NO:2, and A at a position corresponding to position 304 of SEQ ID NO:2;
8) N at a position corresponding to position 303 of SEQ ID NO:2, D or E at a position corresponding to position 15 of SEQ ID NO:2, D at a position corresponding to position 201 of SEQ ID NO:2, and A at a position corresponding to position 304 of SEQ ID NO:2;
9) N at a position corresponding to position 303 of SEQ ID NO:2, D at a position corresponding to position 201 of SEQ ID NO:2, E at a position corresponding to position 202 of SEQ ID NO:2, and A at a position corresponding to position 304 of SEQ ID NO:2; and
10) N at a position corresponding to position 303 of SEQ ID NO:2, D or E at a position corresponding to position 15 of SEQ ID NO:2, D at a position corresponding to position 201 of SEQ ID NO:2, E at a position corresponding to position 202 of SEQ ID NO:2, and A at a position corresponding to position 304 of SEQ ID NO:2.

6. The mutant protease according to claim 1, which has aspartic acid at a position corresponding to position 30 of SEQ ID NO:2, histidine at a position corresponding to position 68 thereof, and serine at a position corresponding to position 255 thereof.

7. A polynucleotide encoding the mutant protease according to claim 1.

8. A vector comprising the polynucleotide according to claim 7.

9. A transformant comprising the polynucleotide according to claim 7.

10. A method for producing a mutant protease comprising, using the transformant according to claim 9.

11. A detergent composition comprising the mutant protease according to claim 1.

12. A method for producing a mutant protease, comprising substituting the amino acid residue at a position corresponding to position 303 of the amino acid sequence as shown in SEQ ID NO:2 with an amino acid residue selected from the group of consisting of aspartic acid, glutamic acid, phenylalanine, histidine, isoleucine, methionine, proline, glutamine, threonine, valine, tryptophan, and tyrosine in a parent protease,
wherein the parent protease consists of the amino acid sequence as shown in SEQ ID NO:2 or an amino acid sequence having an identity of at least 90% therewith.

13. A method for improving the stability of protease under acidic condition, comprising substituting the amino acid residue at a position corresponding to position 303 of the amino acid sequence as shown in SEQ ID NO: 2 with an amino acid residue selected from the group of consisting of aspartic acid, glutamic acid, phenylalanine, histidine, isoleucine, methionine, proline, glutamine, threonine, valine, tryptophan, and tyrosine in a parent protease, wherein the parent protease consists of the amino acid sequence as shown in SEQ ID NO:2 or an amino acid sequence having an identity of at least 90% therewith.

14. The method according to claim 12, wherein the mutant protease has improved stability under acidic conditions in comparison to a parent protease.

15. The method according to claim 12, which further comprises carrying out one or more amino acid residue substitutions selected from the group consisting of the following $(d_1)$, $(bm_1)$, $(bn_1)$ and $(cm_1)$ with respect to the parent protease:
   $(d_1)$ substitution of S at a position corresponding to position 15 of SEQ ID NO:2 with D or E;
   $(bm_1)$ substitution of H at a position corresponding to position 201 of SEQ ID NO:2 with D or E;
   $(bn_1)$ substitution of V at a position corresponding to position 202 of SEQ ID NO:2 with E; and
   $(cm_1)$ substitution of N at a position corresponding to position 304 of SEQ ID NO:2 with A.

16. The method according to claim 12, which comprises carrying out any of the following 1) to 10) with respect to the parent protease:
   1) Substitution of G at a position corresponding to position 303 of SEQ ID NO:2 with E, and substitution of N at a position corresponding to position 304 of SEQ ID NO: 2 with A;
   2) Substitution of G at a position corresponding to position 303 of SEQ ID NO:2 with E, substitution of H at a position corresponding to position 201 of SEQ ID NO:2 with D, and substitution of N at a position corresponding to position 304 of SEQ ID NO: 2 with A;
   3) Substitution of G at a position corresponding to position 303 of SEQ ID NO:2 with E, substitution of S at a position corresponding to position 15 of SEQ ID NO:2 with D or E, substitution of H at a position corresponding to position 201 of SEQ ID NO:2 with D, and substitution of N at a position corresponding to position 304 of SEQ ID NO:2 with A;
   4) Substitution of G at a position corresponding to position 303 of SEQ ID NO:2 with E, substitution of H at a position corresponding to position 201 of SEQ ID NO:2 with D, substitution of V at a position corresponding to position 202 of SEQ ID NO:2 with E, and substitution of N at a position corresponding to position 304 of SEQ ID NO:2 with A;
   5) Substitution of G at a position corresponding to position 303 of SEQ ID NO:2 with E, substitution of S at a position corresponding to position 15 of SEQ ID NO:2 with D or E, substitution of H at a position corresponding to position 201 of SEQ ID NO:2 with D, substitution of V at a position corresponding to position 202 of SEQ ID NO:2 with E, and substitution of N at a position corresponding to position 304 of SEQ ID NO:2 with A;
   6) Substitution of G at a position corresponding to position 303 of SEQ ID NO:2 with N, and substitution of N at a position corresponding to position 304 of SEQ ID NO:2 with A;

7) substitution of G at a position corresponding to position 303 of SEQ ID NO:2 with N, substitution of H at a position corresponding to position 201 of SEQ ID NO:2 with D, and substitution of N at a position corresponding to position 304 of SEQ ID NO:2 with A;
8) Substitution of G at a position corresponding to position 303 of SEQ ID NO:2 with N, substitution of S at a position corresponding to position 15 of SEQ ID NO:2 with D or E, substitution of H at a position corresponding to position 201 of SEQ ID NO:2 with D, and substitution of N at a position corresponding to position 304 of SEQ ID NO:2 with A;
9) Substitution of G at a position corresponding to position 303 of SEQ ID NO:2 with N, substitution of H at a position corresponding to position 201 of SEQ ID NO:2 with D, substitution of V at a position corresponding to position 202 of SEQ ID NO:2 with E, and substitution of N at a position corresponding to position 304 of SEQ ID NO:2 with A;
10) Substitution of G at a position corresponding to position 303 of SEQ ID NO:2 with N, substitution of S at a position corresponding to position 15 of SEQ ID NO:2 with D or E, substitution of H at a position corresponding to position 201 of SEQ ID NO:2 with D, substitution of V at a position corresponding to position 202 of SEQ ID NO:2 with E, and substitution of N at a position corresponding to position 304 of SEQ ID NO:2 with A.

17. The method according to claim 12, wherein the parent protease has glycine at a position corresponding to position 303 of the amino acid sequence as shown in SEQ ID NO:2.

18. The method according to claim 12, wherein the parent protease has aspartic acid at a position corresponding to position 30 of SEQ ID NO:2, histidine at a position corresponding to position 68 thereof, and serine at a position corresponding to position 255 thereof.

19. A transformant comprising the vector according to claim 8.

20. A method for producing a mutant protein comprising using the transformant according to claim 19.

21. A mutant protease that consists of an amino acid sequence having an identity of at least 90% with the amino acid sequence as shown in SEQ ID NO:2 and that has a combination of N at a position corresponding to position 303 of the amino acid sequence as shown in SEQ ID NO:2 or at a position corresponding thereto and A at position 304 of the amino acid sequence as shown in SEQ ID NO:2 or at a position corresponding thereto.

22. The mutant protease of claim 1, wherein the amino acid residue at position 303 or at a position corresponding to position 303 of the amino acid sequence as shown in SEQ ID NO:2 is E.

* * * * *